(12) United States Patent
Aicher et al.

(10) Patent No.: US 10,189,777 B2
(45) Date of Patent: Jan. 29, 2019

(54) BENZENESULFONAMIDO AND RELATED COMPOUNDS FOR USE AS AGONISTS OF RORγ AND THE TREATMENT OF DISEASE

(71) Applicant: Lycera Corporation, Ann Arbor, MI (US)

(72) Inventors: Thomas D. Aicher, Ann Arbor, MI (US); Donald J. Skalitzky, Saline, MI (US); Clarke B. Taylor, Ann Arbor, MI (US); Chad A. Van Huis, Hartland, MI (US)

(73) Assignee: Lycera Corporation, Ann Arbor, MI (US)

( * ) Notice: Subject to any disclaimer, the term of this patent is extended or adjusted under 35 U.S.C. 154(b) by 0 days.

(21) Appl. No.: 15/308,734

(22) PCT Filed: May 5, 2015

(86) PCT No.: PCT/US2015/029167
§ 371 (c)(1),
(2) Date: Nov. 3, 2016

(87) PCT Pub. No.: WO2015/171558
PCT Pub. Date: Nov. 12, 2015

(65) Prior Publication Data
US 2017/0190659 A1 Jul. 6, 2017

Related U.S. Application Data

(60) Provisional application No. 61/988,707, filed on May 5, 2014.

(51) Int. Cl.
| | |
|---|---|
| C07C 311/21 | (2006.01) |
| C07C 317/18 | (2006.01) |
| C07D 207/09 | (2006.01) |
| C07D 209/14 | (2006.01) |
| C07D 231/08 | (2006.01) |
| C07D 231/20 | (2006.01) |
| C07D 231/56 | (2006.01) |
| C07D 263/58 | (2006.01) |
| C07D 309/08 | (2006.01) |

(52) U.S. Cl.
CPC .......... *C07C 311/21* (2013.01); *C07C 317/18* (2013.01); *C07D 207/09* (2013.01); *C07D 209/14* (2013.01); *C07D 231/08* (2013.01); *C07D 231/20* (2013.01); *C07D 231/56* (2013.01); *C07D 263/58* (2013.01); *C07D 309/08* (2013.01); *C07C 2101/14* (2013.01); *C07C 2102/08* (2013.01); *C07C 2601/14* (2017.05); *C07C 2602/08* (2017.05)

(58) Field of Classification Search
CPC .......................... C07C 311/21; C07D 207/09
See application file for complete search history.

(56) References Cited

U.S. PATENT DOCUMENTS

| | | |
|---|---|---|
| 3,803,184 A | 4/1974 | Njimi et al. |
| 3,936,478 A | 2/1976 | Takeshita et al. |
| 4,952,235 A | 8/1990 | Andree et al. |
| 5,229,109 A | 7/1993 | Grimm et al. |
| 5,229,115 A | 7/1993 | Lynch |
| 5,583,152 A | 12/1996 | Bernstein et al. |
| 5,776,451 A | 7/1998 | Hsu et al. |
| 5,985,903 A | 11/1999 | Assmann et al. |
| 6,020,354 A | 2/2000 | Assmann et al. |
| 6,037,367 A | 3/2000 | Christensen, IV et al. |
| 6,160,001 A | 12/2000 | Assmann et al. |
| 6,172,092 B1 | 1/2001 | Assmann et al. |
| 6,180,643 B1 | 1/2001 | Zablocki et al. |
| 6,348,032 B1 | 2/2002 | Sperl et al. |
| 6,352,985 B1 | 3/2002 | Yamasaki et al. |
| 6,387,939 B1 | 5/2002 | Assmann et al. |
| 6,392,010 B1 | 5/2002 | Salvino et al. |
| 6,403,607 B1 | 6/2002 | Hidaka et al. |
| 6,440,973 B1 | 8/2002 | Zablocki et al. |
| 6,534,535 B1 | 3/2003 | Zhu et al. |
| 6,605,634 B2 | 8/2003 | Zablocki et al. |
| 6,638,960 B2 | 10/2003 | Assmann et al. |
| 6,683,091 B2 | 1/2004 | Asberom et al. |
| 6,828,344 B1 | 12/2004 | Seehra et al. |
| 7,084,176 B2 | 8/2006 | Morie et al. |
| 7,115,750 B1 | 10/2006 | Kato et al. |
| 7,138,401 B2 | 11/2006 | Kasibhatla et al. |
| 7,329,675 B2 | 2/2008 | Cox et al. |
| 7,420,059 B2 | 9/2008 | O'Connor et al. |

(Continued)

FOREIGN PATENT DOCUMENTS

| | | |
|---|---|---|
| EP | 0882718 A1 | 12/1998 |
| EP | 1531848 A2 | 5/2005 |

(Continued)

OTHER PUBLICATIONS

Starck et al (1993): STN International, HCAPLUS database, (Columbus, Ohio), Accession No. 2014: 1493781.*
International Preliminary Report on Patentability for International Application No. PCT/US2015/029167 dated Jul. 4, 2017 (13 pages).
International Search Report and Written Opinion for International Application No. PCT/US2015/017977 dated Jun. 23, 2015 (10 pages).
Zhang et al., "Increasing Human Th17 Differentiation Through Activation of Orphan Nuclear Receptor Retinoid Acid-Related Orphan Receptor γ (RORγ) by a Class of Aryl Amide Compounds," Molecular Pharmacology, vol. 82, pp. 583-590 (2012).
English Abstract JP6-250441 published 1994 (1 page).

(Continued)

*Primary Examiner* — Golam M Shameem
(74) *Attorney, Agent, or Firm* — Dechert LLP

(57) ABSTRACT

The invention provides benzenesulfonamido and related compounds, pharmaceutical compositions, methods of promoting RORγ activity, increasing the amount of IL-17 in a subject, and treating cancer using such benzenesulfonamido and related compounds.

24 Claims, No Drawings

(56) References Cited

U.S. PATENT DOCUMENTS

| | | | |
|---|---|---|---|
| 7,482,342 B2 | 1/2009 | D'Orchymont et al. |
| 7,569,571 B2 | 8/2009 | Dong et al. |
| 7,652,043 B2 | 1/2010 | Beachy et al. |
| 7,696,200 B2 | 4/2010 | Ackermann et al. |
| 7,713,996 B2 | 5/2010 | Ackermann et al. |
| 7,741,495 B2 | 6/2010 | Liou et al. |
| 7,799,933 B2 | 9/2010 | Ceccarelli et al. |
| 7,973,135 B2 | 7/2011 | Liik et al. |
| 7,993,638 B2 | 8/2011 | Cai et al. |
| 7,998,736 B2 | 8/2011 | Morgan et al. |
| 8,067,608 B2 | 11/2011 | Beachy et al. |
| 8,383,099 B2 | 2/2013 | Dudley et al. |
| 8,389,739 B1 | 3/2013 | Thacher et al. |
| 8,541,185 B2 | 9/2013 | Oved et al. |
| 8,741,812 B2 | 6/2014 | Javitt |
| 9,095,583 B2 | 8/2015 | Karstens et al. |
| 9,212,134 B2 * | 12/2015 | Basu ............... C07C 311/44 |
| 9,266,827 B2 | 2/2016 | Aicher et al. |
| 9,394,315 B2 | 7/2016 | Aicher et al. |
| 9,487,490 B2 | 11/2016 | Barr et al. |
| 9,512,111 B2 | 12/2016 | Glick et al. |
| 9,556,168 B2 | 1/2017 | Barr et al. |
| 9,603,838 B2 | 3/2017 | Karstens et al. |
| 9,657,033 B2 | 5/2017 | Aicher et al. |
| 9,663,502 B2 | 5/2017 | Aicher et al. |
| 9,663,522 B2 | 5/2017 | Barr et al. |
| 2005/0037925 A1 | 2/2005 | Tsukamoto et al. |
| 2006/0004000 A1 | 1/2006 | D'Orchymont et al. |
| 2006/0100230 A1 | 5/2006 | Bischoff et al. |
| 2006/0111421 A1 | 5/2006 | Chadwick et al. |
| 2007/0010537 A1 | 1/2007 | Hamamura et al. |
| 2007/0010670 A1 | 1/2007 | Hirata et al. |
| 2007/0049556 A1 | 3/2007 | Zhang et al. |
| 2007/0060567 A1 | 3/2007 | Ackermann et al. |
| 2007/0154487 A1 | 7/2007 | Littman et al. |
| 2007/0185136 A1 | 8/2007 | Courtemanche et al. |
| 2007/0191603 A1 | 8/2007 | Ackermann et al. |
| 2007/0197782 A1 | 8/2007 | Clough et al. |
| 2007/0219257 A1 | 9/2007 | Beachy et al. |
| 2007/0232661 A1 | 10/2007 | Beachy et al. |
| 2007/0281922 A1 | 12/2007 | Liu et al. |
| 2008/0027002 A1 | 1/2008 | Liik et al. |
| 2008/0027100 A1 | 1/2008 | McCormick et al. |
| 2008/0058386 A1 | 3/2008 | Liou et al. |
| 2008/0153805 A1 | 6/2008 | Ceccarelli et al. |
| 2008/0199486 A1 | 8/2008 | Argon et al. |
| 2008/0305169 A1 | 12/2008 | Miki et al. |
| 2009/0005410 A1 | 1/2009 | Charvat et al. |
| 2009/0042851 A1 | 2/2009 | Despeyroux et al. |
| 2009/0075973 A1 | 3/2009 | Newcom et al. |
| 2009/0247502 A1 | 10/2009 | Newcom et al. |
| 2009/0275586 A1 | 11/2009 | Govek et al. |
| 2010/0022515 A1 | 1/2010 | Alper et al. |
| 2010/0087376 A1 | 4/2010 | Kazantseva et al. |
| 2010/0130484 A1 | 5/2010 | Ackermann et al. |
| 2010/0234340 A1 | 9/2010 | Schunk et al. |
| 2010/0310533 A1 | 12/2010 | Yee |
| 2011/0053915 A1 | 3/2011 | Ivaschenko et al. |
| 2011/0112070 A1 | 5/2011 | Baldwin et al. |
| 2011/0118246 A1 | 5/2011 | Baldwin et al. |
| 2011/0130384 A1 | 6/2011 | Setoh et al. |
| 2011/0142814 A1 | 6/2011 | Zanin-Zhorov et al. |
| 2011/0151478 A1 | 6/2011 | Liik et al. |
| 2011/0178063 A1 | 7/2011 | Baldwin et al. |
| 2011/0229504 A1 | 9/2011 | Fritsche et al. |
| 2011/0236363 A1 | 9/2011 | Chang et al. |
| 2012/0135011 A1 | 5/2012 | Podack et al. |
| 2013/0039911 A1 | 2/2013 | Bedi et al. |
| 2013/0045191 A1 | 2/2013 | Weinschenk et al. |
| 2013/0102075 A1 | 4/2013 | Vera et al. |
| 2013/0102542 A1 | 4/2013 | Kazantseva et al. |
| 2014/0038942 A1 | 2/2014 | Karstens et al. |
| 2014/0088094 A1 | 3/2014 | Glick et al. |
| 2014/0186295 A1 | 7/2014 | Kupper et al. |
| 2014/0187504 A1 | 7/2014 | Chaturvedi |
| 2014/0187554 A1 | 7/2014 | Kamenecka et al. |
| 2014/0314795 A1 | 10/2014 | Riddell et al. |
| 2014/0343023 A1 | 11/2014 | Wolfrum et al. |
| 2015/0017120 A1 | 1/2015 | Wittrup et al. |
| 2015/0111877 A1 | 4/2015 | Aicher et al. |
| 2015/0126493 A1 | 5/2015 | Aicher et al. |
| 2015/0133437 A1 | 5/2015 | Aicher et al. |
| 2015/0191434 A1 | 7/2015 | Barr et al. |
| 2015/0210687 A1 | 7/2015 | Barr et al. |
| 2015/0218096 A1 | 8/2015 | Barr et al. |
| 2015/0218169 A1 | 8/2015 | Barr et al. |
| 2015/0297566 A1 | 10/2015 | Karstens et al. |
| 2016/0304476 A1 | 10/2016 | Aicher et al. |
| 2016/0304505 A1 | 10/2016 | Aicher et al. |
| 2016/0311787 A1 | 10/2016 | Aicher et al. |
| 2016/0318951 A1 | 11/2016 | Aicher et al. |
| 2017/0183331 A1 | 6/2017 | Aicher et al. |

FOREIGN PATENT DOCUMENTS

| | | |
|---|---|---|
| EP | 1768662 A2 | 4/2007 |
| EP | 1820515 A1 | 8/2007 |
| EP | 2038301 A2 | 3/2009 |
| EP | 2158327 A2 | 3/2010 |
| EP | 2181710 A1 | 5/2010 |
| EP | 2321407 A1 | 5/2011 |
| EP | 2462165 A1 | 6/2012 |
| EP | 2542590 A2 | 1/2013 |
| EP | 2547354 A2 | 1/2013 |
| EP | 2158327 B1 | 5/2013 |
| EP | 2649086 A1 | 10/2013 |
| EP | 2688594 A2 | 1/2014 |
| EP | 2689010 A1 | 1/2014 |
| EP | 2825197 A1 | 1/2015 |
| JP | 6-250441 A | 9/1994 |
| JP | 2004307487 A | 11/2004 |
| WO | WO-92/13856 A1 | 8/1992 |
| WO | WO-97/01561 A1 | 1/1997 |
| WO | WO-1997/036580 | 10/1997 |
| WO | WO-97/48697 A1 | 12/1997 |
| WO | WO-98/22457 A1 | 5/1998 |
| WO | WO-00/17202 A1 | 3/2000 |
| WO | WO-2000/054759 | 9/2000 |
| WO | WO-01/012600 A1 | 2/2001 |
| WO | WO-2001/012186 A1 | 2/2001 |
| WO | WO-02/14361 A2 | 2/2002 |
| WO | WO-02/100819 A1 | 12/2002 |
| WO | WO-03/014075 A2 | 2/2003 |
| WO | WO-03/104428 A2 | 12/2003 |
| WO | WO-2004/050631 A1 | 6/2004 |
| WO | WO-2004/056820 A1 | 7/2004 |
| WO | WO-2004/056830 A1 | 7/2004 |
| WO | WO-05/028434 A2 | 3/2005 |
| WO | WO-2005/033048 A2 | 4/2005 |
| WO | WO-2005/033288 A2 | 4/2005 |
| WO | WO-2005/037834 A1 | 4/2005 |
| WO | WO-2005/058847 A1 | 6/2005 |
| WO | WO-2005/084208 A2 | 9/2005 |
| WO | WO-2005/120558 A2 | 12/2005 |
| WO | WO-2006/007486 A2 | 1/2006 |
| WO | WO-2006/057460 A1 | 6/2006 |
| WO | WO-2006/115509 A2 | 11/2006 |
| WO | WO-2007/010259 A1 | 1/2007 |
| WO | WO-2007/024944 A1 | 3/2007 |
| WO | WO-2007/031429 A1 | 3/2007 |
| WO | WO-2007/093507 A1 | 8/2007 |
| WO | WO-2007/113337 A1 | 10/2007 |
| WO | WO-2007/125405 A2 | 11/2007 |
| WO | WO-2007/138998 A1 | 12/2007 |
| WO | WO-2008/003703 A1 | 1/2008 |
| WO | WO-2008/008923 A2 | 1/2008 |
| WO | WO-2008/045664 A2 | 4/2008 |
| WO | WO-2008/062740 A1 | 5/2008 |
| WO | WO-2008/074692 A1 | 6/2008 |
| WO | WO-2008/097428 A2 | 8/2008 |
| WO | WO-2008/150827 A1 | 12/2008 |
| WO | WO-2008/151200 A2 | 12/2008 |
| WO | WO-2009/032667 A1 | 3/2009 |
| WO | WO-2009/035997 A2 | 3/2009 |

(56) References Cited

FOREIGN PATENT DOCUMENTS

| | | |
|---|---|---|
| WO | WO-2009/077956 A2 | 6/2009 |
| WO | WO-2009/147187 A1 | 12/2009 |
| WO | WO-2009/149819 A1 | 12/2009 |
| WO | WO-2009/149820 A1 | 12/2009 |
| WO | WO-2009/157196 A1 | 12/2009 |
| WO | WO-2010/017827 A1 | 2/2010 |
| WO | WO-2010/030947 A1 | 3/2010 |
| WO | WO-2010/038901 A1 | 4/2010 |
| WO | WO-2010/057101 A2 | 5/2010 |
| WO | WO-2010/059602 A2 | 5/2010 |
| WO | WO-2010/071853 A1 | 6/2010 |
| WO | WO-2010/102958 A1 | 9/2010 |
| WO | WO-2010/117425 A1 | 10/2010 |
| WO | WO-2010/123139 A1 | 10/2010 |
| WO | WO-2010/125082 A1 | 11/2010 |
| WO | WO-2011/017303 A1 | 2/2011 |
| WO | WO-2011/019634 A2 | 2/2011 |
| WO | WO-2011/059839 A1 | 5/2011 |
| WO | WO-2011/067364 A1 | 6/2011 |
| WO | WO-2011/067365 A1 | 6/2011 |
| WO | WO-2011/067366 A1 | 6/2011 |
| WO | WO-2011/109059 A1 | 9/2011 |
| WO | WO-2011/109789 A2 | 9/2011 |
| WO | WO-2011/113819 A2 | 9/2011 |
| WO | WO-2011/115892 A1 | 9/2011 |
| WO | WO-2012/032065 A1 | 3/2012 |
| WO | WO-2012/032067 A1 | 3/2012 |
| WO | WO-2012/037108 A1 | 3/2012 |
| WO | WO-2012/064744 A2 | 5/2012 |
| WO | WO-2012/079000 A1 | 6/2012 |
| WO | WO-2012/127464 A2 | 9/2012 |
| WO | WO-2012/129394 A2 | 9/2012 |
| WO | WO-2012/129514 A1 | 9/2012 |
| WO | WO-2012/139775 A1 | 10/2012 |
| WO | WO-2012/129394 A9 | 11/2012 |
| WO | WO-2012/178108 A1 | 12/2012 |
| WO | WO-2013/045431 A1 | 4/2013 |
| WO | WO-2013/074916 A1 | 5/2013 |
| WO | WO-2013/135588 A1 | 9/2013 |
| WO | WO-2013/167136 A1 | 11/2013 |
| WO | WO-2013/169588 A1 | 11/2013 |
| WO | WO-2013/169704 A2 | 11/2013 |
| WO | WO-2013/169864 A2 | 11/2013 |
| WO | WO-2013/176740 A1 | 11/2013 |
| WO | WO-2014/028669 A1 | 2/2014 |
| WO | WO-2014/031174 A1 | 2/2014 |
| WO | WO-2014/095757 A1 | 6/2014 |
| WO | WO-2014/201378 A1 | 12/2014 |
| WO | WO-2014/201378 A9 | 1/2015 |
| WO | WO-2015/131035 A1 | 9/2015 |
| WO | WO-2015/171610 A2 | 11/2015 |
| WO | WO-2016/179343 A1 | 11/2016 |

OTHER PUBLICATIONS

English Abstract of JP2004307487A published 2004 (2 pages).
International Search Report and Written Opinion for PCT/US2011/059788 dated May 23, 2012 (23 pages).
International Search Report and Written Opinion for PCT/US2013/040085 dated Oct. 23, 2013 (9 pages).
Annunziato et al., "Type 17 T helper cells-origins, features and possible roles in rheumatic disease," 5 Nat. Rev. Rheumatol. 325-31 (2009).
Boaventura et al., "Human mucosal leishmaniasis: Neutrophils infiltrate areas of tissue damage that express high levels of Th17-related cytokines," 40 Eur. J. Immunol. 2830-36 (2010).
Buonocore et al., "Innate lymphoid cells drive interleukin-23-dependent innate intestinal pathology," 464 Nature 1371-75 (2010).
Eberl et al., "An essential function for the nuclear receptor RORγt in the generation of fetal lymphoid tissue inducer cells," 5(1) Nat. Immunol. 64-73 (2004).
Figueroa-Vega et al., "Increased Circulating Pro-Inflammatory Cytokines and Th17 Lymphocytes in Hashimoto's Thyroiditis," 95(2) J. Clin. Endocrinol. Metab. 953-62 (2010).
Gennaro (ed.), Remington: The Science and Practice of Pharmacy, 20th edition (2000).
He et al., "RORγt, a Novel Isoform of an Orphan Receptor, Negatively Regulates Fas Ligand Expression and IL-2 Production in T Cells," 9 Immunity 797-806 (1998).
Hirose et al., "RORγ: the third member of ROR/RZR orphan receptor subfamily that is highly expressed in skeletal muscle," 205 Biochem. Biophys. Res. Comm. 1976-83 (1994).
Hueber et al., "Cutting Edge: Mast Cells Express IL-17A in Rheumatoid Arthritis Synovium," 184 J. Immunol. 3336-40 (2010).
Ivanov et al., "The Orphan Nuclear Receptor RORγt Directs the Differentiation Program of Proinflammatory IL-17+ T Helper Cells," 126 Cell 1121-33 (2006).
Jia et al., "The T helper type 17/regulatory T cell imbalance in patients with acute Kawasaki disease," 162 Clin. Exp. Immunol. 131-37 (2010).
Jin et al., "Structural Basis for Hydroxycholesterols as Natural Ligands of Orphan Nuclear Receptor RORγ," Mol. Endocrinol. (2010) vol. 24, No. 5, pp. 923-929.
Kastelein et al., "Discovery and Biology of IL-23 and IL-27: Related but Functionally Distinct Regulators of Inflammation," 25 Annu. Rev. Immunol. 221-42 (2007).
Kurebayashi et al., "Selective LXXLL peptides antagonize transcriptional activation by the retinoid-related orphan receptor RORγ," 315 Biochem. Biophys. Res. Comm. 919-27 (2004).
Louten et al., "Development and function of TH17 cells in health and disease," 123(5) J. Allergy Clin. Immunol. 1004-11 (2009).
Miossec et al., "Interleukin-17 and Type 17 Helper T Cells," 361(9) New Eng. J. Med. 888-98 (2009).
Sun et al., "Requirement for RORγ in Thymocyte Survival and Lymphoid Organ Development," 288 Science 2369-72 (2000).
Sutton et al., "Interleukin-1 and IL-23 Induce Innate IL-17 Production from γδ T Cells, Amplifying Th17 Responses and Autoimmunity," 31 Immunity 331-41 (2009).
Wang et al., "Identification of SR1078, a Synthetic Agonist for the Orphan Nuclear Receptors RORα and RORγ," 5(11) ACS Chem. Biol. 1029-34 (2010).
Xie et al., "RORγt Recruits Steroid Receptor Coactivators to Ensure Thymocyte Survival," 175(6) J. Immunol. 3800-09 (2005).
Yang et al., "T Helper 17 Lineage Differentiation is programmed by Orphan Nuclear Receptors RORα and RORγ," 28 Immunity 29-39 (2008).
André et al., "Disruption of retinoid-related orphan receptor ß changes circadian behaviour, causes retinal degeneration and leads to vacillans phenotype in mice," 17(14) The EMBO J. 3867-77 (1998).
Becker-André et al., "Identification of nuclear receptor mRNAs by RT-PCR amplification of conserved zinc-finger motif sequences," 194(3) Biochem. Biophys. Res. Comm. 1371-79 (1993).
Burris et al., "Targeting Orphan Nuclear Receptors for Treatment of Metabolic Diseases and Autoimmunity," 19(1) Chem. Biol. 51-59 (2012).
Cai, et al., "Pivotal Role of Dermal IL-17-Producing γδ T Cells in Skin Inflammation", Immunity (2011) vol. 35, pp. 596-610.
Carlberg et al., "RZRs, a new family of retinoid-related orphan receptors that function as both monomers and homodimers," 8 Mol. Endocrinol. 757-70 (1994).
D. van der Heijde, et al., "Secukinumab Provides Significant and Sustained Inhibition of Joint Structural Damage in a Phase III Study of Active Psoriatic Arthritis" Arthritis & Rheumatology Brief Report, Accepted Article DOI: 10.1002/art.39685, American College of Rheumatology, (2016) pp. 1-27.
Baeten, et al., "Secukinumab, an Interleukin-17A Inhibitor, in Ankylosing Spondylitis", The New England Journal of Medicine, (2015) vol. 373, pp. 2534-2548.
Dussault et al., "Orphan nuclear receptor RORα-deficient mice display the cerebellar defects of staggerer," 70 Mech. Develop. 147-53 (1998).
Giguère et al., "Isoform-specific amino-terminal domains dictate DNA-binding properties of RORα, a novel family of orphan hormone nuclear receptors," 8 Genes & Develop. 538-53 (1994).

(56) References Cited

OTHER PUBLICATIONS

Huh et al., "Small molecule inhibitors of RORγt: Targeting Th17 cells and other applications," 42 Eur. J. Immunol. 2232-2237 (2012).
Krueger, "A welcome surprise in psoriasis", Nature Medicine, (2012) vol. 18, No. 12, pp. 1750-1751.
Leonardi, et al., "Anti-Interleukin-17 Monoclonal Antibody Ixekizumab in Chronic Plaque Psoriasis", The New England Journal of Medicine, (2012) vol. 366, Iss. 13, pp. 1-10.
Martinez, "Th17-biased RORγt transgenic mice become susceptible to a viral model for multiple sclerosis", Brain, Behavior, and Immunity, (2014) vol. 43, pp. 86-97.
Medvedev et al., "Cloning of a cDNA encoding the murine orphan receptor RZR/RORγ and characterization of its response element," 181 Gene 199-206 (1996).
Nakajima, et al., "IL-17A as an Inducer for Th2 Immune Responses in Murine Atopic Dermatitis Models", Journal of Investigative Dermatology, (2014) vol. 134, pp. 2122-2130.
Ortiz et al., "TOR: a new orphan receptor expressed in the thymus that can modulate retinoid and thyroid hormone signals," 9 Mol. Endocrinol. 1679-91 (1995).
Papp, et al. "Brodalumab, an Anti-Interleukin-17-Receptor Antibody for Psoriasis", The New England Journal of Medicine, (2012) vol. 366, Iss. 13, 9 pgs.
Skepner, J. et al."Pharmacologic Inhibition of RORγt Regulates Th17 Signature Gene Expression and Suppresses Cutaneous Inflammation in Vivo," downloaded from the Internet at http://www.jimmunol.org/cgi/doi/10.4049/jimmunol.1302190 on Feb. 17, 2014, published in final edited form in *J. Immunol.* (2014) vol. 192, No. 6, pp. 2564-2575.
Smith, "The Bench-to-Bedside Story of IL-17 and the Therapeutic Efficacy of its Targeting in Spondyloarthritis", Curr Rheumatol Rep. (2016) vol. 18, pp. 1-10.
Solt et al., "Action of RORs and their ligands in (patho)physiology," 23(12) Trends in Endocrinology and Metabolism. 619-627 (2012).
Tlustochowicz, et al. "Efficacy and Safety of Subcutaneous and Intravenous Loading Dose Regimens of Secukinumab in Patients with Active Rheumatoid Arthritis: Results from a Randomized Phase II Study" The Journal of Rheumatology, (2016) vol. 43, No. 3, pp. 495-503.
Villey et al., "RORγT, a thymus-specific isoform of the orphan nuclear receptor RORγ/TOR, is up-regulated by signaling through the pre-T cell receptor and binds to the TEA promoter," 29 Eur. J. Immunol. 4072-80 (1999).
Wiesenberg et al., "Transcriptional activation of the nuclear receptor RZRα by the pineal gland hormone melatonin and identification of CGP 52608 as a synthetic ligand," 23(3) Nucl. Acids Res. 327-33 (1995).
Xiao, et al., "Small-Molecule RORγt Antagonists Inhibit T Helper 17 Cell Transcriptional Network by Divergent Mechanisms", Immunity (2014) vol. 40, pp. 477-489.
Arisawa et al., "Development of Isomerization and Cycloisomerization with Use of a Ruthenium Hydride with N-Heterocyclic Carbene and Its Application to the Synthesis of Heterocycles," 71 J. Org. Chem. 4255-61 (2006).
Berge et al., "Pharmaceutical salts," 66(1) J. Pharm. Sci. 1-19 (1977).
Bhagawanth et al., "Room-Temperature Pd-Catalyzed Amidation of Aryl Bromides Using tert-Butyl Carbamate," 74 J. Org. Chem. 4634-37 (2009).
Boger et al., "Regiocontrolled Nucleophilic Addition to Selectively Activated p-Quinone Diimines: Alternative Preparation of a Key Intermediate Employed in the Preparation of the CC-1065 Left-Hand Subunit," 55 J. Org. Chem. 1379-90 (1990).
Carroll et al., "Synthesis, Nicotinic Acetylcholine Receptor Binding, and Antinociceptive Properties of 2-exo-2-(2',3'-Disubstituted 5'-pyridinyl)-y-azabicyclo[2.2.1]heptanes: Epibatidine Analogues," 45 J. Med. Chem. 4755-61 (2002).
Chang et al., "7-Aroyl-aminoindoline-1-sulfonamides as a Novel Class of Potent Antitubulin Agents," 49 J. Med. Chem. 6656-59 (2006).
Colbon et al., "Double Arylation of Allyl Alcohol via a One-Pot Heck Arylation—Isomerization—Acylation Cascade," 13 Org. Lett. 5456-59 (2011).
De et al., Methods in Molecular Biology 1184, second edition, Human Press (2014).
Gould, "Salt selection for basic drugs," 33 Int'l J. Pharmaceutics 201-217 (1986).
Grasa et al., "Amination Reactions of Aryl Halides with Nitrogen-Containing Reagents Mediated by Palladium/Imidazolium Salt Systems," 66 J. Org. Chem. 7729-37 (2001).
Greene & Wuts, Protective Groups in Organic Synthesis, 2d Edition (1991).
Guimond et al., "Rhodium(III)-Catalyzed Isoquinolone Synthesis: The N—O Bond as a Handle for C—N Bond Formation and Catalyst Turnover," 132(20) J. Am. Chem. Soc. 6908-09 (2010).
Hanessian et al., "A versatile protocol for the stereocontrolled elaboration of vicinal secondary and tertiary centers of relevance to natural product synthesis," 52(6) J. Org. Chem. 1170-72 (1987).
Hauser et al., "Relative Ease of Cyclization of 2-, 3-, and 4-Aminopyridine Derivatives. Synthesis of Naphthyridines," 15 J. Org. Chem. 1224-32 (1950).
International Search Report and Written Opinion for PCT/US2013/039422 dated Oct. 11, 2013 (9 pages).
International Search Report and Written Opinion for PCT/US2013/039839 dated Oct. 18, 2013 (8 pages).
Ishikura et al., "An Efficient Synthesis of 3-Heteroarylpyridines via Diethyl-(3-pyridyl)-borane," Synthesis 936-38 (1984).
Jayashree et al., "Design and synthesis of 2-quinolones as antioxidants and antimicrobials: a rational approach," 19 Med. Chem. Res. 193-209 (2010).
Jiang et al., "Synthesis and Cytotoxicity Evaluation of Novel Indolylpyrimidines and Indolylpyrazines as Potential Antitumor Agents," 9 Bioorg. Med. Chem. 1149-54 (2001).
Li et al., "Chemical Libraries via Sequential C—H Functionalization of Phenols," 10 J. Comb. Chem. 170-74 (2008).
Li et al., "Synthesis and Resolution of a Novel Chiral Diamine Ligand and Application to Asymmetric Lithiation-Substitution," 2 Org. Lett. 875-78 (2000).
Liu et al., "1-Sulfonylindazoles as potent and selective 5-HT6 ligands," 19 Bioorg. Med. Chem. Lett. 2413-15 (2009).
Murase et al., "A New Concise Synthesis of Arcyriacyanin A and Its Unique Inhibitory Activity against a Panel of Human Cancer Cell Line," 48(1) Chem. Pharm. Bull. 81-84 (2000).
Ninomiya et al., "Phosphorous in Organic Synthesis—VII: Diphenyl Phosphorazidate (DPPA). A New Convenient Reagent for a Modified Curtius Reaction," 30 Tetrahedron 2151-57 (1975).
Nyrkova et al., "Synthesis of a New Heterocyclic System—3,4-Diazaphenoxazine," 1(9) J. Org. Chem. USSR, 1711-14, translating 1(9) Zh. Org. Khimii, 1688-91 (1965).
Santilli et al., "Synthesis of 5,6,7,8-Tetrahydro-5-oxopyrido[2,3-d] pyrimidine-6-carbonitriles and -6-carboxylic Acid Esters," 12 J. Het. Chem. 311-16 (1975).
Skraup, "Eine Synthese des Chinolins," 13 Berichte 2086-87 (1880).
Stefko et al., "General and Modular Synthesis of Isomeric 5-Substituted Pyridin-2-yl and 6-Substituted Pyridin-3-yl C-Ribonucleosides Bearing Diverse Alkyl, Aryl, Hetaryl, Amino, Carbamoyl, and Hydroxy Groups," 76 J. Org. Chem. 6619-35 (2011).
STN Columbus, pp. 1-40 (2011).
Takano et al., "A new synthesis of a steroid side chain via stereocontrolled protonation: synthesis of (−)-desmosterol," 14 J. Chem. Soc., Chem. Commun. 760-61 (1983).
Van Heerden et al., "Dibutylboron triflate promoted conjugate addition of benzylic and allylic organocopper reagents to chiral α,β-unsaturated N-acyl imidazolidinones" 38(10) Tet. Lett. 182-124 (1997).
Wang et al., "Synthesis of new carbon-11-labeled 7-aroyl-aminoindoline-1-sulfonamides as potential PET agents for imaging of tubulin polymerization in cancers," 51(1) J. Label. Compd. Radiopharm. 6-11 (2008).

(56) References Cited

OTHER PUBLICATIONS

Yeh et al., "Practical Cu-catalyzed amination of functionalized heteroaryl halides," 47(34) Tetrahedron Lett. 6011-16 (2006).
Zhu et al., "The Direct Formulation of Functionalized Alkyl(aryl)zinc halides by Oxidative Addition of Highly Reactive Zinc with Organic Halides and Their Reactions with Acid Chlorides, α,β-Unsaturated Ketones, and Allylic, Aryl, and Vinyl Halides," 56 J. Org. Chem. 1445-53 (1991).
International Search Report and Written Opinion for PCT/US2014/071663 dated Apr. 17, 2015 (6 pages).
International Search Report and Written Opinion for PCT/US2014/071671 dated Apr. 28, 2015 (10 pages).
International Search Report and Written Opinion for PCT/US2014/071656 dated Mar. 12, 2015 (8 pages).
Yang, T. et al. "Discovery of Tertiary Amine and Indole Derivatives as Potent RORγt Inverse Agonists," ACS Med. Chem. Lett. (2014) vol. 5, pp. 65-68.
Jun., C. H. "Adoptive T cell therapy for cancer in the clinic," J. Clin. Invest. (2007) vol. 117, No. 6, pp. 1466-1476.
Zhu, J. et al. "Differentiation of Effector CD4 T Cell Populations," Author manuscript available in PMC on Nov. 20, 2012, published in final edited form in Annu. Rev. Immunol. (2010) vol. 28, pp. 445-489.
Martin-Orozco, N. et al. "Th17 cells promote cytotoxic T cell activation in tumor immunity," Author manuscript available in PMC on Nov. 20, 2010, published in final edited form in Immunity (2009) vol. 31, pp. 787-798.
Pardoll, D. M. "The blockade of immune checkpoints in cancer immunotherapy," Nature Rev. Cancer (2012) vol. 12, pp. 252-264.
Restifo, N. P. et al."Adoptive immunotherapy for cancer: harnessing the T cell response," Nature Rev. Immunol. (2012) vol. 12, pp. 269-281.
Drug Discovery & Development "Lycera's Oral Immunotherapy May Have Anti-Cancer Activity," Dated Nov. 7, 2014. (2 pages).
Lycera "Lycera Announces Research Showing Promising Anti-Cancer Activity of Novel, Oral Immunotherapy Candidates," Press release dated Feb. 9, 2015. (2 pages).
X. Hu et al. In Poster Presentation Entitled "Novel, Synthetic RORgamma Agonist Compounds as a Potential Anti-Cancer Approach" at Society for Immunotherapy of Cancer (SITC) Meeting 2014, Nov. 6-9, 2014.
Huang, Z. et al. "Retinoid-related orphan receptor γt is a potential therapeutic target for controlling inflammatory autoimmunity," Expert Opin. Ther. Targets (2007) vol. 11, No. 6, pp. 737-743.
Wang et al., "Modulation of Retinoic Acid Receptor-related Orphan Receptor α and γ Activity by 7-Oxygenated Sterol Ligands," J. Biol. Chem. (2010) vol. 285, No. 7, pp. 5013-5025.
Bai et al., "Sulfation of 25-hydroxycholesterol by SULT2B1b decreases cellular lipids via the LXR/SREBP-1c signaling pathway in human aortic endothelial cells," Atherosclerosis, vol. 214, pp. 350-356 (author's manuscript pp. 1-14) (2011).
Bensinger et al., "LXR signaling couples sterol metabolism to proliferation in the acquired immune response," Cell, vol. 134, pp. 97-111 (2008).
Brown et al., "Oxysterols and atherosclerosis," Atherosclerosis, vol. 142, pp. 1-28 (1999).
Chen et al., "Enzymatic reduction of oxysterols impairs LXR signaling in cultured cells and the livers of mice," Cell Metab., vol. 5, pp. 73-79 (2007).
Cheng et al.,"Increased cholesterol content in Gammadelta (γδ) T lymphocytes differentially regulates their activation," PLoS One 8, pp. 1-9 (2013).
Cook et al., "24-hydroxycholesterol sulfation by human cytosolic sulfotransferases: formation of monosulfates and disulfates, molecular modeling, sulfatase sensitivity, and inhibition of liver X receptor activation," Drug Metab. Dispos., vol. 37, pp. 2069-2078 (2009).
Hanyu et al., "Cholesterol sulfate induces expression of the skin barrier protein filaggrin in normal human epidermal keratinocytes through induction of RORα," Biochim. Biophys. Res. Commun., vol. 428, pp. 99-104 (2012).

Hu et al., "Sterol metabolism controls $T_H17$ differentiation by generating endogenous RORγ agonists," Nature Chemical Biology, vol. 11, pp. 141-147 (2015).
Iida et al., "Tumor-Infiltrating CD4+Th17 Cells Produce IL-17 in Tumor Microenvironment and Promote Tumor Progression in Human Gastric Cancer," Oncology Reports, vol. 25, pp. 1271-1277 (2011).
Ikonen, "Cellular cholesterol trafficking and compartmentalization," Nat. Rev. Mol. Cell Biol., vol. 9, pp. 125-138 (2008).
Kallen et al.,"Crystal structure of the human RORα ligand binding domain in complex with cholesterol sulfate at 2.2 Å," J. Biol. Chem., vol. 279, pp. 14033-14038 (2004).
Kidani et al., "The sterol regulatory element binding proteins are essential for the metabolic programming of effector T cells and adaptive immunity," Nat. Immunol., vol. 14, pp. 489-499 (2013).
Liao et al., "Association Between Th17-Related Cytokines and Risk of Non-Small Cell Lung Cancer Among Patients With or Without Chronic Obstructive Pulmonary Disease," Cancer, pp. 3122-3129 (2015).
Ma et al., "25-Hydroxycholesterol-3-sulfate regulates macrophage lipid metabolism via the LXR/SREBP-1 signaling pathway," Am. J. Physiol. Endocrinol. Metab., vol. 295, pp. E1369-E1379 (2008).
Solt et al., "Identification of a selective RORγ ligand that suppresses $T_H17$ cells and stimulates T regulatory cells," ACS Chem. Biol., vol. 7, pp. 1515-1519 (2012).
Song et al., "Auto-oxidized cholesterol sulfates are antagonistic ligands of liver X receptors: implications for the development and treatment of atherosclerosis," Steroids, vol. 66, pp. 473-479 (2001).
Spann et al., "Regulated accumulation of desmosterol integrates macrophage lipid metabolism and inflammatory responses," Cell, vol. 151, pp. 138-152 (2012).
Spann et al., "Sterols and oxysterols in immune cell function," Nat. Immunol., vol. 14, pp. 893-900 (2013).
Wang et al., "A second class of nuclear receptors for oxysterols: Regulation of RORα and RORγ activity by 24S-hydroxycholesterol (cerebrosterol)," Biochim. Biophys. Acta, vol. 1801, pp. 917-923 (2010).
Yang et al., "Sterol intermediates from cholesterol biosynthetic pathway as liver X receptor ligands," J. Biol. Chem., vol. 281, pp. 27816-27826 (2006).
Arellano et al., "Clinical uses of GM-CSF, a critical appraisal and update," Biologics: Targets & Therapy, vol. 2, pp. 13-27 (2008).
Chang et al., "Synthetic RORγt Agonists Enhance Protective Immunity," ACS Chem. Biol., Just Accepted Manuscript—DOI: 10.1021/acschembio.5b00899—Publication Date (Web): Jan. 19, 2016, (30 pages).
Chen et al., "Th1-, Th2-, and Th17-associated cytokine expression in hypopharyngeal carcinoma and clinical significance," Eur Arch Otorhinolaryngol, DOI: 10.1007/s00405-015-3779-2, 8 pages, (2015).
Codarri et al., "RORγt drives production of the cytokine GM-CSF in helper T cells, which is essential for the effector phase of autoimmune neuroinflammation," Nature Immunology, vol. 12, pp. 560-568, (2011).
Gnerlich et al.,"Induction of Th17 Cells in the Tumor Microenvironment Improves Survival in a Murine Model of Pancreatic Cancer," The Journal of Immunology, vol. 185, pp. 4063-4071, (2010).
Hinrichs et al., "Type 17 CD8+ T cells display enhanced antitumor immunity," Blood, vol. 114, pp. 596-599, (2009).
Hu et al. In "RORγ Agonists as a Novel Immunotherapy Approach for Cancer" in American Association for Cancer Research Annual Meeting in Philadelphia, Pennsylvania, Apr. 21, 2015, Poster Session: Novel Immunomodulators, Abstract No. 4273.
Kryczek et al.,"Phenotype, distribution, generation, and functional and clinical relevance of Th17 cells in the human tumor environments," The American Society of Hematology, vol. 114, pp. 1141-1149, (2009).
Ma et al., "Contribution of IL-17-producing γ8 T cells to the efficacy of anticancer chemotherapy," J. Exp. Med., vol. 208, pp. 491-503, (2011).
Munegowda et al., "Th17 and Th17-stimulated CD8 + T cells play a distinct role in Th17-induced preventive and therapeutic antitumor immunity," Cancer Immunol Immunother, vol. 60, (2011), one page, Abstract only.

(56) References Cited

OTHER PUBLICATIONS

Muranski et al., "Tumor-specific Th17-polarized cells eradicate large established melanoma," *Blood*, vol. 112, pp. 362-373, (2008).
Nelson et al., "The Inducible Costimulator Augments Tc17 Cell Responses to Self and Tumor Tissue," *The Journal of Immunology*, vol. 194, pp. 1737-1747, (2015).
Nunez et al., "T helper type 17 cells contribute to anti-tumour immunity and promote the recruitment of T helper type 1 cells to the tumour," *Immunology*, vol. 139, pp. 61-71, (2012).
Soroosh et al., "Oxysterols are agonist ligands of RORγt and drive Th17 cell differentiation," PNAS, vol. 111, pp. 12163-12168, (2014).
International Search Report and Written Opinion for International Application No. PCT/US2015/029167 dated Jun. 13, 2017 (25 pages).
International Search Report and Written Opinion for International Application No. PCT/US2015/029240 dated Jan. 29, 2016 (14 pages).
International Search Report and Written Opinion for International Application No. PCT/US2016/030882 dated Jun. 6, 2016 (17 pages).
International Search Report and Written Opinion for International Application No. PCT/US2016/036889 dated Sep. 9, 2016 (17 pages).
Yang, S. M. and Murray, W. V. "Microwave assisted ring-opening of epoxides with N-biaryl sulfonamides in the synthesis of matrix metalloproteinase-9 inhibitors," *Tetrahedron Lett*. (2008) vol. 49, No. 5, pp. 835-839.
CAS Registry No. 1012413-39-6; STN Entry Date: Apr. 6, 2008; Chemical name: Benzenesulfonamide, N-[4-[(2-fluorophenyl)methoxy]phenyl]-N-methyl-.
CAS Registry No. 632292-33-2; STN Entry Date: Dec. 30, 2003; Chemical name: 2-[[1,2,3,4-tetrahydro-1-[(4-methylphenyl)sulfonyl]-6-quinolinyl]methyl]-1H-isoindole-1,3(2H)-dione.
Zhu, W. et al. "Potent 11β-Hydroxylase Inhibitors with Inverse Metabolic Stability in Human Plasma and Hepatic S9 Fractions to Promote Wound Healing," *J. Med. Chem*. (2014) vol. 57, No. 18, pp. 7811-7817.
Zhao, S.H. et al. "3,4-Dihydro-2H-benzo[1,4]oxazine Derivatives as 5-$HT_6$ Receptor Antagonists," *Bioorg. Med. Chem. Lett*. (2007) vol. 17, pp. 3504-3507.
Tavares, F. X. et al. "Potent, Selective, and Orally Efficacious Antagonists of Melanin-Concentrating Hormone Receptor 1," *J. Med. Chem*. (2006) vol. 49, No. 24, pp. 7095-7107.
STN Chemical Structure Search Results (dated Jun. 5, 2015; 13 pages).
STN Chemical Structure Search Results (dated May 2, 2014; 10 pages).
STN Chemical Structure Search Results (dated May 2, 2014; 28 pages).
U.S. Appl. No. 15/205,212, Tetrahydro[1,8]Naphthyridine Sulfonamide and Related Compounds for Use as Agonists of RORgamma and the Treatment of Disease, filed Jul. 8, 2016.
U.S. Appl. No. 14/559,082, Retinoid-Related Orphan Receptor Gamma Modulators for Treatment of Cancer, Autoimmune Disorders, and Inflammatory Disorders and Use in Diagnostic Methods, filed Dec. 3, 2014.
U.S. Appl. No. 15/120,798, Adoptive Cellular Therapy Using an Agonist of Retinoic Acid Receptor-Related Orphan Receptor Gamma & Related Therapeutic Methods, filed Aug. 23, 2016.
U.S. Appl. No. 15/308,736, Tetrahydroquinoline Sulfonamide and Related Compounds for Use as Agonists of RORy and the Treatment of Disease, filed Nov. 3, 2016.

\* cited by examiner

BENZENESULFONAMIDO AND RELATED COMPOUNDS FOR USE AS AGONISTS OF RORγ AND THE TREATMENT OF DISEASE

CROSS-REFERENCE TO RELATED APPLICATIONS

This application is the national stage of International (PCT) Patent Application Serial No. PCT/US2015/029167 filed May 5, 2015 which claims the benefit of and priority to United States Provisional Patent Application serial number 61/988,707, filed May 5, 2014, the contents of each of which are hereby incorporated by reference.

FIELD OF THE INVENTION

The invention provides benzenesulfonamido and related compounds, methods of promoting RORγ activity and/or increasing the amount of IL-17 in a subject, and therapeutic uses of the benzenesulfonamido and related compounds, such as treating medical conditions in which activation of immune response is beneficial.

BACKGROUND

Retinoid-related orphan receptors (ROR) are reported to have an important role in numerous biological processes. See, for example, Dussault et al. in *Mech. Dev.* (1998) vol. 70, 147-153; and Andre et al. in *EMBO J.* (1998) vol. 17, 3867-3877. Scientific investigations relating to each of retinoid-related orphan receptors RORα, RORβ, and RORγ have been described in the literature. See, for example, Hirose et al. in *Biochem. Biophys. Res. Commun.* (1994) vol. 205, 1976-1983; Giguere et al. in *Genes. Dev.* (1994) vol. 8, 538-553; Medvedev et al. in *Gene* (1996) vol. 181, 199-206; Ortiz et al. in *Mol. Endocrinol.* (1995) vol. 9, 1679-1691; and A. M. Jetten in *Curr Drug Targets Inflamm Allergy* (2004) vol. 3, 395-412). Continuing research in this field is spurred by the promise of developing new therapeutic agents to treat medical disorders associated with retinoid-related orphan receptor activity.

RORγ has been reported to be expressed in high concentration in various tissues, such as thymus, kidney, liver, muscle, and certain fat tissue. See, for example, Hirose et al. in *Biochem. Biophys. Res. Commun.* (1994) vol. 205, 1976-1983; Medvedev et al. in *Gene* (1996) vol. 181, 199-206; Ortiz et al. in *Mol. Endocrinol.* (1995) vol. 9, 1679-1691; and He et al. in *Immunity* (1998) vol. 9, 797-806. Two isoforms of RORγ have been identified and are referred to as γ1 and γ2 (also referred to as RORγt). See, for example, He et al. in *Immunity* (1998) vol. 9, 797-806. Expression of the γ2 isoform has been reported to appear in, for example, double-positive thymocytes. See, for example, He et al. in *Immunity* (1998) vol. 9, 797-806; and Villey et al. in *Eur. J. Immunol.* (1999) vol. 29, 4072-4080. RORγt plays a critical role in regulating differentiation of Th17 cells, a subset of T helper lymphocytes. See, for example, Ivanov et al. in *Cell* (2006) vol. 126, 1121-1133. Th17 cells are important for recruiting tumor-killing cytotoxic CD8+ T cells and natural killer cells into the tumor microenvironment. The level of Th17 cells correlated positively with patient survival or slower disease progression in certain cancers. See, for example, Kryczek et al. in *Blood* (2009) vol 114, 1141-1149; and Sfanos et al. in *Clinical Cancer Research* (2008) vol 14, 3254-3261. Compounds capable of enhancing RORγt activity are thus contemplated to provide a therapeutic benefit in the treatment of cancer.

Cancer continues to be a significant health problem despite the substantial research efforts and scientific advances reported in the literature for treating this disease. Some of the most frequently diagnosed cancers include prostate cancer, breast cancer, and lung cancer. Prostate cancer is the most common form of cancer in men. Breast cancer remains a leading cause of death in women. Current treatment options for these cancers are not effective for all patients and/or can have substantial adverse side effects.

Accordingly, a need exists for improved treatments for cancer. The present invention addresses this need and provides other related advantages.

SUMMARY

The invention provides benzenesulfonamido and related compounds, pharmaceutical compositions, methods of promoting RORγ activity and/or increasing the amount of IL-17 in a subject, and methods of treating various medical disorders using such compounds. In particular, one aspect of the invention provides a collection of benzenesulfonamido compounds, such as a compound represented by Formula I:

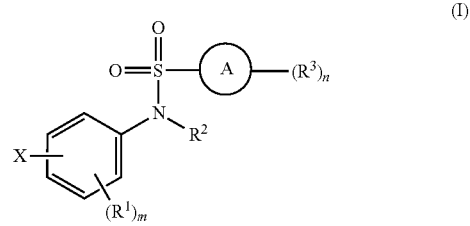

or a pharmaceutically acceptable salt thereof; wherein the variables are as defined in the detailed description. Another aspect of the invention provides a collection of benzylsulfonyl compounds, such as a compound represented by Formula II:

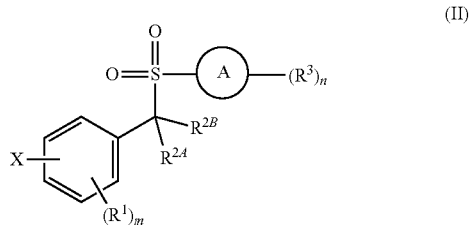

or a pharmaceutically acceptable salt thereof; wherein the variables are as defined in the detailed description. Further description of additional collections of benzenesulfonamido and benzylsulfonyl compounds (collectively "benzenesulfonamido and related compounds") are described in the detailed description.

Another aspect of the invention provides a method of treating a subject suffering from a medical disorder. The method comprises administering to the subject a therapeutically effective amount of one or more benzenesulfonamido or related compounds described herein, e.g., a compound of Formula I, I-A, I-B, II, II-A, or II-B. A large number of disorders can be treated using the benzenesulfonamido and related compounds described herein. For example, the compounds described herein can be used to treat cancer, a bacterial infection, a fungal infection, or an immune deficiency disorder.

Another aspect of the invention provides a method of promoting the activity of RORγ. The method comprises exposing a RORγ to an effective amount of one or more benzenesulfonamido or related compounds described herein, e.g., a compound of Formula I, I-A, I-B, II, II-A, or II-B, or a pharmaceutical composition described herein.

Another aspect of the invention provides a method of increasing the amount of IL-17 in a subject. The method comprises administering to a subject an effective amount of one or more benzenesulfonamido or related compounds described herein, e.g., a compound of Formula I, I-A, I-B, II, II-A, or II-B, or a pharmaceutical composition described herein, to increase the amount of IL-17 in the subject.

DETAILED DESCRIPTION

The invention provides benzenesulfonamido and related compounds, pharmaceutical compositions, methods of promoting RORγ activity and/or increasing the amount of IL-17 in a subject, and therapeutic uses of the benzenesulfonamido and related compounds. The practice of the present invention employs, unless otherwise indicated, conventional techniques of organic chemistry, pharmacology, molecular biology (including recombinant techniques), cell biology, biochemistry, and immunology. Such techniques are explained in the literature, such as in "Comprehensive Organic Synthesis" (B. M. Trost & I. Fleming, eds., 1991-1992); "Handbook of experimental immunology" (D. M. Weir & C. C. Blackwell, eds.); "Current protocols in molecular biology" (F. M. Ausubel et al., eds., 1987, and periodic updates); and "Current protocols in immunology" (J. E. Coligan et al., eds., 1991), each of which is herein incorporated by reference in its entirety.

Various aspects of the invention are set forth below in sections; however, aspects of the invention described in one particular section are not to be limited to any particular section. Further, when a variable is not accompanied by a definition, the previous definition of the variable controls.

Definitions

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name, and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "—O-alkyl" etc.

The term "alkyl" refers to a saturated straight or branched hydrocarbon, such as a straight or branched group of 1-12, 1-10, or 1-6 carbon atoms, referred to herein as $C_1$-$C_{12}$ alkyl, $C_1$-$C_{10}$ alkyl, and $C_1$-$C_6$alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "alkylene" refers to a diradical of an alkyl group. Exemplary alkylene groups include —$CH_2$—, —$CH_2CH_2$—, and —$CH_2C(H)(CH_3)CH_2$—.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "$C_3$-$C_6$ cycloalkyl," derived from a cycloalkane. Exemplary cycloalkyl groups include cyclohexyl, cyclopentyl, cyclobutyl, and cyclopropyl.

The term "cycloalkylene" refers to a diradical of a cycloalkyl group. Exemplary cycloalkylene groups include

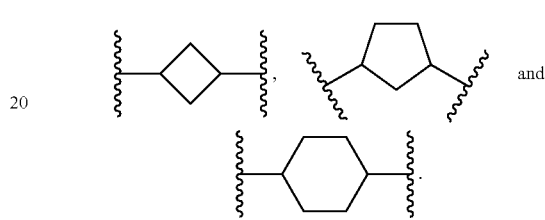

The term "haloalkyl" refers to an alkyl group that is substituted with at least one halogen. Exemplary haloalkyl groups include —$CH_2F$, —$CHF_2$, —$CF_3$, —$CH_2CF_3$, —$CF_2CF_3$, and the like.

The term "aralkyl" refers to an alkyl group substituted with an aryl group. Exemplary aralkyl groups include

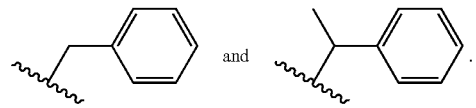

The term "heteroaralkyl" refers to an alkyl group substituted with a heteroaryl group.

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to a carbocyclic aromatic group. Representative aryl groups include phenyl, naphthyl, anthracenyl, and the like. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —$CO_2$alkyl, carbonyl, carboxyl, alkylthio, sulfonyl, sulfonamido, sulfonamide, ketone, aldehyde, ester, heterocyclyl, aryl or heteroaryl moieties, —$CF_3$, —CN, or the like. The term "aryl" also includes polycyclic aromatic ring systems having two or more carbocyclic rings in which two or more carbons are common to two adjoining rings (the rings are "fused rings") wherein all of the fused rings are aromatic rings, e.g., in a naphthyl group.

The term "phenylene" refers to a multivalent radical (e.g., a divalent or trivalent radical) of benzene. To illustrate, a divalent valent radical of benzene is illustrated by the formula

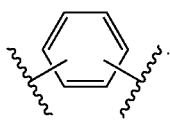

The term "partially unsaturated bicyclic carbocyclyl" refers to a bicyclic carbocyclic group that comprises at least one carbon-carbon double bond between ring carbon atoms and at least one ring in the bicyclic carbocyclic group is not aromatic. Representative examples of a partially unsaturated bicyclic carbocyclyl include, for example:

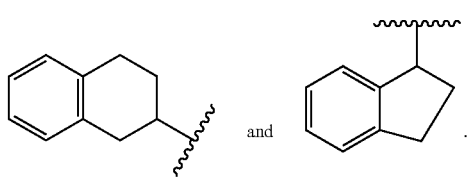 [SMILES: *C1CCc2ccccc2C1 ; *C1CCc2ccccc21]

The term "heteroaryl" is art-recognized and refers to aromatic groups that include at least one ring heteroatom. In certain instances, a heteroaryl group contains 1, 2, 3, or 4 ring heteroatoms (e.g., O, N, and S). Representative examples of heteroaryl groups include pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. Unless specified otherwise, the heteroaryl ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. The term "heteroaryl" also includes polycyclic aromatic ring systems having two or more rings in which two or more ring atoms are common to two adjoining rings (the rings are "fused rings") wherein all of the fused rings are heteroaromatic, e.g., in a naphthyridinyl group. In certain embodiments, the heteroaryl is a 5-6 membered monocylic ring or a 9-10 membered bicyclic ring.

The term "heteroarylene" refers to a multi-valent (e.g., di-valent or trivalent) aromatic group that comprises at least one ring heteroatom. An exemplary "heteroarylene" is pyridinylene, which is a multi-valent radical of pyridine. For example, a divalent radical of pyridine is illustrated by the formula

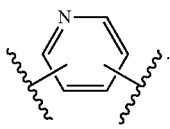

In certain embodiments, the "heteroarylene" is a divalant, 5-6 membered heteroaromatic group containing 1, 2, or 3 ring heteroatoms (e.g., O, N, or S).

The terms ortho, meta, and para are art-recognized and refer to 1,2-, 1,3- and 1,4-disubstituted benzenes, respectively. For example, the names 1,2-dimethylbenzene and ortho-dimethylbenzene are synonymous.

As used herein, the terms "heterocyclic" and "heterocyclyl" represent, for example, an aromatic or nonaromatic ring (e.g., a monocyclic or bicyclic ring) containing one or more heteroatoms. The heteroatoms can be the same or different from each other. Examples of heteroatoms include, but are not limited to nitrogen, oxygen and sulfur. Aromatic and nonaromatic heterocyclic rings are well-known in the art. Some nonlimiting examples of aromatic heterocyclic rings include, but are not limited to, pyridine, pyrimidine, indole, purine, quinoline and isoquinoline. Nonlimiting examples of nonaromatic heterocyclic compounds include, but are not limited to, piperidine, piperazine, morpholine, pyrrolidine and pyrazolidine. Examples of oxygen containing heterocyclic rings include, but are not limited to, furan, oxirane, 2H-pyran, 4H-pyran, 2H-chromene, benzofuran, and 2,3-dihydrobenzo[b][1,4]dioxine. Examples of sulfur-containing heterocyclic rings include, but are not limited to, thiophene, benzothiophene, and parathiazine. Examples of nitrogen containing rings include, but are not limited to, pyrrole, pyrrolidine, pyrazole, pyrazolidine, imidazole, imidazoline, imidazolidine, pyridine, piperidine, pyrazine, piperazine, pyrimidine, indole, purine, benzimidazole, quinoline, isoquinoline, triazole, and triazine. Examples of heterocyclic rings containing two different heteroatoms include, but are not limited to, phenothiazine, morpholine, parathiazine, oxazine, oxazole, thiazine, and thiazole. The heterocyclic ring is optionally further substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the heterocyclyl group is a 3-7 membered ring that, unless specified otherwise, is substituted or unsubstituted.

The term "heterocycloalkyl" refers to a saturated heterocyclyl group having, for example, 3-7 ring atoms (e.g., O, N, or S).

The term "heterocycloalkylene" refers to a multi-valent (e.g., di-valent or trivalent) saturated heterocyclyl group having, for example, 3-7 ring atoms. An exemplary "heterocycloalkylene" is piperidinylene, which is a multi-valent radical of piperidine. In certain embodiments, the "heterocycloalkylene" is a divalant, 5-6 membered saturated heterocyclyl containing 1 or 2 ring heteroatoms (e.g., O, N, or S).

The term "partially unsaturated bicyclic heterocyclyl" refers to a bicyclic heterocyclic group that comprises at least one double bond between ring atoms and at least one ring in the bicyclic heterocyclic group is not aromatic. Representative examples of a partially unsaturated bicyclic heterocyclyl include, for example:

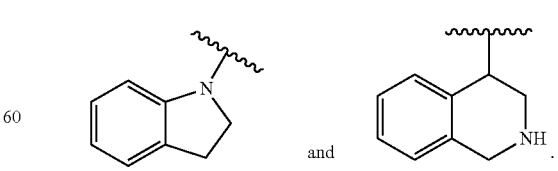

The term "partially unsaturated bicyclic oxo-heterocyclyl" refers to a bicyclic heterocyclic group that comprises at least one double bond between ring atoms, one oxo substituent, and at least one ring in the bicyclic heterocyclic group is not aromatic. Representative examples of a partially unsaturated bicyclic oxo-heterocyclyl include, for example:

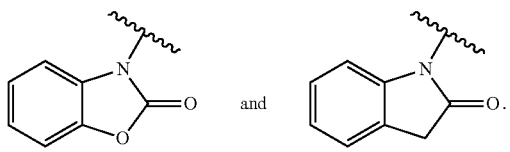 [SMILES: *n1c(=O)oc2ccccc21 ; *N1C(=O)Cc2ccccc21] and

The terms "amine" and "amino" are art-recognized and refer to both unsubstituted and substituted amines, e.g., a moiety that may be represented by the general formulas:

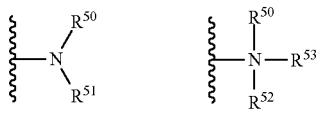

wherein $R^{50}$, $R^{51}$, $R^{52}$ and $R^{53}$ each independently represent a hydrogen, an alkyl, an alkenyl, $-(CH_2)_m-R^{61}$, or $R^{50}$ and $R^{51}$, taken together with the N atom to which they are attached complete a heterocycle having from 4 to 8 atoms in the ring structure; $R^{61}$ represents an aryl, a cycloalkyl, a cycloalkenyl, a heterocycle or a polycycle; and m is zero or an integer in the range of 1 to 8. In certain embodiments, only one of $R^{50}$ or $R^{51}$ may be a carbonyl, e.g., $R^{50}$, $R^{51}$ and the nitrogen together do not form an imide. In other embodiments, $R^{50}$ and $R^{51}$ (and optionally $R^{52}$) each independently represent a hydrogen, an alkyl, an alkenyl, or $-(CH_2)_m-R^{61}$.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and $-O-(CH_2)_m-R^{61}$, where m and $R^{61}$ are described above.

The term "oxo" is art-recognized and refers to a "=O" substituent. For example, a cyclopentane susbsituted with an oxo group is cyclopentanone.

The symbol "⌇" indicates a point of attachment.

The term "substituted" means that one or more hydrogens on the atoms of the designated group are replaced with a selection from the indicated group, provided that the atoms' normal valencies under the existing circumstances are not exceeded, and that the substitution results in a stable compound. Combinations of substituents and/or variables are permissible only if such combinations result in stable compounds. The terms stable compound' or "stable structure" refer to a compound that is sufficiently robust to survive isolation to a useful degree of purity from a reaction mixture, and formulation into an efficacious therapeutic agent.

When any substituent or variable occurs more than one time in any constituent or the compound of the invention, its definition on each occurrence is independent of its definition at every other occurrence, unless otherwise indicated.

It should also be noted that any carbon as well as heteroatom with unsatisfied valences in the text, Schemes, Examples and Tables herein is assumed to have the sufficient number of hydrogen atom(s) to satisfy the valences.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Nonlimiting examples of suitable solvates include ethanolates, methanolates, and the like. "Hydrate" is a solvate wherein the solvent molecule is $H_2O$.

Certain compounds contained in compositions of the present invention may exist in particular geometric or stereoisomeric forms. Further, certain compounds described herein may be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. The compounds may contain one or more stereogenic centers. For example, asymmetric carbon atoms may be present in a substituent such as an alkyl group. All such isomers, as well as mixtures thereof, are intended to be included in this invention, such as, for example, racemic mixtures, single enantiomers, diastereomeric mixtures and individual diastereomers. Additional asymmetric centers may be present depending upon the nature of the various substituents on the molecule. Each such asymmetric center will independently produce two optical isomers, and it is intended that all of the possible optical isomers, diastereomers in mixtures, and pure or partially purified compounds are included within the ambit of this invention.

Diastereomeric mixtures can be separated into their individual diastereomers on the basis of their physical chemical differences by methods known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Alternatively, a particular enantiomer of a compound of the present invention may be prepared by asymmetric synthesis. Still further, where the molecule contains a basic functional group (such as amino) or an acidic functional group (such as carboxylic acid) diastereomeric salts are formed with an appropriate optically-active acid or base, followed by resolution of the diastereomers thus formed by fractional crystallization or chromatographic means known in the art, and subsequent recovery of the pure enantiomers.

Individual stereoisomers of the compounds of the invention may, for example, be substantially free of other isomers, or may be admixed, for example, as racemates or with all other, or other selected, stereoisomers. Chiral center(s) in a compound of the present invention can have the S or R configuration as defined by the IUPAC 1974 Recommendations. Further, to the extent a compound described herein may exist as a atropisomer (e.g., substituted biaryls), all forms of such atropisomer are considered part of this invention.

As used herein, the terms "subject" and "patient" are used interchangeable and refer to organisms to be treated by the methods of the present invention. Such organisms preferably include, but are not limited to, mammals (e.g., murines, simians, equines, bovines, porcines, canines, felines, and the like), and most preferably includes humans.

The term "$EC_{50}$" is art-recognized and refers to the concentration of a compound that is required to achieve 50% of the maximum possible activation of the target.

As used herein, the term "effective amount" refers to the amount of a compound sufficient to effect beneficial or desired results (e.g., a therapeutic, ameliorative, inhibitory or preventative result). An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, Pa. [1975].

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate (also known as toluenesulfonate), undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. Further examples of salts include, but are not limited to: ascorbate, borate, nitrate, phosphate, salicylate, and sulfate. Further, acids which are generally considered suitable for the formation of pharmaceutically useful salts from basic pharmaceutical compounds are discussed, for example, by P. Stahl et al., Camille G. (eds.) *Handbook of Pharmaceutical Salts. Properties, Selection and Use*. (2002) Zurich: Wiley-VCH; S. Berge et al., *Journal of Pharmaceutical Sciences* (1977) 66(1), 1-19; P. Gould, *International J. of Pharmaceutics* (1986) 33, 201-217; Anderson et al., *The Practice of Medicinal Chemistry* (1996), Academic Press, New York; and in *The Orange Book* (Food & Drug Administration, Washington, D.C. on their website). These disclosures are incorporated herein by reference.

Additional exemplary basic salts include, but are not limited to: ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

In addition, when a compound of the invention contains both a basic moiety (such as, but not limited to, a pyridine or imidazole) and an acidic moiety (such as, but not limited to, a carboxylic acid) zwitterions ("inner salts") may be formed. Such acidic and basic salts used within the scope of the invention are pharmaceutically acceptable (i.e., non-toxic, physiologically acceptable) salts. Such salts of the compounds of the invention may be formed, for example, by reacting a compound of the invention with an amount of acid or base, such as an equivalent amount, in a medium such as one in which the salt precipitates or in an aqueous medium followed by lyophilization.

The present invention includes the compounds of the invention in all their isolated forms (such as any solvates, hydrates, stereoisomers, and tautomers thereof). Further, the invention includes compounds in which one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques known to those skilled in the art or by processes analogous to those described in the Schemes and Examples herein using appropriate isotopically-enriched reagents and/or intermediates.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

The terms "a" and "an" as used herein mean "one or more" and include the plural unless the context is inappropriate.

The abbreviation "THF" is art-recognized and refers to tetrahydrofuran. The abbreviation "DCM" is art-recognized and refers to dichloromethane. The abbreviation "DMF" is art-recognized and refers to dimethylformamide. The abbreviation "DMA" is art-recognized and refers to dimethylacetamide. The abbreviation "EDTA" is art-recognized and refers to ethylenediaminetetraacetic acid. The abbreviation "TFA" is art-recognized and refers to trifluoroacetic acid.

As a general matter, compositions specifying a percentage are by weight unless otherwise specified.

I. Benzenesulfonamido and Related Compounds

The invention provides benzenesulfonamido compounds and benzylsulfone compounds (collectively "benzenesulfonamido and related compounds"). Exemplary compounds are described in the sections below, along with exemplary procedures for making the compounds. Additional exemplary compounds and synthetic procedures are described in the Examples.

Part I: Benzenesulfonamido Compounds

One aspect of the invention provides a compound represented by Formula I:

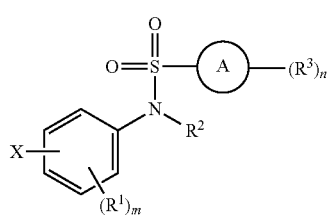

(I)

or a pharmaceutically acceptable salt thereof; wherein:

A is phenylene, 5-6 membered heteroarylene, or $C_{3-6}$heterocycloalkylene;

$R^1$ represents independently for each occurrence halogen, $C_{1-6}$alkyl, $C_{1-6}$haloalkyl, or $C_{3-6}$cycloalkyl;

$R^2$ is $C_{1-6}$alkyl, $C_{3-6}$cycloalkyl, or $C_{3-6}$heterocyclyl, each of which is optionally substituted with 1, 2, or 3 substituents independently selected from the group consisting of —$CO_2R^4$, halogen, hydroxyl, $C_{1-6}$alkoxy, $C_{1-6}$haloalkoxy, cyano, —$N(R^4)(R^5)$, —$N(R^4)C(O)R^5$, —$SO_2R^6$, and —$C(O)N(R^4)(R^5)$;

$R^3$ represents independently for each occurrence hydrogen, $C_{1-6}$haloalkyl, halogen, $C_{1-6}$alkyl, $C_{3-6}$cycloalkyl, $C_{1-6}$alkoxy, $C_{1-6}$haloalkoxy, or hydroxyl; or two vicinal occurrences of $R^3$ are taken together with intervening atoms to form a 4-6 membered ring;

$R^4$ and $R^5$ each represent independently for each occurrence hydrogen, $C_{1-6}$alkyl, or $C_{3-6}$cycloalkyl; or an occurrence of $R^4$ and $R^5$ attached to the same nitrogen atom are taken together with the nitrogen atom to which they are attached to form a 3-7 membered heterocyclic ring;

$R^6$ represents independently for each occurrence $C_{1-6}$alkyl or $C_{3-6}$cycloalkyl;

X is one of the following:

(i) —O-aralkyl, —O-heteroaralkyl, —O-phenyl, —O-heteroaryl, —O-(partially unsaturated bicyclic carbocyclyl), —O—($C_{1-6}$alkylene)-($C_{3-6}$cycloalkyl), —O—($C_{3-6}$cycloalkyl), —N($R^4$)-aralkyl, —N($R^4$)-phenyl, —N($R^4$)-(partially unsaturated bicyclic carbocyclyl), or —N($R^4$)—($C_{1-6}$alkylene)-($C_{3-6}$cycloalkyl), each of which is optionally substituted with 1, 2, or 3 substituents independently selected from the group consisting of halogen, $C_{1-6}$haloalkyl, $C_{1-6}$alkyl, $C_{3-6}$cycloalkyl, $C_{1-6}$alkoxy, $C_{1-6}$haloalkoxy, hydroxyl, and cyano;

(ii) —($C_{2-6}$alkenylene)-phenyl, —($C_{2-6}$alkenylene)-heteroaryl, —($C_{1-6}$alkylene)-phenyl, —($C_{1-6}$alkylene)-heteroaryl, —($C_{1-6}$alkylene)-(partially unsaturated bicyclic heterocyclyl), —($C_{1-6}$alkylene)-(partially unsaturated bicyclic oxo-heterocyclyl), -(5-6 membered heterocycloalkylene)-phenyl, or —($C_{3-6}$cycloalkylene)-phenyl, each of which is optionally substituted with 1, 2, or 3 substituents independently selected from the group consisting of halogen, $C_{1-6}$haloalkyl, $C_{1-6}$alkyl, $C_{3-6}$cycloalkyl, $C_{1-6}$alkoxy, $C_{1-6}$haloalkoxy, hydroxyl, and cyano; or (iii) —($C_{1-6}$alkylene)-$Z^1$ or —($C_{2-6}$alkenylene)-$Z^1$, wherein $Z^1$ is —O-aralkyl, —O-heteroaralkyl, —O-phenyl, —O-heteroaryl, —O-(partially unsaturated bicyclic carbocyclyl), —O—($C_{1-6}$alkylene)-($C_{3-6}$cycloalkyl), —O—($C_{3-6}$cycloalkyl), —N($R^4$)-aralkyl, —N($R^4$)-phenyl, —N($R^4$)-(partially unsaturated bicyclic carbocyclyl), —N($R^4$)—($C_{1-6}$alkylene)-($C_{3-6}$cycloalkyl), or —N($R^4$)—($C_{3-6}$cycloalkyl), each of which is optionally substituted with 1, 2, or 3 substituents independently selected from the group consisting of halogen, $C_{1-6}$haloalkyl, $C_{1-6}$alkyl, $C_{3-6}$cycloalkyl, $C_{1-6}$alkoxy, $C_{1-6}$haloalkoxy, hydroxyl, and cyano;

m is 0, 1, or 2; and n is 1, 2, or 3.

In certain embodiments, A is phenylene or 5-6 membered heteroarylene.

In certain embodiments, $R^1$ represents independently for each occurrence halogen or $C_{1-6}$alkyl.

In certain embodiments, X is further selected from an 8-10 membered, bicyclic partially saturated carbocyclyl which is optionally substituted with 1, 2, or 3 substituents independently selected from the group consisting of halogen, $C_{1-6}$haloalkyl, $C_{1-6}$alkyl, $C_{3-6}$cycloalkyl, $C_{1-6}$alkoxy, $C_{1-6}$haloalkoxy, —S—($C_{1-6}$alkyl), hydroxyl, and cyano.

The definitions of variables in Formula I above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii), e.g., such as where A is phenylene and $R^3$ is selected from the group consisting of $C_{1-6}$haloalkyl, halogen, and $C_{1-6}$alkyl.

Another aspect of the invention provides a compound represented by Formula I-A:

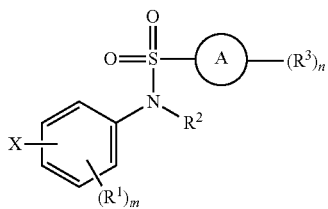

(I-A)

or a pharmaceutically acceptable salt thereof; wherein:

A is phenylene or a 5-6 membered heteroarylene;

$R^1$ represents independently for each occurrence halogen, $C_{1-6}$alkyl, or $C_{3-6}$cycloalkyl;

$R^2$ is $C_{1-6}$alkyl or $C_{3-6}$cycloalkyl, each of which is optionally substituted with 1, 2, or 3 substituents independently selected from the group consisting of —$CO_2R^4$, halogen, hydroxyl, $C_{1-6}$alkoxy, $C_{1-6}$haloalkoxy, cyano, —$N(R^4)(R^5)$, and —$N(R^4)C(O)R^5$;

$R^3$ represents independently for each occurrence hydrogen, $C_{1-6}$haloalkyl, halogen, $C_{1-6}$alkyl, $C_{1-6}$alkoxy, $C_{1-6}$haloalkoxy, or hydroxyl; or two vicinal occurrences of $R^3$ are taken together with intervening atoms to form a 4-6 membered ring;

$R^4$ and $R^5$ each represent independently for each occurrence hydrogen, $C_{1-6}$alkyl, or $C_{3-6}$cycloalkyl; or an occurrence of $R^4$ and $R^5$ attached to the same nitrogen atom are taken together with the nitrogen atom to which they are attached to form a 3-7 membered heterocyclic ring;

X is one of the following:
(i) —O-aralkyl, —O-heteroaralkyl, —O-phenyl, —O-heteroaryl, —O-(partially unsaturated bicyclic carbocyclyl), —O—($C_{1-6}$alkylene)-($C_{3-6}$cycloalkyl), —$N(R^4)$-aralkyl, —$N(R^4)$-phenyl, —$N(R^4)$-(partially unsaturated bicyclic carbocyclyl), or —$N(R^4)$—($C_{1-6}$alkylene)-($C_{3-6}$cycloalkyl), each of which is optionally substituted with 1, 2, or 3 substituents independently selected from the group consisting of halogen, $C_{1-6}$haloalkyl, $C_{1-6}$alkyl, $C_{3-6}$cycloalkyl, $C_{1-6}$alkoxy, and $C_{1-6}$haloalkoxy;
(ii) —($C_{2-6}$alkenylene)-phenyl, —($C_{2-6}$alkenylene)-heteroaryl, —($C_{1-6}$alkylene)-phenyl, —($C_{1-6}$alkylene)-heteroaryl, —($C_{1-6}$alkylene)-(partially unsaturated bicyclic heterocyclyl), —($C_{1-6}$alkylene)-(partially unsaturated bicyclic oxo-heterocyclyl), or -(5-6 membered heterocycloalkylene)-phenyl, each of which is optionally substituted with 1, 2, or 3 substituents independently selected from the group consisting of halogen, $C_{1-6}$haloalkyl, $C_{1-6}$alkyl, $C_{3-6}$cycloalkyl, $C_{1-6}$alkoxy, and $C_{1-6}$haloalkoxy; or
(iii) —($C_{1-6}$alkylene)-$Z^1$ or —($C_{2-6}$alkenylene)-$Z^1$, wherein $Z^1$ is —O-aralkyl, —O-heteroaralkyl, —O-phenyl, —O-heteroaryl, —O-(partially unsaturated bicyclic carbocyclyl), —O—($C_{1-6}$alkylene)-($C_{3-6}$cycloalkyl), —O—($C_{3-6}$cycloalkyl), —$N(R^4)$-aralkyl, —$N(R^4)$-phenyl, —$N(R^4)$-(partially unsaturated bicyclic carbocyclyl), or —$N(R^4)$—($C_{1-6}$alkylene)-($C_{3-6}$cycloalkyl), each of which is optionally substituted with 1, 2, or 3 substituents independently selected from the group consisting of halogen, $C_{1-6}$haloalkyl, $C_{1-6}$alkyl, $C_{3-6}$cycloalkyl, $C_{1-6}$alkoxy, and $C_{1-6}$haloalkoxy;

m is 0, 1, or 2; and n is 1, 2, or 3.

In certain embodiments, A is phenylene. In certain other embodiments, A is a 5-6 membered heteroarylene. In yet other embodiments, -A-$(R^3)_n$ is one of the following:

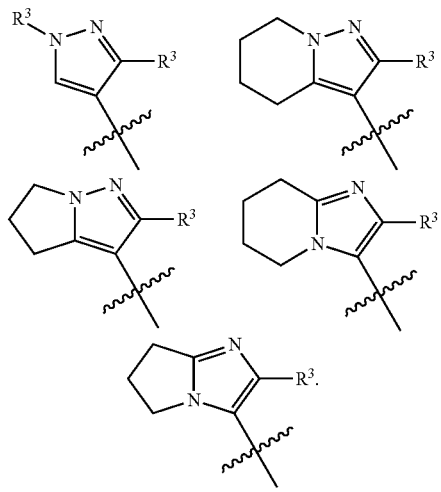

In certain embodiments, $R^1$ represents independently for each occurrence halogen or methyl.

In certain embodiments, $R^2$ is $C_{1-6}$alkyl optionally substituted with 1, 2, or 3 substituents independently selected from the group consisting of —$CO_2R^4$, halogen, hydroxyl, and $C_{1-6}$alkoxy, and —$N(R^4)C(O)R^5$. In certain other embodiments, $R^2$ is $C_{1-6}$alkyl optionally substituted with 1, 2, or 3 substituents independently selected from the group consisting of —$CO_2R^4$, halogen, hydroxyl, and $C_{1-6}$alkoxy. In certain other embodiments, $R^2$ is $C_{1-6}$alkyl optionally substituted with 1 substituent selected from the group consisting of —$CO_2R^4$, halogen, hydroxyl, and $C_{1-6}$alkoxy. In certain other embodiments, $R^2$ is $C_{1-6}$alkyl substituted with —$CO_2R^4$. In certain other embodiments, $R^2$ is ethyl or propyl.

In certain embodiments, n is 1. In certain other embodiments, n is 1 or 2.

In certain embodiments, $R^3$ is $C_{1-6}$haloalkyl. In certain other embodiments, $R^3$ is trifluoromethyl. In yet other embodiments, $R^3$ represents independently for each occurrence $C_{1-6}$haloalkyl, halogen, $C_{1-6}$alkyl, or $C_{1-6}$alkoxy.

In certain embodiments, X is —O-aralkyl, —O-heteroaralkyl, —O-phenyl, —O-heteroaryl, —O-(partially unsaturated bicyclic carbocyclyl), —O—($C_{1-6}$alkylene)-($C_{3-6}$cycloalkyl), —$N(R^4)$-aralkyl, —$N(R^4)$-phenyl, —$N(R^4)$-(partially unsaturated bicyclic carbocyclyl), or —$N(R^4)$—($C_{1-6}$alkylene)-($C_{3-6}$cycloalkyl), each of which is optionally substituted with 1, 2, or 3 substituents independently selected from the group consisting of halogen, $C_{1-6}$haloalkyl, $C_{1-6}$alkyl, $C_{3-6}$cycloalkyl, $C_{1-6}$alkoxy, and $C_{1-6}$haloalkoxy. In certain other embodiments, X is —O-aralkyl, —O-phenyl, —O-(partially unsaturated bicyclic carbocyclyl), —O—($C_{1-6}$alkylene)-($C_{3-6}$cycloalkyl), —$N(R^4)$-aralkyl, —$N(R^4)$-phenyl, —$N(R^4)$-(partially unsaturated bicyclic carbocyclyl), or —$N(R^4)$—($C_{1-6}$alkylene)-($C_{3-6}$cycloalkyl), each of which is optionally substituted with 1, 2, or 3 substituents independently selected from the group consisting of halogen, $C_{1-6}$haloalkyl, $C_{1-6}$alkyl, $C_{3-6}$cycloalkyl, $C_{1-6}$alkoxy, and $C_{1-6}$haloalkoxy. In certain other embodiments, X is —O-aralkyl, —O-(partially unsaturated bicyclic carbocyclyl), or —O—($C_{1-6}$alkylene)-($C_{3-6}$cycloalkyl), each of which is optionally substituted with 1, 2, or 3 substituents independently selected from the group consisting of halogen, $C_{1-6}$haloalkyl, $C_{1-6}$alkyl, $C_{3-6}$cycloalkyl, $C_{1-6}$alkoxy, and $C_{1-6}$haloalkoxy. In certain other embodiments, X is —O-aralkyl or —O-(partially unsaturated bicyclic carbocyclyl), each of which is optionally substituted with 1 or 2 substituents independently selected from the group consisting of halogen and $C_{1-6}$haloalkyl. In certain other embodiments, X is —O-benzyl substituted with 1 or 2 substituents independently selected from the group consisting of chloro, bromo, and fluoro.

In certain embodiments, X is —O—($C_{1-6}$alkylene)-phenyl or —N($R^4$)—($C_{1-6}$alkylene)-phenyl, each of which is substituted with 1, 2, or 3 substituents independently selected from the group consisting of halogen, $C_{1-6}$haloalkyl, $C_{1-6}$alkyl, $C_{3-6}$cycloalkyl, $C_{1-6}$alkoxy, and $C_{1-6}$haloalkoxy, where at least one substituent is present at the ortho position on the phenyl group in variable X.

In certain embodiments, X is —($C_{2-6}$alkenylene)-phenyl, —($C_{2-6}$alkenylene)-heteroaryl, —($C_{1-6}$alkylene)-phenyl, —($C_{1-6}$alkylene)-heteroaryl, —($C_{1-6}$alkylene)-(partially unsaturated bicyclic heterocyclyl), —($C_{1-6}$alkylene)-(partially unsaturated bicyclic oxo-heterocyclyl), or -(5-6 membered heterocycloalkylene)-phenyl, each of which is optionally substituted with 1, 2, or 3 substituents independently selected from the group consisting of halogen, $C_{1-6}$haloalkyl, $C_{1-6}$alkyl, $C_{3-6}$cycloalkyl, $C_{1-6}$alkoxy, and $C_{1-6}$haloalkoxy. In certain other embodiments, X is —($C_{2-6}$alkenylene)-phenyl or —($C_{1-6}$alkylene)-phenyl, each of which is optionally substituted with 1, 2, or 3 substituents independently selected from the group consisting of halogen, $C_{1-6}$haloalkyl, $C_{1-6}$alkyl, $C_{3-6}$cycloalkyl, $C_{1-6}$alkoxy, $C_{1-6}$haloalkoxy, hydroxyl, and cyano. In certain other embodiments, X is —($C_{1-6}$alkylene)-heteroaryl, —($C_{1-6}$alkylene)-(partially unsaturated bicyclic heterocyclyl), —($C_{1-6}$alkylene)-(partially unsaturated bicyclic oxo-heterocyclyl), or -(5-6 membered heterocycloalkylene)-phenyl, each of which is optionally substituted with 1, 2, or 3 substituents independently selected from the group consisting of halogen, $C_{1-6}$haloalkyl, $C_{1-6}$alkyl, $C_{3-6}$cycloalkyl, $C_{1-6}$alkoxy, and $C_{1-6}$haloalkoxy.

In certain embodiments, X is —($C_{1-6}$alkylene)-$Z^1$ or —($C_{2-6}$alkenylene)-$Z^1$, wherein $Z^1$ is —O-aralkyl, —O-heteroaralkyl, —O-phenyl, —O-heteroaryl, —O-(partially unsaturated bicyclic carbocyclyl), —O—($C_{1-6}$alkylene)-($C_{3-6}$cycloalkyl), —O—($C_{3-6}$cycloalkyl), —N($R^4$)-aralkyl, —N($R^4$)-phenyl, —N($R^4$)-(partially unsaturated bicyclic carbocyclyl), or —N($R^4$)—($C_{1-6}$alkylene)-($C_{3-6}$cycloalkyl), each of which is optionally substituted with 1, 2, or 3 substituents independently selected from the group consisting of halogen, $C_{1-6}$haloalkyl, $C_{1-6}$alkyl, $C_{3-6}$cycloalkyl, $C_{1-6}$alkoxy, and $C_{1-6}$haloalkoxy. In certain other embodiments, X is —($C_{1-6}$alkylene)-$Z^1$, wherein $Z^1$ is —O-aralkyl, —O-phenyl, —O-(partially unsaturated bicyclic carbocyclyl), —O—($C_{1-6}$alkylene)-($C_{3-6}$cycloalkyl), —O—($C_{3-6}$cycloalkyl), —N($R^4$)-aralkyl, —N($R^4$)-phenyl, —N($R^4$)-(partially unsaturated bicyclic carbocyclyl), or —N($R^4$)—($C_{1-6}$alkylene)-($C_{3-6}$cycloalkyl), each of which is optionally substituted with 1, 2, or 3 substituents independently selected from the group consisting of halogen, $C_{1-6}$haloalkyl, $C_{1-6}$alkyl, $C_{3-6}$cycloalkyl, $C_{1-6}$alkoxy, and $C_{1-6}$haloalkoxy. In certain other embodiments, X is —($C_{1-6}$alkylene)-$Z^1$, wherein $Z^1$ is —O-aralkyl, —N($R^4$)-aralkyl, or —N($R^4$)-phenyl, each of which is optionally substituted with 1, 2, or 3 substituents independently selected from the group consisting of halogen, $C_{1-6}$haloalkyl, and $C_{1-6}$alkyl.

In certain embodiments, X is attached at the meta or para position of the sulfonamido-phenyl group.

In certain embodiments, X is further selected from an 8-10 membered, bicyclic partially saturated carbocyclyl which is optionally substituted with 1, 2, or 3 substituents independently selected from the group consisting of halogen, $C_{1-6}$haloalkyl, $C_{1-6}$alkyl, $C_{3-6}$cycloalkyl, $C_{1-6}$alkoxy, $C_{1-6}$haloalkoxy, —S—($C_{1-6}$alkyl), hydroxyl, and cyano.

In certain embodiments, m is 0. In certain embodiments, m is 1.

The definitions of variables in Formula I-A above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii), e.g., such as where A is phenylene, $R^2$ is $C_{1-6}$alkyl optionally substituted with 1, 2, or 3 substituents independently selected from the group consisting of —$CO_2R^4$, halogen, hydroxyl, $C_{1-6}$alkoxy, $C_{1-6}$haloalkoxy, and —N($R^4$)($R^5$), and $R^3$ is $C_{1-6}$haloalkyl.

Another aspect of the invention provides a compound represented by Formula I-B:

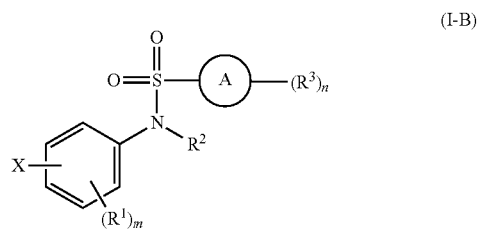

(I-B)

or a pharmaceutically acceptable salt thereof; wherein:

A is phenylene;

$R^1$ represents independently for each occurrence halogen, methyl, ethyl, or cyclopropyl;

$R^2$ is $C_{1-6}$alkyl optionally substituted with 1 or 2 substituents independently selected from the group consisting of —$CO_2R^4$, halogen, hydroxyl, $C_{1-6}$alkoxy, and —N($R^4$)C(O)($C_{1-6}$alkyl);

$R^3$ represents independently for each occurrence $C_{1-3}$haloalkyl, halogen, and $C_{1-3}$ alkyl;

$R^4$ represents independently for each occurrence hydrogen or methyl;

X is attached at the meta or para position of the sulfonamido-phenyl group, and X is one of the following:

(i) —O—($C_{1-6}$alkylene)-phenyl, —O-(partially unsaturated bicyclic carbocyclyl), or —O—($C_{1-6}$alkylene)-($C_{3-6}$cycloalkyl), each of which is optionally substituted with 1, 2, or 3 substituents independently selected from the group consisting of halogen, $C_{1-6}$haloalkyl, $C_{1-6}$alkyl, and $C_{1-6}$alkoxy;

(ii) —($C_{2-6}$alkenylene)-phenyl or —($C_{1-6}$alkylene)-phenyl, each of which is optionally substituted with 1, 2, or 3 substituents independently selected from the group consisting of halogen, $C_{1-6}$haloalkyl, $C_{1-6}$alkyl, $C_{3-6}$cycloalkyl, $C_{1-6}$alkoxy, and $C_{1-6}$haloalkoxy; or (iii) —($C_{1-6}$alkylene)-$Z^1$, wherein $Z^1$ is —O-aralkyl, —O-phenyl, —O-(partially unsaturated bicyclic carbocyclyl), —O—($C_{1-6}$alkylene)-($C_{3-6}$cycloalkyl), —O—($C_{3-6}$cycloalkyl), —N($R^4$)-aralkyl, —N($R^4$)-phenyl, —N($R^4$)-(partially unsaturated bicyclic carbocyclyl), or —N($R^4$)—($C_{1-6}$alkylene)-($C_{3-6}$cycloalkyl), each of which is optionally substituted with 1, 2, or 3 substituents independently selected from the group consisting of halogen, $C_{1-6}$haloalkyl, $C_{1-6}$alkyl, and $C_{1-6}$alkoxy;

m is 0, 1, or 2; and n is 1 or 2.

In certain embodiments, X is —O—(C$_{1-6}$alkylene)-phenyl optionally substituted with 1 or 2 substituents independently selected from the group consisting of halogen, C$_{1-6}$haloalkyl, and C$_{1-6}$alkyl.

The definitions of variables in Formula I-B above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

In certain other embodiments, the compound is a compound defined by one of the following formulae where variables X and Z are as defined in Table 1, or a pharmaceutically acceptable salt thereof

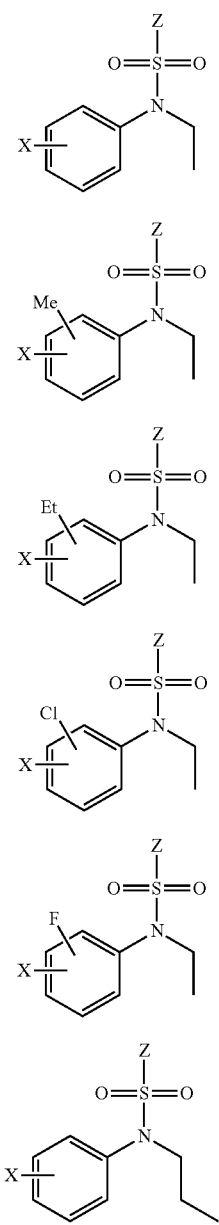

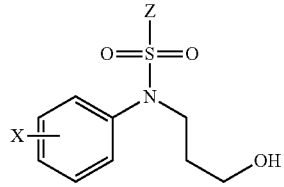

(I-I)

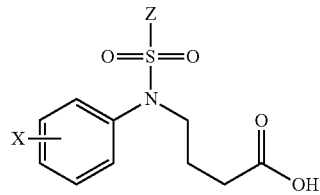

(I-J)

TABLE 1

| No. | X | Z |
|---|---|---|
| I-1 | 2-F, 6-Cl-benzyl-O- | 4-F, 3-MeO-phenyl |
| I-2 | 2-F, 6-Cl-benzyl-O- | 3-Cl-phenyl |
| I-3 | 2-F, 6-Cl-benzyl-O- | 3-cyclopropyl-phenyl |
| I-4 | 2-Cl, 6-F-benzyl-O- | 4-F, 3-CF$_3$-phenyl |
| I-5 | 2-F, 6-Cl-benzyl-O- | 1-ethyl-4-Cl-pyrazol-3-yl |
| I-6 | 2-Cl, 6-F-benzyl-O- | 1-ethyl-3-ethoxy-pyrazol-4-yl |

TABLE 1-continued
| No. | X | Z |
|---|---|---|
| I-7 | 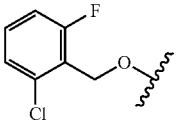 [SMILES: *OCc1c(F)cccc1Cl] | 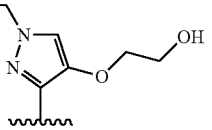 |
| I-8 | 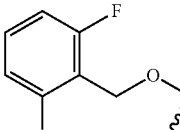 | 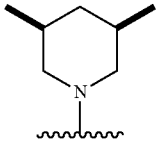 |
| I-9 | 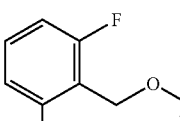 | 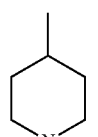 |
| I-10 | 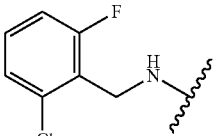 | 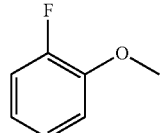 |
| I-11 | 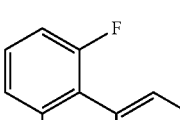 | 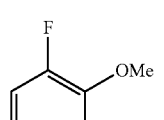 |
| I-12 | 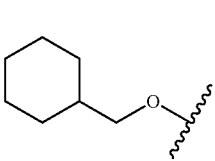 [SMILES: *OCC1CCCCC1] | 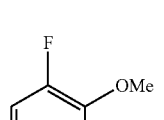 |
| I-13 | 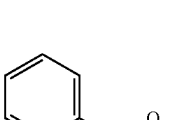 | 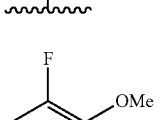 |
| I-14 | 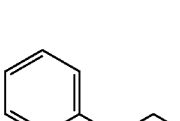 | 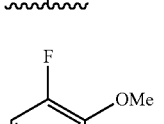 |
| I-15 | 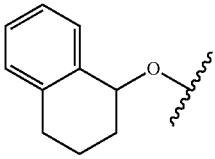 [SMILES: *OC1CCCc2ccccc21] | 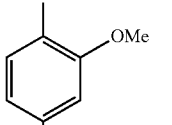 |
| I-16 | 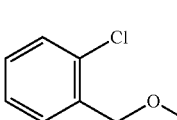 | 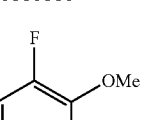 |
| I-17 | 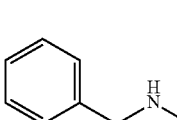 | 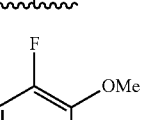 |
| I-18 | 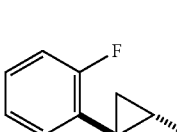 | 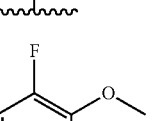 |
| I-19 | 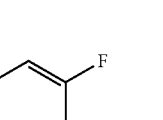 | 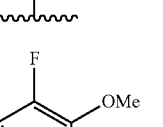 |
| I-20 | 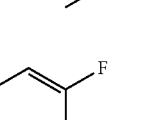 | 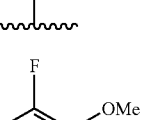 |
| I-21 | 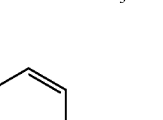 | 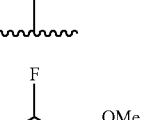 |
| I-22 | 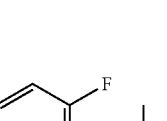 | 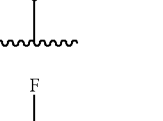 |

TABLE 1-continued
| No. | X | Z |
|---|---|---|
| I-23 | 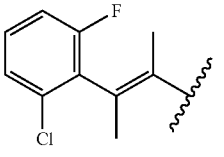 [SMILES: */C(C)=C(\C)c1c(F)cccc1Cl] | 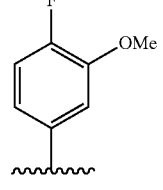 |
| I-24 | 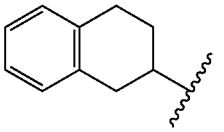 [SMILES: *C1CCc2ccccc2C1] | 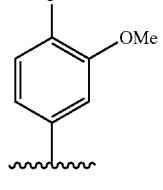 |
| I-25 | 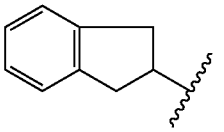 [SMILES: *C1Cc2ccccc2C1] | 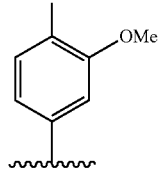 |
| I-26 | 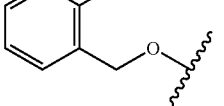 | 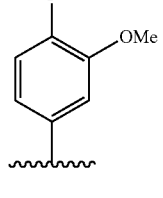 |
| I-27 | 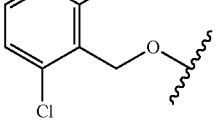 | 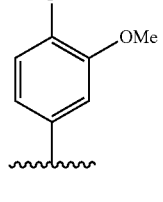 |
| I-28 | 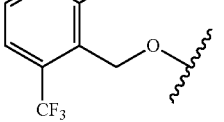 | 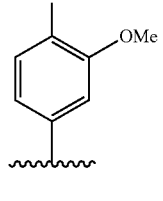 |
| I-29 | 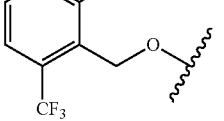 | 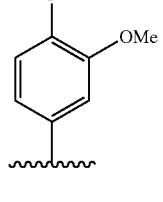 |
| I-30 | 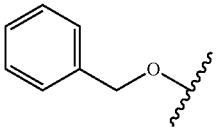 [SMILES: *OCc1ccccc1] | 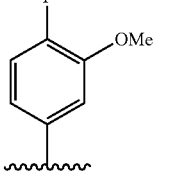 |
| I-31 | 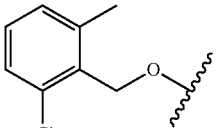 | 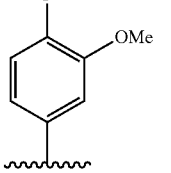 |
| I-32 | 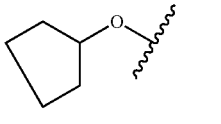 [SMILES: *OC1CCCC1] | 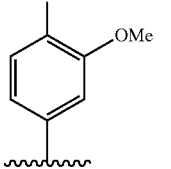 |
| I-33 | 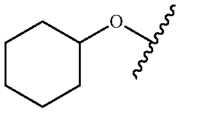 [SMILES: *OC1CCCCC1] | 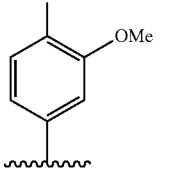 |
| I-34 | 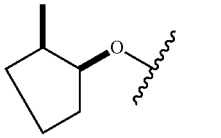 [SMILES: *O[C@H]1CCC[C@H]1C] | 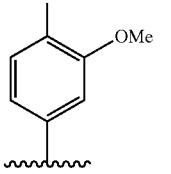 |
| I-35 | 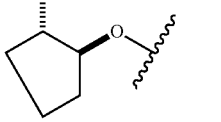 | 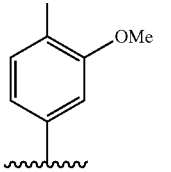 |
| I-36 | 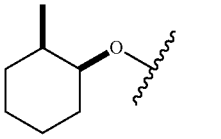 [SMILES: *O[C@H]1CCCC[C@H]1C] | 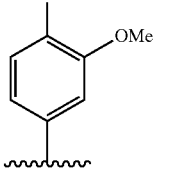 |
| I-37 | 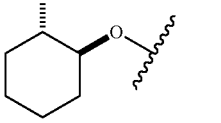 | 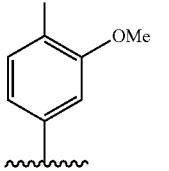 |

TABLE 1-continued

| No. | X | Z |
|---|---|---|
| I-38 | 2-ethylcyclohexyl-O- | 4-fluoro-3-methoxyphenyl |
| I-39 | (trans-2-methylcyclohexyl)methyl-O- | 4-fluoro-3-methoxyphenyl |
| I-40 | (cis-2-methylcyclohexyl)methyl-O- | 4-fluoro-3-methoxyphenyl |
| I-41 | (2,6-dimethylcyclohexyl)methyl-O- | 4-fluoro-3-methoxyphenyl |
| I-42 | norbornyl-methyl-O- | 4-fluoro-3-methoxyphenyl |
| I-43 | norbornyl-methyl-O- | 4-fluoro-3-methoxyphenyl |
| I-44 | (3-methylcyclopentyl)-O- | 4-fluoro-3-methoxyphenyl |
| I-45 | (3-isopropylcyclopentyl)-O- | 4-fluoro-3-methoxyphenyl |
| I-46 | (3,3-dimethylcyclopentyl)-O- | 4-fluoro-3-methoxyphenyl |
| I-47 | (cis-3-methylcyclopentyl)-O- | 4-fluoro-3-methoxyphenyl |
| I-48 | (cis-3-methylcyclopentyl)-O- | 4-fluoro-3-methylphenyl |
| I-49 | (2,6-dichlorobenzyl)-O- | 5-(trifluoromethyl)pyridin-3-yl |
| I-50 | (2-chloro-6-fluorobenzyl)-NH- | 5-(trifluoromethyl)pyridin-3-yl |
| I-51 | (2,6-dichlorobenzyl)-O- | 1-methyl-1H-imidazol-4-yl |
| I-52 | (2-chloro-6-fluorobenzyl)-NH- | 1-methyl-1H-imidazol-4-yl |

TABLE 1-continued
| No. | X | Z |
|---|---|---|
| I-53 | 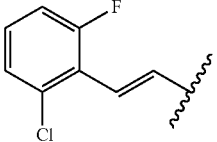 [SMILES: */C=C/c1c(F)cccc1Cl] | 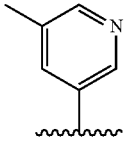 [SMILES: *c1cncc(C)c1] |
| I-54 | 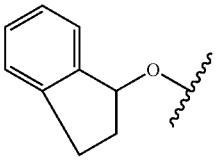 [SMILES: *OC1CCc2ccccc21] | 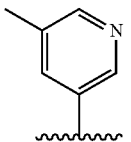 [SMILES: *c1cncc(C)c1] |
| I-55 | 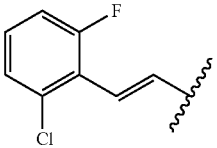 [SMILES: */C=C/c1c(F)cccc1Cl] | 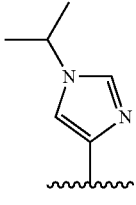 [SMILES: *c1cn(C(C)C)cn1] |
| I-56 | 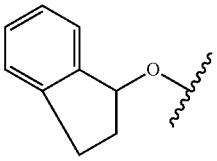 [SMILES: *OC1CCc2ccccc21] | 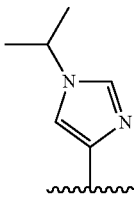 [SMILES: *c1cn(C(C)C)cn1] |
| I-57 | 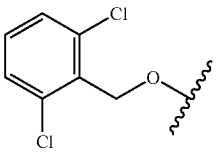 | 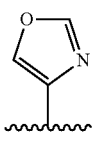 |
| I-58 | 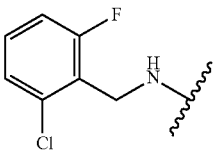 [SMILES: *NCc1c(F)cccc1Cl] | 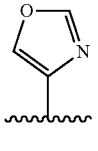 |
| I-59 | 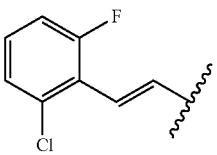 [SMILES: */C=C/c1c(F)cccc1Cl] | 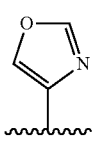 [SMILES: *c1cocn1] |
| I-60 | 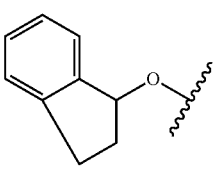 [SMILES: *OC1CCc2ccccc21] | 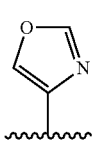 |
| I-61 | 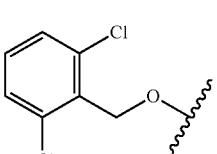 [SMILES: *OCc1ccccc1Cl] | 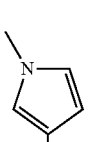 |
| I-62 | 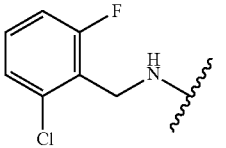 [SMILES: *NCc1c(F)cccc1Cl] | 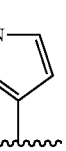 |
| I-63 | 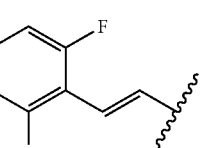 | 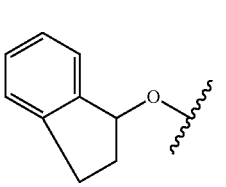 [SMILES: *OC1CCc2ccccc21] |
| I-64 | 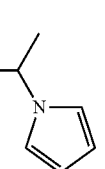 | 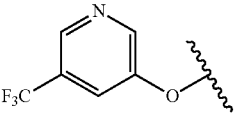 [SMILES: *Oc1cncc(C(F)(F)F)c1] |
| I-65 | 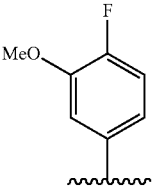 [SMILES: *c1ccc(F)c(OC)c1] | 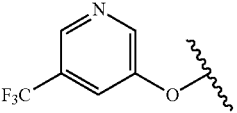 [SMILES: *Oc1cncc(C(F)(F)F)c1] |
| I-66 | 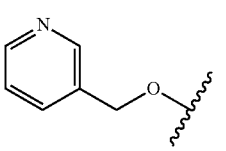 [SMILES: *OCc1cccnc1] | 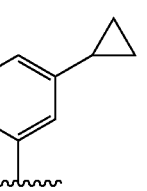 |
| I-67 | 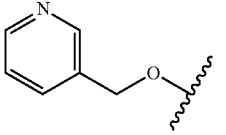 [SMILES: *OCc1cccnc1] | 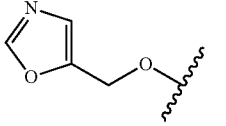 [SMILES: *OCc1cnco1] |
| I-68 | 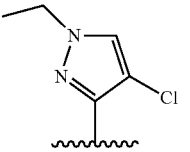 [SMILES: *c1nn(CC)cc1Cl] | |

TABLE 1-continued

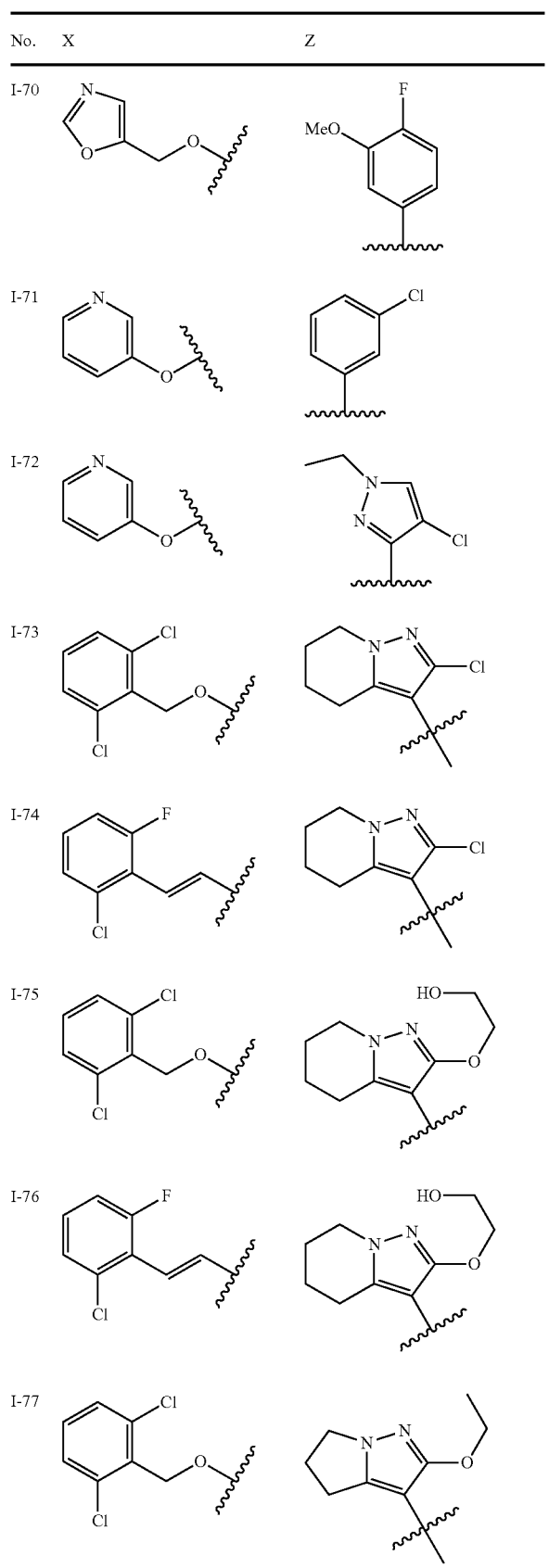
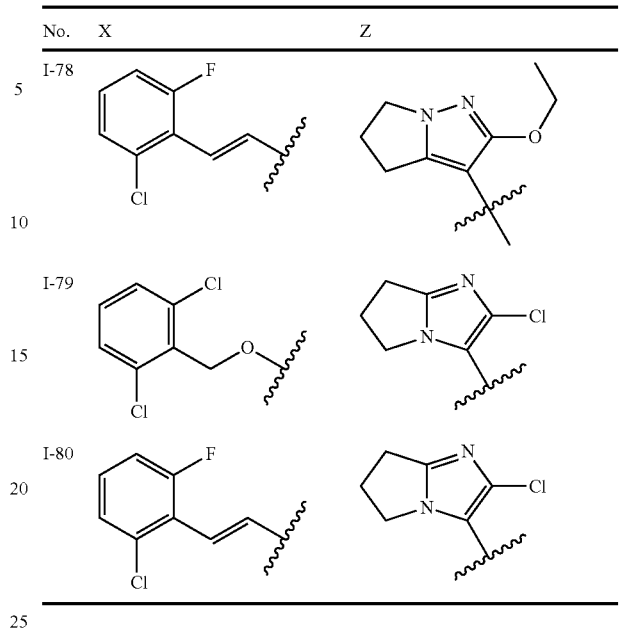

Methods for preparing compounds described herein are illustrated in the following synthetic Scheme. The Scheme is given for the purpose of illustrating the invention, and is not intended to limit the scope or spirit of the invention. Starting materials shown in the Scheme can be obtained from commercial sources or be prepared based on procedures described in the literature.

Scheme 1 illustrates a general method of forming substituted N-alkyl-N-phenyl(aryl or heteroaryl)sulfonamides C. Conversion of a substituted aniline A to the N-alkyl-aniline B can be achieved in, for example, three different ways: (1) reductive amination with an aldehyde (E. E. Boros et al. *J. Org. Chem.* 74: 3587-3590, 2009; and C. A. Maryanoff et al. *J. Org. Chem.* 61: 3849-3860, 1996), (2) acylation, followed by reduction with either borane or lithium aluminum hydride, or (3) alkylation with an alkyl halide. Treatment of the N-alkyl-aniline B with a sulfonyl halide in the presence of a suitable base affords the N-alkyl-N-phenyl(aryl or heteroaryl)sulfonamides C. Additional procedures for making benzenesulfonamido compounds are provided in the Examples. Analogous procedures can be used to prepare sulfonamides where R" is cycloalkyl or heterocycloalkyl.

SCHEME 1.

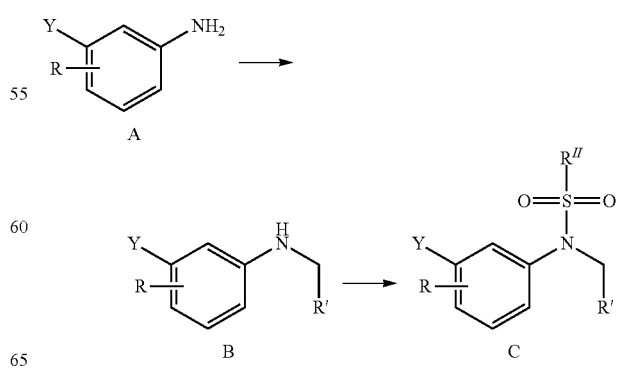

Part II: Benzylsulfone Compounds

Another aspect of the invention provides a compound represented by Formula II:

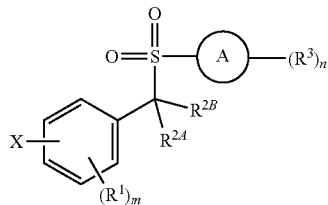

(II)

or a pharmaceutically acceptable salt thereof; wherein:

A is phenylene, 5-6 membered heteroarylene, or $C_{3-6}$heterocycloalkylene;

$R^1$ represents independently for each occurrence halogen, $C_{1-6}$alkyl, $C_{1-6}$haloalkyl, or $C_{3-6}$cycloalkyl;

$R^{2A}$ is $C_{1-6}$alkyl, $C_{3-6}$cycloalkyl, or $C_{3-6}$heterocyclyl, each of which is optionally substituted with 1, 2, or 3 substituents independently selected from the group consisting of —$CO_2R^4$, halogen, hydroxyl, $C_{1-6}$alkoxy, $C_{1-6}$haloalkoxy, cyano, —$N(R^4)(R^5)$, —$N(R^4)C(O)R^5$, —$SO_2R^6$, and —$C(O)N(R^4)(R^5)$;

$R^{2B}$ is hydrogen or $C_{1-6}$alkyl; or $R^{2A}$ and $R^{2B}$ are taken together with the carbon atom to which they are attached to form a 3-6 membered cycloalkyl or heterocycloalkyl group optionally substituted with 1, 2, or 3 substituents independently selected from the group consisting of —$CO_2R^4$, —$C(O)R^4$, —$SO_2R^6$, halogen, hydroxyl, $C_{1-6}$alkoxy, $C_{1-6}$haloalkoxy, $C_{1-6}$alkyl, $C_{1-6}$haloalkyl, cyano, and —$N(R^4)(R^5)$;

$R^3$ represents independently for each occurrence hydrogen, $C_{1-6}$haloalkyl, halogen, $C_{1-6}$alkyl, $C_{1-6}$alkoxy, $C_{1-6}$haloalkoxy, or hydroxyl; or two vicinal occurrences of $R^3$ are taken together with intervening atoms to form a 4-6 membered ring;

$R^4$ and $R^5$ each represent independently for each occurrence hydrogen, $C_{1-6}$alkyl, or $C_{3-6}$cycloalkyl; or an occurrence of $R^4$ and $R^5$ attached to the same nitrogen atom are taken together with the nitrogen atom to which they are attached to form a 3-7 membered heterocyclic ring;

$R^6$ represents independently for each occurrence $C_{1-6}$alkyl or $C_{3-6}$cycloalkyl;

X is one of the following:

(i) —O-aralkyl, —O-heteroaralkyl, —O-phenyl, —O-heteroaryl, —O-(partially unsaturated bicyclic carbocyclyl), —O—($C_{1-6}$alkylene)-($C_{3-6}$cycloalkyl), —O—($C_{3-6}$cycloalkyl), —N($R^4$)-aralkyl, —N($R^4$)-phenyl, —N($R^4$)-(partially unsaturated bicyclic carbocyclyl), or —N($R^4$)—($C_{1-6}$alkylene)-($C_{3-6}$cycloalkyl), each of which is optionally substituted with 1, 2, or 3 substituents independently selected from the group consisting of halogen, $C_{1-6}$haloalkyl, $C_{1-6}$alkyl, $C_{3-6}$cycloalkyl, $C_{1-6}$alkoxy, $C_{1-6}$haloalkoxy, hydroxyl, and cyano;

(ii) —($C_{2-6}$alkenylene)-phenyl, —($C_{2-6}$alkenylene)-heteroaryl, —($C_{1-6}$alkylene)-phenyl, —($C_{1-6}$alkylene)-heteroaryl, —($C_{1-6}$alkylene)-(partially unsaturated bicyclic heterocyclyl), —($C_{1-6}$alkylene)-(partially unsaturated bicyclic oxo-heterocyclyl), -(5-6 membered heterocycloalkylene)-phenyl, or —($C_{3-6}$cycloalkylene)-phenyl, each of which is optionally substituted with 1, 2, or 3 substituents independently selected from the group consisting of halogen, $C_{1-6}$haloalkyl, $C_{1-6}$alkyl, $C_{3-6}$cycloalkyl, $C_{1-6}$alkoxy, $C_{1-6}$haloalkoxy, hydroxyl, and cyano; or (iii) —($C_{1-6}$alkylene)-$Z^1$ or —($C_{2-6}$alkenylene)-$Z^1$, wherein $Z^1$ is —O-aralkyl, —O-heteroaralkyl, —O-phenyl, —O-heteroaryl, —O-(partially unsaturated bicyclic carbocyclyl), —O—($C_{1-6}$alkylene)-($C_{3-6}$cycloalkyl), —O—($C_{3-6}$cycloalkyl), —N($R^4$)-aralkyl, —N($R^4$)-phenyl, —N($R^4$)-(partially unsaturated bicyclic carbocyclyl), —N($R^4$)—($C_{1-6}$alkylene)-($C_{3-6}$cycloalkyl), or —N($R^4$)—($C_{3-6}$cycloalkyl), each of which is optionally substituted with 1, 2, or 3 substituents independently selected from the group consisting of halogen, $C_{1-6}$haloalkyl, $C_{1-6}$alkyl, $C_{3-6}$cycloalkyl, $C_{1-6}$alkoxy, $C_{1-6}$haloalkoxy, hydroxyl, and cyano;

m is 0, 1, or 2; and n is 1, 2, or 3.

In certain embodiments, A is phenylene or 5-6 membered heteroarylene.

In certain embodiments, $R^1$ represents independently for each occurrence halogen or $C_{1-6}$alkyl.

In certain embodiments, X is further selected from an 8-10 membered, bicyclic partially saturated carbocyclyl which is optionally substituted with 1, 2, or 3 substituents independently selected from the group consisting of halogen, $C_{1-6}$haloalkyl, $C_{1-6}$alkyl, $C_{3-6}$cycloalkyl, $C_{1-6}$alkoxy, $C_{1-6}$haloalkoxy, —S—($C_{1-6}$alkyl), hydroxyl, and cyano.

The definitions of variables in Formula II above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii), e.g., such as where A is phenylene, $R^{2A}$ is $C_{1-6}$alkyl or $C_{3-6}$cycloalkyl, $R^{2B}$ is hydrogen, and $R^3$ is hydrogen, $C_{1-6}$haloalkyl, or halogen.

Another aspect of the invention provides a compound represented by Formula II-A:

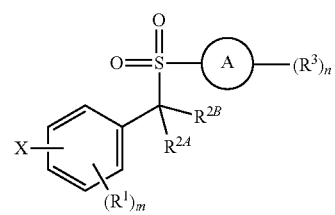

(II-A)

or a pharmaceutically acceptable salt thereof; wherein:

A is phenylene or a 5-6 membered heteroarylene;

$R^1$ represents independently for each occurrence halogen, $C_{1-6}$alkyl, or $C_{3-6}$cycloalkyl;

$R^{2A}$ is $C_{1-6}$alkyl or $C_{3-6}$cycloalkyl, each of which is optionally substituted with 1, 2, or 3 substituents independently selected from the group consisting of —$CO_2R^4$, halogen, hydroxyl, $C_{1-6}$alkoxy, $C_{1-6}$haloalkoxy, cyano, —$N(R^4)(R^5)$, and —$N(R^4)C(O)R^5$;

$R^{2B}$ is hydrogen or $C_{1-6}$alkyl;

$R^3$ represents independently for each occurrence hydrogen, $C_{1-6}$haloalkyl, halogen, $C_{1-6}$alkyl, $C_{1-6}$alkoxy, $C_{1-6}$haloalkoxy, or hydroxyl; or two vicinal occurrences of $R^3$ are taken together with intervening atoms to form a 4-6 membered ring;

R⁴ and R⁵ each represent independently for each occurrence hydrogen, $C_{1-6}$alkyl, or $C_{3-6}$cycloalkyl; or an occurrence of R⁴ and R⁵ attached to the same nitrogen atom are taken together with the nitrogen atom to which they are attached to form a 3-7 membered heterocyclic ring;

X is one of the following:
(i) —O-aralkyl, —O-heteroaralkyl, —O-phenyl, —O-heteroaryl, —O-(partially unsaturated bicyclic carbocyclyl), —O—($C_{1-6}$alkylene)-($C_{3-6}$cycloalkyl), —N(R⁴)-aralkyl, —N(R⁴)-phenyl, —N(R⁴)-(partially unsaturated bicyclic carbocyclyl), or —N(R⁴)—($C_{1-6}$alkylene)-($C_{3-6}$cycloalkyl), each of which is optionally substituted with 1, 2, or 3 substituents independently selected from the group consisting of halogen, $C_{1-6}$haloalkyl, $C_{1-6}$alkyl, $C_{3-6}$cycloalkyl, $C_{1-6}$alkoxy, and $C_{1-6}$haloalkoxy;
(ii) —($C_{2-6}$alkenylene)-phenyl, —($C_{2-6}$alkenylene)-heteroaryl, —($C_{1-6}$alkylene)-phenyl, —($C_{1-6}$alkylene)-heteroaryl, —($C_{1-6}$alkylene)-(partially unsaturated bicyclic heterocyclyl), —($C_{1-6}$alkylene)-(partially unsaturated bicyclic oxo-heterocyclyl), or -(5-6 membered heterocycloalkylene)-phenyl, each of which is optionally substituted with 1, 2, or 3 substituents independently selected from the group consisting of halogen, $C_{1-6}$haloalkyl, $C_{1-6}$alkyl, $C_{3-6}$cycloalkyl, $C_{1-6}$alkoxy, and $C_{1-6}$haloalkoxy; or
(iii) —($C_{1-6}$alkylene)-$Z^1$ or —($C_{2-6}$alkenylene)-$Z^1$, wherein $Z^1$ is —O-aralkyl, —O-heteroaralkyl, —O-phenyl, —O-heteroaryl, —O-(partially unsaturated bicyclic carbocyclyl), —O—($C_{1-6}$alkylene)-($C_{3-6}$cycloalkyl), —O—($C_{3-6}$cycloalkyl), —N(R⁴)-aralkyl, —N(R⁴)-phenyl, —N(R⁴)-(partially unsaturated bicyclic carbocyclyl), or —N(R⁴)—($C_{1-6}$alkylene)-($C_{3-6}$cycloalkyl), each of which is optionally substituted with 1, 2, or 3 substituents independently selected from the group consisting of halogen, $C_{1-6}$haloalkyl, $C_{1-6}$alkyl, $C_{3-6}$cycloalkyl, $C_{1-6}$alkoxy, and $C_{1-6}$haloalkoxy;

m is 0, 1, or 2; and
n is 1, 2, or 3.

In certain embodiments, A is phenylene. In certain other embodiments, A is a 5-6 membered heteroarylene. In yet other embodiments, -A-$(R^3)_n$ is one of the following:

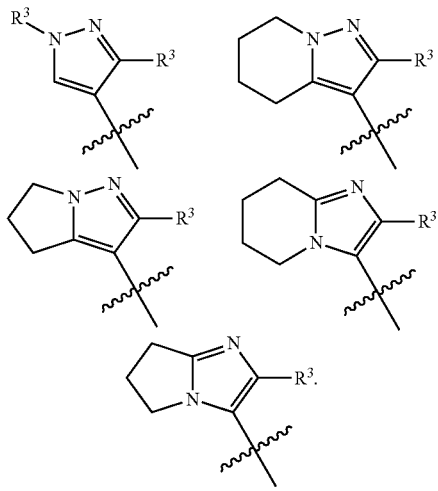

In certain embodiments, $R^1$ represents independently for each occurrence halogen or methyl.

In certain embodiments, $R^2$ is $C_{1-6}$alkyl optionally substituted with 1, 2, or 3 substituents independently selected from the group consisting of —$CO_2R^4$, halogen, hydroxyl, $C_{1-6}$alkoxy, and —N(R⁴)C(O)R⁵. In certain other embodiments, $R^2$ is $C_{1-6}$alkyl optionally substituted with 1, 2, or 3 substituents independently selected from the group consisting of —$CO_2R^4$, halogen, hydroxyl, and $C_{1-6}$alkoxy. In certain other embodiments, $R^2$ is $C_{1-6}$alkyl optionally substituted with 1 substituent selected from the group consisting of —$CO_2R^4$, halogen, hydroxyl, and $C_{1-6}$alkoxy. In certain other embodiments, $R^2$ is $C_{1-6}$alkyl optionally substituted with —$CO_2R^4$. In certain other embodiments, $R^2$ is ethyl or propyl.

In certain embodiments, n is 1. In certain other embodiments, n is 1 or 2.

In certain embodiments, $R^3$ is $C_{1-6}$haloalkyl. In certain other embodiments, $R^3$ is trifluoromethyl. In yet other embodiments, $R^3$ represents independently for each occurrence $C_{1-6}$haloalkyl, halogen, $C_{1-6}$alkyl, or $C_{1-6}$alkoxy.

In certain embodiments, X is —O-aralkyl, —O-heteroaralkyl, —O-phenyl, —O-heteroaryl, —O-(partially unsaturated bicyclic carbocyclyl), —O—($C_{1-6}$alkylene)-($C_{3-6}$cycloalkyl), —N(R⁴)-aralkyl, —N(R⁴)-phenyl, —N(R⁴)-(partially unsaturated bicyclic carbocyclyl), or —N(R⁴)—($C_{1-6}$alkylene)-($C_{3-6}$cycloalkyl), each of which is optionally substituted with 1, 2, or 3 substituents independently selected from the group consisting of halogen, $C_{1-6}$haloalkyl, $C_{1-6}$alkyl, $C_{3-6}$cycloalkyl, $C_{1-6}$alkoxy, and $C_{1-6}$haloalkoxy. In certain other embodiments, X is —O-aralkyl, —O-phenyl, —O-(partially unsaturated bicyclic carbocyclyl), —O—($C_{1-6}$alkylene)-($C_{3-6}$cycloalkyl), —N(R⁴)-aralkyl, —N(R⁴)-phenyl, —N(R⁴)-(partially unsaturated bicyclic carbocyclyl), or —N(R⁴)—($C_{1-6}$alkylene)-($C_{3-6}$cycloalkyl), each of which is optionally substituted with 1, 2, or 3 substituents independently selected from the group consisting of halogen, $C_{1-6}$haloalkyl, $C_{1-6}$alkyl, $C_{3-6}$cycloalkyl, $C_{1-6}$alkoxy, and $C_{1-6}$haloalkoxy. In certain other embodiments, X is —O-aralkyl, —O-(partially unsaturated bicyclic carbocyclyl), or —O—($C_{1-6}$alkylene)-($C_{3-6}$cycloalkyl), each of which is optionally substituted with 1, 2, or 3 substituents independently selected from the group consisting of halogen, $C_{1-6}$haloalkyl, $C_{1-6}$alkyl, $C_{3-6}$cycloalkyl, $C_{1-6}$alkoxy, and $C_{1-6}$haloalkoxy. In certain other embodiments, X is —O-aralkyl or —O-(partially unsaturated bicyclic carbocyclyl), each of which is optionally substituted with 1 or 2 substituents independently selected from the group consisting of halogen and $C_{1-6}$haloalkyl. In certain other embodiments, X is —O-benzyl substituted with 1 or 2 substituents independently selected from the group consisting of chloro, bromo, and fluoro.

In certain embodiments, X is —O—($C_{1-6}$alkylene)-phenyl or —N(R⁴)—($C_{1-6}$alkylene)-phenyl, each of which is substituted with 1, 2, or 3 substituents independently selected from the group consisting of halogen, $C_{1-6}$haloalkyl, $C_{1-6}$alkyl, $C_{3-6}$cycloalkyl, $C_{1-6}$alkoxy, and $C_{1-6}$haloalkoxy, where at least one substituent is present at the ortho position on the phenyl group in variable X.

In certain embodiments, X is —($C_{2-6}$alkenylene)-phenyl, —($C_{2-6}$alkenylene)-heteroaryl, —($C_{1-6}$alkylene)-phenyl, —($C_{1-6}$alkylene)-heteroaryl, —($C_{1-6}$alkylene)-(partially unsaturated bicyclic heterocyclyl), —($C_{1-6}$alkylene)-(partially unsaturated bicyclic oxo-heterocyclyl), or -(5-6 membered heterocycloalkylene)-phenyl, each of which is optionally substituted with 1, 2, or 3 substituents independently selected from the group consisting of halogen, $C_{1-6}$haloalkyl, $C_{1-6}$alkyl, $C_{3-6}$cycloalkyl, $C_{1-6}$alkoxy, and $C_{1-6}$haloalkoxy. In certain other embodiments, X is —($C_{2-6}$alkenylene)-phenyl or —(C$_{1-6}$alkylene)-phenyl, each of which is optionally substituted with 1, 2, or 3 substituents independently selected from the group consisting of halogen, C$_{1-6}$haloalkyl, C$_{1-6}$alkyl, C$_{3-6}$cycloalkyl, C$_{1-6}$alkoxy, C$_{1-6}$haloalkoxy, hydroxyl, and cyano. In certain other embodiments, X is —(C$_{1-6}$alkylene)-heteroaryl, —(C$_{1-6}$alkylene)-(partially unsaturated bicyclic heterocyclyl), —(C$_{1-6}$alkylene)-(partially unsaturated bicyclic oxo-heterocyclyl), or -(5-6 membered heterocycloalkylene)-phenyl, each of which is optionally substituted with 1, 2, or 3 substituents independently selected from the group consisting of halogen, C$_{1-6}$haloalkyl, C$_{1-6}$alkyl, C$_{3-6}$cycloalkyl, C$_{1-6}$alkoxy, and C$_{1-6}$haloalkoxy.

In certain embodiments, X is —(C$_{1-6}$alkylene)-Z$^1$ or —(C$_{2-6}$alkenylene)-Z$^1$, wherein Z$^1$ is —O-aralkyl, —O-heteroaralkyl, —O-phenyl, —O-heteroaryl, —O-(partially unsaturated bicyclic carbocyclyl), —O—(C$_{1-6}$alkylene)-(C$_{3-6}$cycloalkyl), —O—(C$_{3-6}$cycloalkyl), —N(R$^4$)-aralkyl, —N(R$^4$)-phenyl, —N(R$^4$)-(partially unsaturated bicyclic carbocyclyl), or —N(R$^4$)—(C$_{1-6}$alkylene)-(C$_{3-6}$cycloalkyl), each of which is optionally substituted with 1, 2, or 3 substituents independently selected from the group consisting of halogen, C$_{1-6}$haloalkyl, C$_{1-6}$alkyl, C$_{3-6}$cycloalkyl, C$_{1-6}$alkoxy, and C$_{1-6}$haloalkoxy. In certain other embodiments, X is —(C$_{1-6}$alkylene)-Z$^1$, wherein Z$^1$ is —O-aralkyl, —O-phenyl, —O-(partially unsaturated bicyclic carbocyclyl), —O—(C$_{1-6}$alkylene)-(C$_{3-6}$cycloalkyl), —O—(C$_{3-6}$cycloalkyl), —N(R$^4$)-aralkyl, —N(R$^4$)-phenyl, —N(R$^4$)-(partially unsaturated bicyclic carbocyclyl), or —N(R$^4$)—(C$_{1-6}$alkylene)-(C$_{3-6}$cycloalkyl), each of which is optionally substituted with 1, 2, or 3 substituents independently selected from the group consisting of halogen, C$_{1-6}$haloalkyl, C$_{1-6}$alkyl, C$_{3-6}$cycloalkyl, C$_{1-6}$alkoxy, and C$_{1-6}$haloalkoxy. In certain embodiments, X is —(C$_{1-6}$alkylene)-Z$^1$, wherein Z$^1$ is —O-aralkyl, —N(R$^4$)-aralkyl, or —N(R$^4$)-phenyl, each of which is optionally substituted with 1, 2, or 3 substituents independently selected from the group consisting of halogen, C$_{1-6}$haloalkyl, and C$_{1-6}$alkyl.

In certain embodiments, X is attached at the meta or para position of the methylene-sulfonyl-substituted group.

In certain embodiments, X is further selected from an 8-10 membered, bicyclic partially saturated carbocyclyl which is optionally substituted with 1, 2, or 3 substituents independently selected from the group consisting of halogen, C$_{1-6}$haloalkyl, C$_{1-6}$alkyl, C$_{3-6}$cycloalkyl, C$_{1-6}$alkoxy, C$_{1-6}$haloalkoxy, —S—(C$_{1-6}$alkyl), hydroxyl, and cyano.

In certain embodiments, m is 0. In certain embodiments, m is 1.

The definitions of variables in Formula II-A above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii), e.g., such as where A is phenylene, R$^{2A}$ is C$_{1-6}$alkyl or C$_{3-6}$cycloalkyl, R$^{2B}$ is hydrogen, and R$^3$ is hydrogen, C$_{1-6}$haloalkyl, or halogen.

Another aspect of the invention provides a compound represented by Formula II-B:

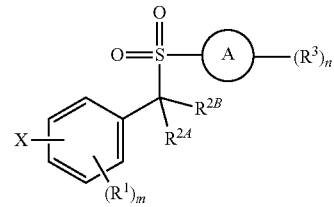

or a pharmaceutically acceptable salt thereof; wherein:
A is phenylene;
R$^1$ represents independently for each occurrence halogen, methyl, ethyl, or cyclopropyl;
R$^{2A}$ is C$_{1-6}$alkyl optionally substituted with 1 or 2 substituents independently selected from the group consisting of —CO$_2$R$^4$, halogen, hydroxyl, C$_{1-6}$alkoxy, and —N(R$^4$)C(O)(C$_{1-6}$alkyl);
R$^{2B}$ is hydrogen or methyl;
R$^3$ represents independently for each occurrence C$_{1-3}$haloalkyl, halogen, and C$_{1-3}$ alkyl;
R$^4$ represents independently for each occurrence hydrogen or methyl;
X is attached at the meta or para position of the methylene-sulfonyl-substituted group, and X is one of the following:
  (i) —O—(C$_{1-6}$alkylene)-phenyl, —O-(partially unsaturated bicyclic carbocyclyl), or —O—(C$_{1-6}$alkylene)-(C$_{3-6}$cycloalkyl), each of which is optionally substituted with 1, 2, or 3 substituents independently selected from the group consisting of halogen, C$_{1-6}$haloalkyl, C$_{1-6}$alkyl, and C$_{1-6}$alkoxy;
  (ii) —(C$_{2-6}$alkenylene)-phenyl or —(C$_{1-6}$alkylene)-phenyl, each of which is optionally substituted with 1, 2, or 3 substituents independently selected from the group consisting of halogen, C$_{1-6}$haloalkyl, C$_{1-6}$alkyl, C$_{3-6}$cycloalkyl, C$_{1-6}$alkoxy, and C$_{1-6}$haloalkoxy; or
  (iii) —(C$_{1-6}$alkylene)-Z$^1$, wherein Z$^1$ is —O-aralkyl, —O-phenyl, —O-(partially unsaturated bicyclic carbocyclyl), —O—(C$_{1-6}$alkylene)-(C$_{3-6}$cycloalkyl), —O—(C$_{3-6}$cycloalkyl), —N(R$^4$)-aralkyl, —N(R$^4$)-phenyl, —N(R$^4$)-(partially unsaturated bicyclic carbocyclyl), or —N(R$^4$)—(C$_{1-6}$alkylene)-(C$_{3-6}$cycloalkyl), each of which is optionally substituted with 1, 2, or 3 substituents independently selected from the group consisting of halogen, C$_{1-6}$haloalkyl, C$_{1-6}$alkyl, and C$_{1-6}$alkoxy;
m is 0, 1, or 2; and
n is 1 or 2.

In certain embodiments, X is —O—(C$_{1-6}$alkylene)-phenyl optionally substituted with 1 or 2 substituents independently selected from the group consisting of halogen, C$_{1-6}$haloalkyl, and C$_{1-6}$alkyl.

The definitions of variables in Formula II-B above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

In certain other embodiments, the compound is a compound defined by one of the following formulae where variables X and Z are as defined in Table 2, or a pharmaceutically acceptable salt thereof

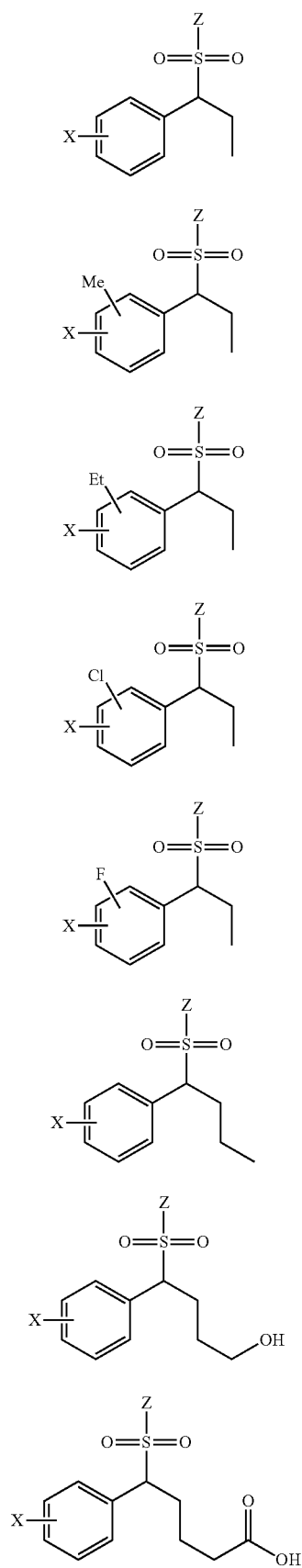
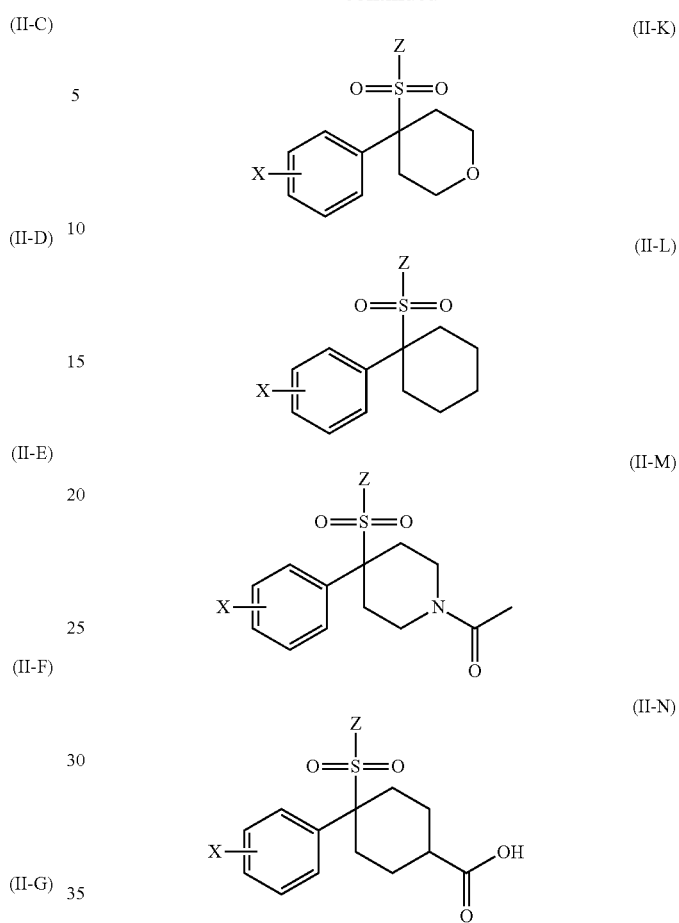

TABLE 2-continued

| No. | X | Z |
|---|---|---|
| II-4 | 2-Cl, 6-F benzyl-O- | 4-F, 3-CF₃ phenyl |
| II-5 | 2,6-diCl benzyl-O- | 1-ethyl-4-chloro-pyrazol-3-yl |
| II-6 | 2-Cl, 6-F benzyl-O- | 1-ethyl-3-ethoxy-pyrazol-4-yl |
| II-7 | 2-Cl, 6-F benzyl-O- | 1-ethyl-4-(2-hydroxyethoxy)-pyrazol-3-yl |
| II-8 | 2-Cl, 6-F benzyl-O- | 3,5-dimethylpiperidin-1-yl |
| II-9 | 2-Cl, 6-F benzyl-O- | 4-methylpiperidin-1-yl |
| II-10 | 2-Cl, 6-F benzyl-NH- | 4-F, 3-OMe phenyl |
| II-11 | 2-Cl, 6-F (1-methylvinyl)phenyl | 4-F, 3-OMe phenyl |
| II-12 | cyclohexyl-CH₂-O- | 4-F, 3-OMe phenyl |
| II-13 | indan-1-yl-O- | 4-F, 3-OMe phenyl |
| II-14 | indan-1-yl-CH₂- | 4-F, 3-OMe phenyl |
| II-15 | 1,2,3,4-tetrahydronaphthalen-1-yl-O- | 4-F, 3-OMe phenyl |
| II-16 | 7-chloroindan-1-yl-O- | 4-F, 3-OMe phenyl |
| II-17 | indan-1-yl-NH- | 4-F, 3-OMe phenyl |
| II-18 | 2-(2-Cl, 6-F phenyl)-2-methylcyclopropyl | 4-F, 3-OMe phenyl |
| II-19 | 2-Cl, 6-F (1-ethylvinyl)phenyl | 4-F, 3-OMe phenyl |

TABLE 2-continued

| No. | X | Z |
|---|---|---|
| II-20 | 2-F, 6-Cl phenyl with C(CF₃)=CH- | 4-F-3-OMe-phenyl |
| II-21 | indan-1-ylidene-methyl | 4-F-3-OMe-phenyl |
| II-22 | 2-F, 6-Cl phenyl -CH=C(CH₃)- | 4-F-3-OMe-phenyl |
| II-23 | 2-F, 6-Cl phenyl -C(CH₃)=C(CH₃)- | 4-F-3-OMe-phenyl |
| II-24 | tetralin-2-yl | 4-F-3-OMe-phenyl |
| II-25 | indan-2-yl | 4-F-3-OMe-phenyl |
| II-26 | 2-Cl-benzyl-O-CH< | 4-F-3-OMe-phenyl |
| II-27 | 2,6-diCl-benzyl-O-CH< | 4-F-3-OMe-phenyl |
| II-28 | 2-Cl-6-CF₃-benzyl-O-CH< | 4-F-3-OMe-phenyl |
| II-29 | 2-F-6-CF₃-benzyl-O-CH< | 4-F-3-OMe-phenyl |
| II-30 | benzyl-O-CH< | 4-F-3-OMe-phenyl |
| II-31 | 2-Cl-6-methyl-benzyl-O-CH< | 4-F-3-OMe-phenyl |
| II-32 | cyclopentyl-O-CH< | 4-F-3-OMe-phenyl |
| II-33 | cyclohexyl-O-CH< | 4-F-3-OMe-phenyl |
| II-34 | trans-2-methyl-cyclopentyl-O-CH< | 4-F-3-OMe-phenyl |

TABLE 2-continued

| No. | X | Z |
|---|---|---|
| II-35 | (trans-2-methylcyclopentyl-O-) | 4-fluoro-3-methoxyphenyl |
| II-36 | (trans-2-methylcyclohexyl-O-) | 4-fluoro-3-methoxyphenyl |
| II-37 | (cis-2-methylcyclohexyl-O-) | 4-fluoro-3-methoxyphenyl |
| II-38 | (2-ethylcyclohexyl-O-) | 4-fluoro-3-methoxyphenyl |
| II-39 | (trans-2-methylcyclohexyl-CH$_2$-O-) | 4-fluoro-3-methoxyphenyl |
| II-40 | (cis-2-methylcyclohexyl-CH$_2$-O-) | 4-fluoro-3-methoxyphenyl |
| II-41 | (2,6-dimethylcyclohexyl-CH$_2$-O-) | 4-fluoro-3-methoxyphenyl |
| II-42 | (norbornyl-CH$_2$-O-) | 4-fluoro-3-methoxyphenyl |
| II-43 | (norbornyl-CH$_2$-O-) | 4-fluoro-3-methoxyphenyl |
| II-44 | (trans-3-methylcyclopentyl-O-) | 4-fluoro-3-methoxyphenyl |
| II-45 | (trans-3-isopropylcyclopentyl-O-) | 4-fluoro-3-methoxyphenyl |
| II-46 | (3,3-dimethylcyclopentyl-O-) | 4-fluoro-3-methoxyphenyl |
| II-47 | (cis-3-methylcyclopentyl-O-) | 4-fluoro-3-methoxyphenyl |
| II-48 | (cis-3-methylcyclopentyl-O-) | 4-fluoro-3-methylphenyl |
| II-49 | (2,6-dichlorobenzyl-O-) | 5-trifluoromethylpyridin-3-yl |

TABLE 2-continued

| No. | X | Z |
|---|---|---|
| II-50 | 2-F, 6-Cl benzyl-NH- | 5-(F₃C)-pyridin-3-yl |
| II-51 | 2,6-diCl benzyl-O-CH- | 1-methyl-imidazol-4-yl |
| II-52 | 2-F, 6-Cl benzyl-NH- | 1-methyl-imidazol-4-yl |
| II-53 | 2-F, 6-Cl styryl- | 5-methyl-pyridin-3-yl |
| II-54 | indan-1-yl-O- | 5-methyl-pyridin-3-yl |
| II-55 | 2-F, 6-Cl styryl- | 1-isopropyl-imidazol-4-yl |
| II-56 | indan-1-yl-O- | 1-isopropyl-imidazol-4-yl |
| II-57 | 2,6-diCl benzyl-O-CH- | oxazol-4-yl |
| II-58 | 2-F, 6-Cl benzyl-NH- | oxazol-4-yl |
| II-59 | 2-F, 6-Cl styryl- | oxazol-4-yl |
| II-60 | indan-1-yl-O- | oxazol-4-yl |
| II-61 | 2,6-diCl benzyl-O-CH- | 1-methyl-pyrrol-3-yl |
| II-62 | 2-F, 6-Cl benzyl-NH- | 1-methyl-pyrrol-3-yl |
| II-63 | 2-F, 6-Cl styryl- | 1-isopropyl-pyrrol-3-yl |
| II-64 | indan-1-yl-O- | 1-isopropyl-pyrrol-3-yl |
| II-65 | 5-(F₃C)-pyridin-3-yl-O- | 4-F, 3-MeO-phenyl |
| II-66 | 5-(F₃C)-pyridin-3-yl-O- | 3-Cl-phenyl |

TABLE 2-continued

| No. | X | Z |
|-----|---|---|
| II-67 | (3-pyridylmethyloxy) | (3-cyclopropylphenyl) |
| II-68 | (3-pyridylmethyloxy) | (4-fluoro-3-trifluoromethylphenyl) |
| II-69 | (oxazol-5-ylmethyloxy) | (1-ethyl-4-chloropyrazol-3-yl) |
| II-70 | (oxazol-5-ylmethyloxy) | (3-methoxy-4-fluorophenyl) |
| II-71 | (3-pyridyloxy) | (3-chlorophenyl) |
| II-72 | (3-pyridyloxy) | (1-ethyl-4-chloropyrazol-3-yl) |
| II-73 | (2,6-dichlorobenzyloxy) | (3-chloro-4,5,6,7-tetrahydropyrazolo[1,5-a]pyridin-2-yl) |
| II-74 | (2-fluoro-6-chlorostyryl) | (3-chloro-4,5,6,7-tetrahydropyrazolo[1,5-a]pyridin-2-yl) |
| II-75 | (2,6-dichlorobenzyloxy) | (3-(2-hydroxyethoxy)-4,5,6,7-tetrahydropyrazolo[1,5-a]pyridin-2-yl) |
| II-76 | (2-fluoro-6-chlorostyryl) | (3-(2-hydroxyethoxy)-4,5,6,7-tetrahydropyrazolo[1,5-a]pyridin-2-yl) |
| II-77 | (2,6-dichlorobenzyloxy) | (2-ethoxy-5,6-dihydro-4H-pyrrolo[1,2-b]pyrazol-3-yl) |
| II-78 | (2-fluoro-6-chlorostyryl) | (2-ethoxy-5,6-dihydro-4H-pyrrolo[1,2-b]pyrazol-3-yl) |
| II-79 | (2,6-dichlorobenzyloxy) | (2-chloro-6,7-dihydro-5H-pyrrolo[1,2-a]imidazol-3-yl) |
| II-80 | (2-fluoro-6-chlorostyryl) | (2-chloro-6,7-dihydro-5H-pyrrolo[1,2-a]imidazol-3-yl) |

Methods for preparing compounds described herein are illustrated in the following synthetic Schemes. The Schemes are given for the purpose of illustrating the invention, and are not intended to limit the scope or spirit of the invention. Starting materials shown in the Schemes can be obtained from commercial sources or be prepared based on procedures described in the literature.

Scheme 2 illustrates a general method of forming substituted (benzyl or heteroarylalkyl sulfonyl)benzenes D. Treatment of a benzylic halide A (where $X^1$ is halogen) with a mercaptan affords the thioether B. Oxidation with meta-chloroperbenzoic acid or another oxidant affords the sulfone C. Stepwise alkylation with one to two alkyl halides forms the sulfones D. When alkylating with a dihalide, R' and R" can form a ring. Analogous procedures can be used to prepare sulfones where R" is cycloalkyl or heterocycloalkyl. Additional procedures for making benzylsulfone compounds are provided in the Examples.

SCHEME 2.

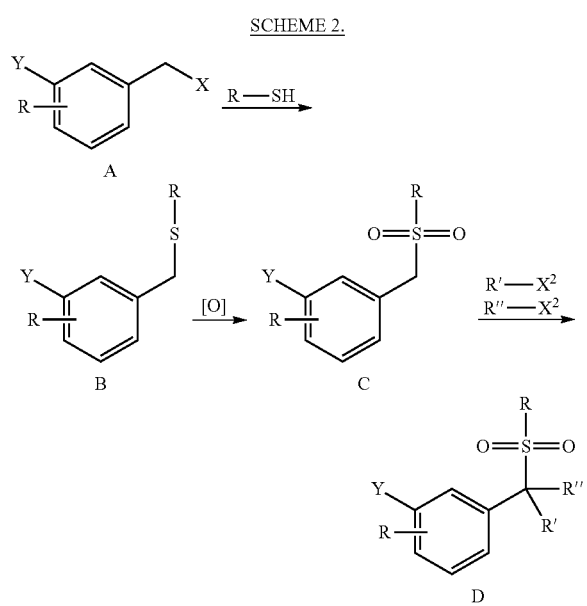

Scheme 3 illustrates a general method of forming substituted 1-benzylsulfonamides D where R and R" are taken together with the nitrogen atom to which they are attached to form a heterocycloalkyl group. Treatment of a benzylic halide A (where $X^1$ is halogen) with sodium sulfite followed by thionyl chloride affords the sulfonyl halide B. Treatment with aza-heterocycloalkyl HN(R)(R") affords the sulfonamide C. Stepwise alkylation with one to two alkyl halides ($R'''-X^2$ and/or $R''''-X^2$) forms sulfonamide D. When alkylating with a dihalide, R''' and R'''' can form a ring.

SCHEME 3.

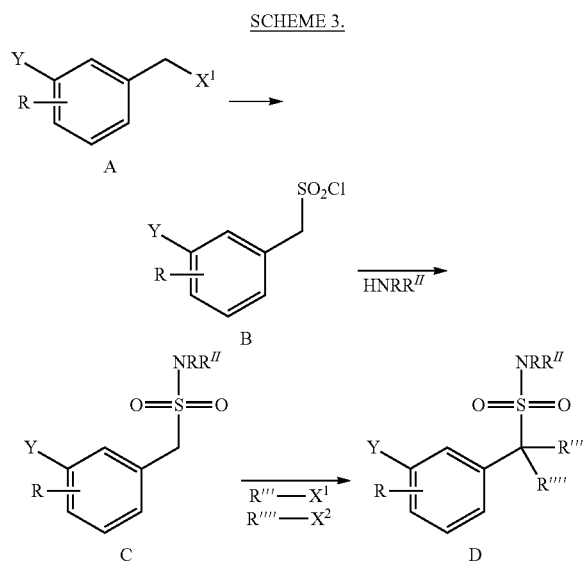

II. Therapeutic Applications of Benzenesulfonamido and Related Compounds

It is contemplated that the benzenesulfonamido and related compounds described herein, such as a compound of Formula I, I-A, I-B, II, II-A, II-B, or other compounds in Section I, provide therapeutic benefits to subjects suffering from a cancer, bacterial infection, fungal infection, or immune deficiency disorder. Accordingly, one aspect of the invention provides a method of treating a disorder selected from the group consisting of cancer, bacterial infection, fungal infection, and immune deficiency disorder. The method comprises administering a therapeutically effective amount of a benzenesulfonamido or related compound described herein, such as a compound of Formula I, I-A, I-B, II, II-A, II-B, or other compounds in Section I, to a subject in need thereof to ameliorate a symptom of the disorder. In certain embodiments, the particular compound of Formula I, I-A, I-B, II, II-A, or II-B is a compound defined by one of the embodiments described above.

In certain embodiments, the disorder is cancer. In certain embodiments, the cancer is a solid tumor or leukemia. In certain other embodiments, the cancer is colon cancer, pancreatic cancer, breast cancer, ovarian cancer, prostate cancer, squamous cell carcinoma, basal cell carcinoma, adenocarcinoma, sweat gland carcinoma, sebaceous gland carcinoma, lung cancer, leukemia, bladder cancer, stomach cancer, cervical cancer, testicular cancer, skin cancer, rectal cancer, thyroid cancer, kidney cancer, uterus cancer, esophagus cancer, liver cancer, an acoustic neuroma, oligodendroglioma, meningioma, neuroblastoma, or retinoblastoma. In certain other embodiments, the cancer is small cell lung cancer, non-small cell lung cancer, melanoma, cancer of the central nervous system tissue, brain cancer, Hodgkin's lymphoma, non-Hodgkin's lymphoma, cutaneous T-Cell lymphoma, cutaneous B-Cell lymphoma, or diffuse large B-Cell lymphoma. In certain other embodiments, the cancer is breast cancer, colon cancer, small-cell lung cancer, non-small cell lung cancer, prostate cancer, renal cancer, ovarian cancer, leukemia, melanoma, or cancer of the central nervous system tissue. In certain other embodiments, the cancer is colon cancer, small-cell lung cancer, non-small cell lung cancer, renal cancer, ovarian cancer, renal cancer, or melanoma.

Additional exemplary cancers include fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, epithelial carcinoma, glioma, astrocytoma, medulloblastoma, and hemangioblastoma.

In certain embodiments, the cancer is a neuroblastoma, meningioma, hemangiopericytoma, multiple brain metastase, glioblastoma multiforms, glioblastoma, brain stem glioma, poor prognosis malignant brain tumor, malignant glioma, anaplastic astrocytoma, anaplastic oligodendroglioma, neuroendocrine tumor, rectal adeno carcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, metastatic melanoma, localized melanoma, malignant mesothelioma, malignant pleural effusion mesothelioma syndrome, peritoneal carcinoma, papillary serous carcinoma, gynecologic sarcoma, soft tissue sarcoma, sceleroderma, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, Waidenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, or leiomyoma.

In certain embodiments, the disorder is a bacterial infection. The bacterial infection can be characterized according to classifications known in the art. For example, in certain embodiments, the bacterial infection is a gram-positive bacterial infection, such as a gram-positive cocci bacterial infection or a gram-positive bacilli bacterial infection. In other embodiments, the bacterial infection is a gram-negative bacterial infection, such as a gram-negative cocci bacterial infection or a gram-negative bacilli bacterial infection. The bacterial infection can also be characterized according to whether it is caused by anaerobic or aerobic bacteria. Accordingly, in certain embodiments, the bacterial infection is an anaerobic bacterial infection. In certain other embodiments, the bacterial infection is an aerobic bacterial infection.

A variety of bacteria are contemplated to be susceptible to the benzenesulfonamido compounds. Representative bacteria include *Staphylococci* species, e.g., *S. aureus*; *Enterococci* species, e.g., *E. faecalis* and *E. faecium*; *Streptococci* species, e.g., *S. pyogenes* and *S. pneumoniae*; *Escherichia* species, e.g., *E. coli*, including enterotoxigenic, enteropathogenic, enteroinvasive, enterohemorrhagic and enteroaggregative *E. coli* strains; *Haemophilus* species, e.g., *H. influenza*; and *Moraxella* species, e.g., *M. catarrhalis*. Other examples include *Mycobacteria* species, e.g., *M. tuberculosis*, *M. avian-intracellulare*, *M. kansasii*, *M. bovis*, *M. africanum*, *M. genavense*, *M. leprae*, *M. xenopi*, *M. simiae*, *M. scrofulaceum*, *M. malmoense*, *M. celatum*, *M. abscessus*, *M. chelonae*, *M. szulgai*, *M. gordonae*, *M. haemophilum*, *M. fortuni* and *M. marinum*; *Corynebacteria* species, e.g., *C. diphtheriae*; *Vibrio* species, e.g., *V. cholerae*; *Campylobacter* species, e.g., *C. jejuni*; *Helicobacter* species, e.g., *H. pylori*; *Pseudomonas* species, e.g., *P. aeruginosa*; *Legionella* species, e.g., *L. pneumophila*; *Treponema* species, e.g., *T. pallidum*; *Borrelia* species, e.g., *B. burgdorferi*; *Listeria* species, e.g., *L. monocytogenes*; *Bacillus* species, e.g., *B. cereus*; *Bordatella* species, e.g., *B. pertussis*; *Clostridium* species, e.g., *C. perfringens*, *C. tetani*, *C. difficile* and *C. botulinum*; *Neisseria* species, e.g., *N. meningitidis* and *N. gonorrhoeae*; *Chlamydia* species, e.g., *C. psittaci*, *C. pneumoniae* and *C. trachomatis*; *Rickettsia* species, e.g., *R. rickettsii* and *R. prowazekii*; *Shigella* species, e.g., *S. sonnei*; *Salmonella* species, e.g., *S. typhimurium*; *Yersinia* species, e.g., *Y. enterocolitica* and *Y. pseudotuberculosis*; *Klebsiella* species, e.g., *K. pneumoniae*; *Mycoplasma* species, e.g., *M. pneumoniae*; and *Trypanosoma brucei*. In certain embodiments, the compounds described herein are used to treat a subject suffering from a bacterial infection selected from the group consisting of *S. aureus, E. faecalis, E. faecium, S. pyogenes, S. pneumonia*, and *P. aeruginosa*.

The antibacterial activity of compounds described herein may be evaluated using assays known in the art, such as the microbroth dilution minimum inhibition concentration (MIC) assay, as further described in National Committee for Clinical Laboratory Standards. Performance Standards for Antimicrobial Susceptibility Testing; Fourteenth Informational Supplement. NCCLS document M100-S14 {ISBN 1-56238-516-X}. This assay may be used to determine the minimum concentration of a compound necessary to prevent visible bacterial growth in a solution. In general, the drug to be tested is serially diluted into wells, and aliquots of liquid bacterial culture are added. This mixture is incubated under appropriate conditions, and then tested for growth of the bacteria. Compounds with low or no antibiotic activity (a high MIC) will allow growth at high concentrations of compound, while compounds with high antibiotic activity will allow bacterial growth only at lower concentrations (a low MIC).

The assay uses stock bacterial culture conditions appropriate for the chosen strain of bacteria. Stock cultures from the permanent stock culture collection can be stored as frozen suspensions at −70° C. Cultures may be suspended in 10% skim milk (BD) prior to snap freezing in dry ice/ethanol and then placed in a −70° C. freezer. Cultures may be maintained on Tryptic Soy Agar containing 5% Sheep Blood at room temperature (20° C.), and each culture may be recovered from frozen form and transferred an additional time before MIC testing. Fresh plates are inoculated the day before testing, incubated overnight, and checked to confirm purity and identity.

The identity and purity of the cultures recovered from the stock culture can be confirmed to rule out the possibility of contamination. The identity of the strains may be confirmed by standard microbiological methods (See, e.g., Murray et al., Manual of Clinical Microbiology, Eighth Edition. ASM Press {ISBN 1-55581-255-4}). In general, cultures are streaked onto appropriate agar plates for visualization of purity, expected colony morphology, and hemolytic patterns. Gram stains can also be utilized. The identities are confirmed using a MicroScan WalkAway 40 SI Instrument (Dade Behring, West Sacramento, Calif.). This device utilizes an automated incubator, reader, and computer to assess for identification purposes the biochemical reactions carried out by each organism. The MicroScan WalkAway can also be used to determine a preliminary MIC, which may be confirmed using the method described below.

Frozen stock cultures may be used as the initial source of organisms for performing microbroth dilution minimum inhibition concentration (MIC) testing. Stock cultures are passed on their standard growth medium for at least 1 growth cycle (18-24 hours) prior to their use. Most bacteria may be prepared directly from agar plates in 10 mL aliquots of the appropriate broth medium. Bacterial cultures are adjusted to the opacity of a 0.5 McFarland Standard (optical density value of 0.28-0.33 on a Perkin-Elmer Lambda EZ150 Spectrophotometer, Wellesley, Mass., set at a wavelength of 600 nm). The adjusted cultures are then diluted 400 fold (0.25 mL inoculum+100 mL broth) in growth media to produce a starting suspension of approximately $5 \times 10^5$ colony forming units (CFU)/mL. Most bacterial strains may be tested in cation adjusted Mueller Hinton Broth (CAMHB).

Test compounds ("drugs") are solubilized in a solvent suitable for the assay, such as DMSO. Drug stock solutions may be prepared on the day of testing. Microbroth dilution stock plates may be prepared in two dilution series, 64 to 0.06 μg drug/mL and 0.25 to 0.00025 μg drug/mL. For the high concentration series, 200 μL of stock solution (2 mg/mL) is added to duplicate rows of a 96-well microtiter plate. This is used as the first well in the dilution series. Serial two-fold decremental dilutions are made using a BioMek FX robot (Beckman Coulter Inc., Fullerton, Calif.) with 10 of the remaining 11 wells, each of which will contain 100 μL of the appropriate solvent/diluent. Row 12 contains solvent/diluent only and serves as the control. For the first well of the low concentration series, 200 µL of an 8 µg/mL stock are added to duplicate rows of a 96-well plate. Serial two-fold dilutions are made as described above.

Daughter 96-well plates may be spotted (3.2 µL/well) from the stock plates listed above using the BioMek FX robot and used immediately or frozen at −70° C. until use. Aerobic organisms are inoculated (100 µL volumes) into the thawed plates using the BioMek FX robot. The inoculated plates are be placed in stacks and covered with an empty plate. These plates are then incubated for 16 to 24 hours in ambient atmosphere according to CLSI guidelines (National Committee for Clinical Laboratory Standards, Methods for Dilution, Antimicrobial Tests for Bacteria that Grow Aerobically; Approved Standard-Sixth Edition. NCCLS document M7-A6 {ISBN 1-56238-486-4}).

After inoculation and incubation, the degree of bacterial growth can be estimated visually with the aid of a Test Reading Mirror (Dynex Technologies 220 16) in a darkened room with a single light shining directly through the top of the microbroth tray. The MIC is the lowest concentration of drug that prevents macroscopically visible growth under the conditions of the test.

In certain embodiments, the disorder is a fungal infection. Exemplary fungi that may be treated include, for example, *Acremonium, Absidia* (e.g., *Absidia corymbifera*), *Alternaria, Aspergillus* (e.g., *Aspergillus clavatus, Aspergillus flavus, Aspergillus fumigatus, Aspergillus nidulans, Aspergillus niger, Aspergillus terreus,* and *Aspergillus versicolor*), *Aureobasidium, Basidiobolus, Blastomyces* (e.g., *Blastomyces dermatitidis*), *Candida* (e.g., *Candida albicans, Candida glabrata, Candida guilliermondii, Candida kefyr, Candida krusei, Candida lusitaniae, Candida parapsilosis, Candida pseudotropicalis, Candida stellatoidea, Candida tropicalis, Candida utilis, Candida lipolytica, Candida famata* and *Candida rugosa*), *Cephalosporium, Chaetomium, Chrysosporium, Cladosporium* (e.g., *Cladosporium carrionii* and *Cladosporium trichloides*), *Coccidioides* (e.g., *Coccidioides immitis*), *Conidiobolus, Coprinus, Corynespora, Cryptococcus* (e.g., *Cryptococcus neoformans*), *Curvularia, Cunninghamella* (e.g., *Cunninghamella elegans*), *Exophiala* (e.g., *Exophiala dermatitidis* and *Exophiala spinifera*), *Epidermophyton* (e.g., *Epidermophyton floccosum*), *Fonsecaea* (e.g., *Fonsecaea pedrosoi*), *Fusarium* (e.g., *Fusarium solani*), *Geotrichum* (e.g., *Geotrichum candiddum* and *Geotrichum clavatum*), *Hendersonula, Histoplasma, Leptosphaeria, Loboa, Madurella, Malassezia* (e.g., *Malassezia furfur*), *Microsporum* (e.g., *Microsporum canis* and *Microsporum gypseum*), *Mycocentrospora, Mucor, Neotestudina, Paecilomyces, Paracoccidioides* (e.g., *Paracoccidioides brasiliensis*), *Penicillium* (e.g., *Penicillium marneffei*), *Phialophora, Pneumocystis* (e.g., *Pneumocystis carinii*), *Pseudallescheria* (e.g., *Pseudallescheria boydii*), *Rhinosporidium, Rhizomucor, Rhizopus* (e.g., *Rhizopus microsporus var. rhizopodiformis* and *Rhizopus oryzae*), *Saccharomyces* (e.g., *Saccharomyces cerevisiae*), *Scopulariopsis, Sporothrix* (e.g., *Sporothrix schenckii*), *Trichophyton* (e.g., *Trichophyton mentagrophytes* and *Trichophyton rubrum*), *Trichosporon* (e.g., *Trichosporon asahii, Trichosporon beigelii* and *Trichosporon cutaneum*), and *Wangiella*.

In certain embodiments, the disorder is an immune deficiency disorder. Exemplary immune deficiency disorders include, for example, a human immunodeficiency viral infection, a patient with a deficient immune system due to chemotherapy, or a patient recovering from surgery who has a deficient immune system.

In certain embodiments, the subject is a human.

Another aspect of the invention provides for the use of a compound described herein (such as a compound of Formula I, I-A, I-B, II, II-A, II-B, or other compounds in Section I) in the manufacture of a medicament. In certain embodiments, the medicament is for treating a disorder described herein, such as cancer.

Another aspect of the invention provides for the use of a compound described herein (such as a compound of Formula I, I-A, I-B, II, II-A, II-B, or other compounds in Section I) for treating a medical disorder, such a medical disorder described herein (e.g., cancer).

Further, it is contemplated that benzenesulfonamido and related compounds described herein, such as a compound of Formula I, I-A, I-B, II, II-A, II-B, or other compounds in Section I, can promote the activity of RORγ. Accordingly, another aspect of the invention provides a method of promoting the activity of RORγ. The method comprises exposing a RORγ to an effective amount of a benzenesulfonamido or related compound described herein, such as a compound of Formula I, I-A, I-B, II, II-A, II-B, or other compounds in Section I, to promote RORγ activity. In certain embodiments, the particular compound of Formula I, I-A, I-B, II, II-A, or II-B is the compound defined by one of the embodiments described above. Promoting the activity of RORγ means to increase the activity of RORγ. In certain embodiments, exposing a RORγ to an effective amount of a benzenesulfonamido or related compound described herein (such as a compound of Formula I, I-A, I-B, II, II-A, II-B, or other compounds in Section I) results in an increase in RORγ activity of at least 5%, 10%, 20%, or 50% relative to the activity of RORγ under substantially the same conditions but without the presence of the benzenesulfonamido or related compound.

Further, it is contemplated that benzenesulfonamido and related compounds described herein, such as a compound of Formula I, I-A, I-B, II, II-A, II-B, or other compounds in Section I, can increase the amount of interleukin-17 (IL-17) in a subject. IL-17 is a cytokine that affects numerous biological functions. Accordingly, another aspect of the invention provides a method of increasing the amount of IL-17 in a subject. The method comprises administering to a subject an effective amount of a benzenesulfonamido or related compound described herein, such as a compound of Formula I, I-A, I-B, II, II-A, II-B, or other compounds in Section I, to increase the amount of IL-17 in the subject. In certain embodiments, the particular compound of Formula I, I-A, I-B, II, II-A, or II-B is the compound defined by one of the embodiments described above.

In certain embodiments, the subject is a human. In certain embodiments, administering the compound increases the amount of IL-17 produced by Th-17 cells in the subject. A change in the amount of IL-17 produced by, for example, Th-17 cells can be measured using procedures described in the literature, such as an ELISA assay or intracellular staining assay.

Further, it is contemplated that benzenesulfonamido and related compounds described herein, such as a compound of Formula I, I-A, I-B, II, II-A, II-B, or other compounds in Section I, may increase the synthesis of IL-17 in a subject. Accordingly, another aspect of the invention provides a method of increasing the synthesis of IL-17 in a subject. The method comprises administering to a subject an effective amount of a compound described herein, e.g., a compound of Formula I, I-A, I-B, II, II-A, II-B, or other compounds in Section I, to increase the synthesis of IL-17 in the subject. In certain embodiments, the particular compound of Formula I, I-A, I-B, II, II-A, or II-B is a compound defined by one of the embodiments described above.

Adoptive Cellular Therapy

RORγ agonist compounds described herein may also be used in adoptive cellular therapy to treat various medical disorders, such as cancer, bacterial infections, fungal infections, and immune disorders. Cells, e.g., lymphocyte cells or dendritic cells, are exposed ex vivo to an RORγ agonist compound herein, and then the treated cells are administered to a patient. In adoptive cellular transfer, cells are obtained from a source (typically the patient in need of treatment), cultured ex vivo with an agent, and then the resulting cells are administered to the patient in need of therapy. The culturing typically subjects the cells to conditions whereby the cells increase in number (i.e., expansion) and/or acquire features providing improved therapeutic benefit. General features of the adoptive cellular therapy methods and compositions are described below, along with more specific embodiments of the lymphocyte cells, dendritic cells, and procedures for isolating and culturing cells.

Accordingly, one aspect of the invention provides a method of delivering to a patient a RORγ agonist treated cell selected from the group consisting of a lymphocyte cell and dendritic cell. The method comprises administering to a patient in need thereof a pharmaceutical composition comprising said cell that has been exposed ex vivo to an agonist of RORγ described herein, such as a compound of Formula I, I-A, I-B, II, II-A, or II-B. The method may further comprise a culturing step. In such embodiments, the method further comprises culturing a cell (i.e., the lymphocyte cell or dendritic cell) with an agonist of RORγ to provide the cell that has been exposed ex vivo to the agonist of RORγ. The culturing may comprise exposing the cell to a cytokine (e.g., IL-1β, IL-2, IL-6, IL-7, IL-10, IL-12, IL-15, IL-18, IL-21, IL-23, or transforming growth factor beta). During the culturing step, the cell may be exposed to an antigen associated with a medical disorder. Although not to be bound by theory, cells having an receptor specific to an antigen associated with a medical disorder can provide a more effective therapy than cells lacking such a receptor. Accordingly, in certain embodiments, the culturing step comprises exposing the cell to an antigen associated with a medical disorder. The antigen may be an antigen presenting cell. Alternatively, the antigen may comprise cancer tissue. Further, as described below, the cell may be genetically altered to express a receptor specific to an antigen associated with a medical disorder.

The cell may be autologous or allogenic. Autologous cells are cells obtained from the patient whom will receive the cell exposed ex vivo to an agonist of RORγ. As such, in certain embodiments, the method may further comprise obtaining a cell from said patient, for use in the culturing step. Alternatively, the cells may be allogenic, i.e., obtained from a subject that produces cells allogenic to cells of the patient. In such embodiments, the method may further comprise obtaining a cell from a subject that produces cells allogenic to lymphocyte cells of the patient, for use in the culturing step.

In certain embodiments, the cell is a lymphocyte cell. Lymphocyte cells can be obtained from human or animal tissues according to procedures described in the literature. In certain embodiments, the lymphocyte cell is obtained from blood, cancer tissue, bone marrow, the spleen, a lymph node, or the thymus. In certain other embodiments, the lymphocyte cell is obtained from a population of peripheral blood mononuclear cells, such as human peripheral blood mononuclear cells. In certain other embodiments, the lymphocyte cell is obtained from a lymph node in proximity to a tumor or site of infection. In certain other embodiments, the lymphocyte cell is obtained from cancer tissue. In yet other embodiments, the lymphocyte cell is a tumor-infiltrating-lymphocyte cell.

Cells can be characterized according to the presence of a receptor for an antigen specific for a medical disorder. In certain embodiments, the cell expresses a receptor for an antigen specific for a medical disorder. As indicate above, such cells may provide more effective therapies for treating disease since the cells are more likely to target tissue specific to the disease to be treated. In certain embodiments, the medical disorder is a cancer, bacterial infection, fungal infection, or immune disorder. In yet other embodiments, the cell may express a receptor that, while not specific for a medical disorder, has utility in enhancing cell efficacy in treating the disorder.

Various types of lymphocyte cells have been described in the literature for use in adoptive cellular transfer. In certain embodiments, the lymphocyte cell is a T cell. In certain other embodiments, the lymphocyte cell is a CD8$^+$ T cell, CD4$^+$ T cell, or T$_H$17 cell. In certain other embodiments, the lymphocyte cell is a CD8$^+$ T cell, CD4$^+$ T cell, or a combination thereof. In certain other embodiments, the lymphocyte cell is a natural killer cell. In certain other embodiments, the lymphocyte cell is a Tc17 cell, natural killer T cell, or γδ T cell. In yet other embodiments, the lymphocyte cell is a genetically altered lymphocyte cell.

Cells may be administered to the patient according to procedures described in the literature. In certain embodiments, the administering comprises injecting into the patient the pharmaceutical composition. The injecting may be intravenous injection or injection directly into diseased tissue, such as a tumor. In yet other embodiments, the injecting may be subcutaneous injection into the patient.

The therapeutic method embraces combination therapies, such as administering (i) an agent that enhances the efficacy of the cell exposed to the agonist of RORγ and/or (ii) an agent having independent efficacy in treating the target medical disorder.

Another aspect of the invention provides a method of preparing a population of cells that have been exposed ex vivo to an agonist of RORγ described herein, where the cells are lymphocyte cells and/or dendritic cells. The method comprises exposing a population of cells selected from the group consisting of lymphocyte cells and dendritic cells ex vivo to an agonist of RORγ described herein to thereby provide said population of cells that have been exposed ex vivo to an agonist of RORγ. The population of cells may be used in therapeutic methods described herein. The exposing step may comprise culturing a population of cells with the agonist of RORγ for a duration of time sufficient to increase the number of cells in the population. The culturing may comprise exposing the cell to a cytokine (e.g., IL-1β, IL-2, IL-6, IL-7, IL-10, IL-12, IL-15, IL-18, IL-21, IL-23, or transforming growth factor beta). Further during the culturing step, the cell may optionally be exposed to an antigen associated with a medical disorder. Accordingly, in certain embodiments, the culturing step comprises exposing the cell to an antigen associated with a medical disorder. The antigen may be an antigen presenting cell. Alternatively, the antigen may comprise cancer tissue. The cell may be autologous or allogenic. Autologous cells are cells obtained from the patient whom will receive the cell exposed ex vivo to an agonist of RORγ. As such, in certain embodiments, the method may further comprise obtaining a cell (i.e., a lymphocyte or dendritic cell) from said patient for use in the culturing step. Alternatively, the cells may be allogenic, i.e., obtained from subject that produces cells allogenic to cells of the patient. In such embodiments, the method may further comprise obtaining a cell from a subject that produces cells allogenic to cells of the patient, for use in the culturing step. In certain embodiments, the cell is a lymphocyte cell. Lymphocyte cells can be obtained from human or animal tissues according to procedures described in the literature. In certain embodiments, the lymphocyte cell is obtained from blood, cancer tissue, bone marrow, the spleen, a lymph node, or the thymus. In certain other embodiments, the lymphocyte cell is obtained from a population of peripheral blood mononuclear cells, such as human peripheral blood mononuclear cells. In certain other embodiments, the lymphocyte cell is obtained from a lymph node in proximity to a tumor or site of infection. In certain other embodiments, the lymphocyte cell is obtained from cancer tissue. In yet other embodiments, the lymphocyte cell is a tumor-infiltrating-lymphocyte cell.

Cells can be characterized according to the presence of a receptor for an antigen specific for a medical disorder. In certain embodiments, the cell expresses a receptor for an antigen specific for a medical disorder. As indicated above, such cells may provide more effective therapies for treating disease since the cells is more likely to target tissue specific to the disease to be treated. In certain embodiments, the medical disorder is a cancer, bacterial infection, fungal infection, or immune disorder. In yet other embodiments, the cell may express a receptor that, while not specific for a medical disorder, has utility in enhancing cell efficacy in treating the disorder.

As described above, various types of lymphocyte cells have been described in the literature for use in adoptive cellular transfer. In certain embodiments, the lymphocyte cell is a T cell. In certain other embodiments, the lymphocyte cell is a $CD8^+$ T cell, $CD4^+$ T cell, or $T_H17$ cell. In certain other embodiments, the lymphocyte cell is a $CD8^+$ T cell, $CD4^+$ T cell, or a combination thereof. In certain other embodiments, the lymphocyte cell is a natural killer cell. In certain other embodiments, the lymphocyte cell is a Tc17, natural killer T cell, or γδ T cell. In yet other embodiments, the lymphocyte cell is a genetically altered lymphocyte cell.

Another aspect of the invention provides a method of treating a medical disorder. The method comprises administering to a patient in need thereof a cell that has been exposed ex vivo to an agonist of RORγ described herein to treat the medical disorder, wherein the cell is a lymphocyte cell or dendritic cell. The medical disorder can be, for example, a cancer, bacterial infection, fungal infection, or immune disorder. Additional exemplary medical disorders are described above, and in certain embodiments, the medical disorder is a cancer selected from the group consisting of a solid tumor, lymphoma, and leukemia. In certain other embodiments, the medical disorder is a cancer selected from the group consisting of ovarian cancer, melanoma, colorectal cancer, lung cancer, breast cancer, prostate cancer, pancreatic cancer, renal cell carcinoma, leukemia, a B-cell lymphoma, and non-Hodgkin lymphoma.

Another aspect of the invention provides a population of lymphocyte cells that have been exposed ex vivo to an agonist of RORγ described herein. The population may be characterized by the presence and/or quantity of particular types of cells in the population. For example, in certain embodiments, the population comprises one or more of the following: T cells and natural killer cells. In certain other embodiments, a majority of lymphocyte cells in the population are T cells. In certain other embodiments, a majority of lymphocyte cells in the population are $CD8^+$ T cells, $CD4^+$ T cells, $T_H17$ cells, or a combination thereof. In yet other embodiments, a majority of lymphocyte cells in the population are natural killer cells. In yet other embodiments, a single type of lymphocyte cell (e.g., a T cell, $CD8^+$ T cell, $CD4^+$ T cell, $T_H17$ cell, Tc17 cell, natural killer T cell, or γδ T cell) comprises at least 60%, 70% 80%, 90% or 95% of the cells in the population. In yet other embodiments, the population is characterized by: (i) a majority of lymphocyte cells in the population are T cells, (ii) a majority of lymphocyte cells in the population are $CD8^+$ T cells, $CD4^+$ T cells, $T_H17$ cells, or a combination thereof, (iii) a majority of lymphocyte cells in the population are Tc17 cells, (iv) a majority of lymphocyte cells in the population are natural killer cells, or (v) a majority of lymphocyte cells in the population are natural killer T cells, γδ T cells, or a combination thereof. In yet other embodiments, a majority of lymphocyte cells in the population are $CD8^+$ T cells, $CD4^+$ T cells, or a combination thereof. In yet other embodiments, the population is characterized by a majority of lymphocyte cells in the population are Tc17 cells, CD4+ Th0 T lymphocyte cells, Th17-polarized CD4+ T lymphocyte cells, CD8+ Tc17 T lymphocyte cells, or a combination thereof.

In each of the above aspects and embodiments, lymphocyte cells may be characterized according to whether they are a tumor infiltrating lymphocyte, naïve T lymphocyte, memory T lymphocyte, effector T lymphocyte, $CD8^+$ T cell, $CD4^+$ T cell, $CD4^+/CD8^+$ double positive T lymphocyte, $CD28^+CD8^+$ T cell, or $T_H17$ cell. $CD8^+$ T cells can be separated into naïve $CD8^+$ T cells, memory $CD8^+$ T cells, and effector $CD8^+$ T cells, according to cell surface antigens characteristic to each type of cell. Whether a cell or cell population is positive for a particular cell surface marker can be determined by flow cytometry using staining with a specific antibody for the surface marker and an isotype matched control antibody. A cell population negative for a marker refers to the absence of significant staining of the cell population with the specific antibody above the isotype control, and positive refers to uniform staining of the cell population above the isotype control. For instance, $CD4^+$ T helper cells can be sorted into naive, central memory, and effector cells by identifying cell populations that have cell surface antigens. In certain embodiments, central memory CD4+ T cells are CD62L positive and CD45RO positive. In certain embodiments, effector $CD4^+$ T cells are CD62L and CD45RO negative. In yet other embodiments, the lymphocyte cell is a Th1 cell, Tc1 cell, Th0 cell, or Tc0 cell. In certain embodiments, the lymphocyte cell is a $CD8^+$ T cell, which is optionally further characterized according to the whether the $CD8^+$ T cell is a naïve $CD8^+$ T cell, a memory $CD8^+$ T cell, or an effector $CD8^+$ T cell. In certain embodiments, the lymphocyte cell is a memory $CD8^+$ T cell, which may be further characterized according to whether the cell is CD62L positive or CD45RO positive. In certain other embodiments, the lymphocyte cell is an effector $CD8^+$ T cell, which may be further characterized according to whether the cell is CD62L negative or CD45RO negative. In yet other embodiments, the lymphocyte cell is a CD4+ Th0 T lymphocyte, Th17-polarized CD4+ T lymphocyte, or CD8+ Tc17 T lymphocyte. In still other embodiments, the lymphocyte cell is a memory T cell present in CD62L+ or CD62L− subsets of CD8+ peripheral blood lymphocytes. In certain embodiments, the central memory T cells may be CD45RO+, CD62L+, CD8+ T cells. In certain embodiments, effector T cells are negative for CD62L, CCR7, CD28, and CD127, and positive for granzyme B and perforin.

T cells can be characterized according to identity of a T cell receptor located on the surface of the T cell. The T cell receptor is a disulfide-linked membrane-anchored heterodimer that normally consists of highly variable alpha (α) and beta (β) chains expressed as part of a complex with the invariant CD3 chain molecules. T cells expressing this receptor are referred to as α:β (or αβ) T cells. A minority of T cells express an alternate receptor, formed by variable gamma (γ) and delta (δ) chains, and such T cells are referred to as γδ T cells. One subtype of T cells is natural killer T (NKT) cells. NKT cells are a heterogeneous group of T cells that share properties of both T cells and natural killer NK cells. Many NKT cells recognize the non-polymorphic CD1d molecule, an antigen-presenting molecule that binds self- and foreign lipids and glycolipids. Other subtypes of T cells include, for example, $CD8^+$ T cells, $CD4^+$ T cells, Tc17 cells, natural killer T cells, and γδ T cells. Still other subtypes of T cells include, for example, $CD4^-CD8^-$ T cells and $CD28^+$ $CD8^+$ T cells.

Preferably the lymphocyte cell comprises a receptor specific for an antigen of a medical condition. The receptor can be the endogenous lymphocyte cell receptor, i.e., the antigen-specific lymphocyte cell receptor that is endogenous (i.e., native to) the lymphocyte. In such instances, the lymphocyte comprising the endogenous lymphocyte cell receptor can be a lymphocyte cell that was isolated from the patient, which is known to express the particular medical condition-specific antigen. Alternatively, the lymphocyte comprising the endogenous lymphocyte cell receptor can be a lymphocyte cell that was isolated from a subject that produces allogenic lymphocyte cells (i.e., lymphocyte cells that are histocompatible with the patient that will receive the lymphocyte cells). In certain embodiments, the subject from which lymphocyte cells are obtained may be immunized prior to obtaining the lymphocyte cells, so that the lymphocyte cells to be administered to the patient will have specificity for the medical disorder to be treated.

The antigen of a disease recognized by the endogenous lymphocyte cell receptor can be any antigen which is characteristic of the disease. For example, the antigen may be, for example, a tumor antigen, such as gp100, MART-1, TRP-1, TRP-2, tyrosinase, NY-ESO-1, MAGE-1, or MAGE-3.

Lymphocyte cells may also be characterized according to the presence of a phenotypic marker of activation for tumor reactivity, such as the presence of 4-1BBL. Populations of lymphocyte cells enriched for such a phenotypic marker may provide therapeutic advantages. Lymphocyte cells may also be characterized according to the level of expression of the RORγ. In certain embodiments, the lymphocyte cell may be induced to express or engineered to express RORγ, thereby increasing the amount of RORγ.

The lymphocyte cell may be a genetically modified lymphocyte cell, such as a genetically modified lymphocyte cell described in, for example, International Patent Application Publication No. WO 2012/129514, which is hereby incorporated by reference. Genetic modification of the lymphocyte may improve the efficacy of therapy by promoting the viability and/or function of transferred lymphocyte cells, provide a genetic marker to permit selection and/or evaluation of in vivo survival or migration, or may incorporate functions that improve the safety of immunotherapy, for example, by making the cell susceptible to negative selection in vivo. The lymphocyte may be genetically modified so that the lymphocyte cell expresses certain proteins, such as a survival cytokine (e.g., granulocyte-macrophage colony-stimulating factor) and/or receptor for an antigen (e.g., a tumor antigen).

Accordingly, in embodiments, lymphocyte cells are modified with chimeric antigen receptors (CAR). The CARs may comprise a single-chain antibody fragment (scFv) that is derived from the variable heavy (VH) and variable light (VL) chains of a monoclonal antibody (mAb) linked to the TCR $CD3^+$ chain that mediates T-cell activation and cytotoxicity. Costimulatory signals can also be provided through the CAR by fusing the costimulatory domain of CD28 or 4-1 BB to the $CD3^+$ chain. CARs are specific for cell surface molecules independent from HLA, thus overcoming the limitations of TCR-recognition including HLA-restriction and low levels of HLA-expression on tumor cells.

The description above describes multiple embodiments providing definitions for variables used herein. The application specifically contemplates all combinations of such variables, e.g., particular combinations of the definitions set forth for variables A and X.

III. Combination Therapy

Another aspect of the invention provides for combination therapy. Benzenesulfonamido and related compounds (e.g., a compound of Formula I, I-A, I-B, II, II-A, II-B, or other compounds in Section I) or their pharmaceutically acceptable salts may be used in combination with additional therapeutic agents to treat medical disorders, such as a cancer, bacterial infection, fungal infection, and immune deficiency disorder.

Exemplary therapeutic agents that may be used as part of a combination therapy in treating cancer, include, for example, mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustine, thymalfasin, sobuzoxane, nedaplatin, cytarabine, bicalutamide, vinorelbine, vesnarinone, aminoglutethimide, amsacrine, proglumide, elliptinium acetate, ketanserin, doxifluridine, etretinate, isotretinoin, streptozocin, nimustine, vindesine, flutamide, drogenil, butocin, carmofur, razoxane, sizofilan, carboplatin, mitolactol, tegafur, ifosfamide, prednimustine, picibanil, levamisole, teniposide, improsulfan, enocitabine, lisuride, oxymetholone, tamoxifen, progesterone, mepitiostane, epitiostanol, formestane, interferon-alpha, interferon-2 alpha, interferon-beta, interferon-gamma, colony stimulating factor-1, colony stimulating factor-2, denileukin diftitox, interleukin-2, and leutinizing hormone releasing factor.

An additional class of agents that may be used as part of a combination therapy in treating cancer is immune checkpoint inhibitors (also referred to as immune checkpoint blockers) Immune checkpoint inhibitors are a class of therapeutic agents that have the effect of blocking immune checkpoints. See, for example, Pardoll in *Nature Reviews Cancer* (2012) vol. 12, pages 252-264. Exemplary immune checkpoint inhibitors include agents that inhibit one or more of (i) cytotoxic T-lymphocyte-associated antigen 4 (CTLA4), (ii) programmed cell death protein 1 (PD1), (iii) PDL1, (iv) LAB3, (v) B7-H3, (vi) B7-H4, and (vii) TIM3. The CTLA4 inhibitor Ipilumumab has been approved by the United States Food and Drug Administration for treating melanoma.

Yet other agents that may be used as part of a combination therapy in treating cancer are monoclonal antibody agents that target non-checkpoint targets (e.g., herceptin) and non-cytoxic agents (e.g., tyrosine-kinase inhibitors).

Exemplary therapeutic agents that may be used as part of a combination therapy in treating a bacterial infection, include, for example, amoxicillin, azithromycin, cefazolin, ceftriaxone, cefuroxime, cephalexin, ciprofloxacin, clindamycin, doxycycline, levofloxacin, linezolid, metronidazole, moxifloxacin, and penicillin.

Exemplary therapeutic agents that may be used as part of a combination therapy in treating a fungal infection, include, for example, 2-phenylphenol; 8-hydroxyquinoline sulphate; acibenzolar-S-methyl; aldimorph; amidoflumet; ampropylfos; ampropylfos-potassium; andoprim; anilazine; azaconazole; azoxystrobin; benalaxyl; benodanil; benomyl; benthiavalicarb-isopropyl; benzamacril; benzamacril-isobutyl; bilanafos; binapacryl; biphenyl; bitertanol; blasticidin-S; bromuconazole; butylamine; calcium polysulphide; capsimycin; captafol; captan; carbendazim; carboxin; carpropamid; carvone; chinomethionat; chlobenthiazone; chlorfenazole; chloroneb; chlorothalonil; chlozolinate; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulphamide; hexaconazole; hymexazole; imazalil; imibenconazole; iminoctadine triacetate; iminoctadine tris (albesil); iodocarb; ipconazole; iprobenfos; iprodione; iprovalicarb; irumamycin; isoprothiolane; isovaledione; kasugamycin; kresoxim-methyl; oxyfenthiin; paclobutrazole; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolenitrine; tetraconazole; thiabendazole; thicyofen; thifluzamide; thiophanate-methyl; thiram; tioxymid; tricyclazole; tridemorph; trifloxystrobin; triflumizole; triforine; triticonazole; uniconazole; validamycin A; vinclozolin; zineb; ziram; and zoxamide.

The amount of benzenesulfonamido or related compound (e.g., a compound of Formula I, I-A, I-B, II, II-A, II-B, or other compounds in Section I) and additional therapeutic agent and the relative timing of administration may be selected in order to achieve a desired combined therapeutic effect. For example, when administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. Further, for example, a benzenesulfonamido or related compound (e.g., a compound of any one of Formula I, I-A, I-B, II, II-A, II-B, or other compounds in Section I) may be administered during a time when the additional therapeutic agent(s) exerts its prophylactic or therapeutic effect, or vice versa.

The doses and dosage regimen of the active ingredients used in the combination therapy may be determined by an attending clinician. In certain embodiments, the benzenesulfonamido or related compound (e.g., a compound of any one of Formula I, I-A, I-B, II, II-A, II-B, or other compounds in Section I) and the additional therapeutic agent(s) are administered in doses commonly employed when such agents are used as monotherapy for treating the disorder. In other embodiments, the benzenesulfonamido or related compound (e.g., a compound of any one of Formula I, I-A, I-B, II, II-A, II-B, or other compounds in Section I) and the additional therapeutic agent(s) are administered in doses lower than the doses commonly employed when such agents are used as monotherapy for treating the disorder. In certain embodiments, the benzenesulfonamido or related compound (e.g., a compound of any one of Formula I, I-A, I-B, II, II-A, II-B, or other compounds in Section I) and the additional therapeutic agent(s) are present in the same composition, which is suitable for oral administration.

In certain embodiments, the benzenesulfonamido or related compound (e.g., a compound of any one of Formula I, I-A, I-B, II, II-A, II-B, or other compounds in Section I) and the additional therapeutic agent(s) may act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

Another aspect of this invention is a kit comprising a therapeutically effective amount of the benzenesulfonamido or related compound (e.g., a compound of any one of Formula I, I-A, I-B, II, II-A, II-B, or other compounds in Section I), a pharmaceutically acceptable carrier, vehicle or diluent, and optionally at least one additional therapeutic agent listed above.

IV. Pharmaceutical Compositions and Dosing Considerations

As indicated above, the invention provides pharmaceutical compositions, which comprise a therapeutically-effective amount of one or more of the compounds described above, formulated together with one or more pharmaceutically acceptable carriers (additives) and/or diluents. The pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

If desired, the effective daily dose of the active compound may be administered as two, three, four, five, six or more sub-doses administered separately at appropriate intervals throughout the day, optionally, in unit dosage forms. Preferred dosing is one administration per day.

The invention further provides a unit dosage form (such as a tablet or capsule) comprising a benzenesulfonamido or related compound described herein in a therapeutically effective amount for the treatment of medical disorder described herein.

EXAMPLES

The invention now being generally described will be more readily understood by reference to the following examples, which are included for purposes of illustration of certain aspects and embodiments of the present invention, and are not intended to limit the invention. Starting materials described herein can be obtained from commercial sources or may be readily prepared from commercially available materials using transformations known to those of skill in the art.

Example 1

Synthesis of N-(3-(Benzyloxy)phenyl)-N-ethyl-3-(trifluoromethyl)-benzenesulfonamide

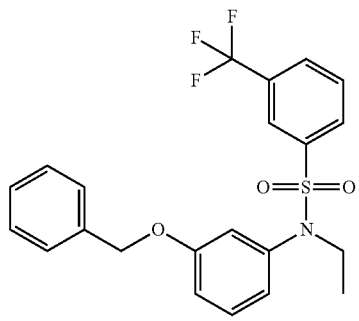 [SMILES: CCN(c1cccc(OCc2ccccc2)c1)S(=O)(=O)c1cccc(C(F)(F)F)c1]

Part I—Synthesis of N-Ethyl-N-(3-hydroxyphenyl)-3-(trifluoromethyl)benzenesulfonamide

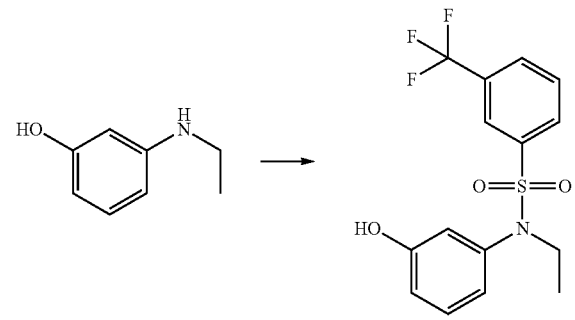

To a solution of 3-(ethylamino)phenol (0.64 g, 4.6 mmol) in dichloromethane (20 mL) at 0° C. was added pyridine (750 µL, 9.3 mmol) followed by 3-(trifluoromethyl)benzene sulfonyl chloride (1.25 g, 5.1 mmol). The resulting mixture was stirred for one hour, then methanol (1 mL) was added to quench the reaction, and the resulting mixture was concentrated to provide a residue. The residue was purified via MPLC on silica eluting with a gradient of 0-40% ethyl acetate in hexanes. The major UV component was concentrated to afford N-ethyl-N-(3-hydroxyphenyl)-3-(trifluoromethyl)benzenesulfonamide as a white solid (1.58 g, 97%).

Part II—Synthesis of N-(3-(Benzyloxy)phenyl)-N-ethyl-3-(trifluoromethyl)benzenesulfonamide

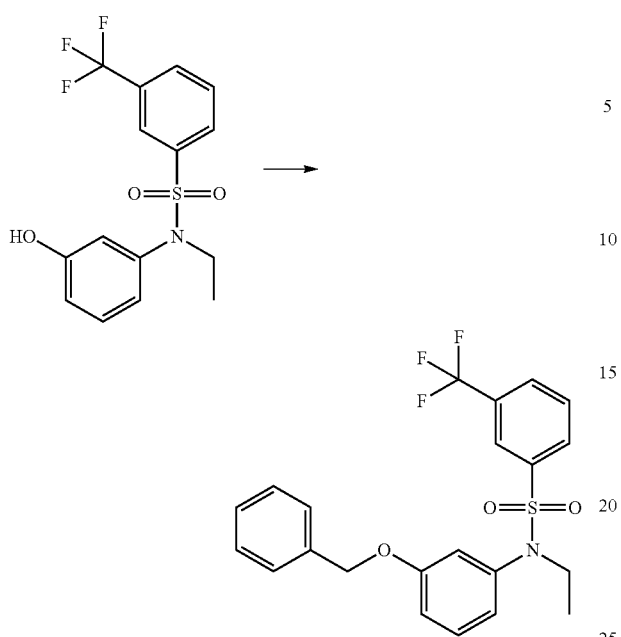

To a solution of N-ethyl-N-(3-hydroxyphenyl)-3-(trifluoromethyl)benzenesulfonamide (85 mg, 0.25 mmol) and triphenylphosphine (78 mg, 0.30 mmol) in THF (2 mL) was added benzyl alcohol (31 mg, 0.29 mmol) and diisopropyl azodicarboxylate (60 µL, 30 mmol). The resulting mixture was stirred overnight. Next, methanol (1 mL) was added to the reaction mixture, and the resulting mixture was stirred fifteen minutes, then concentrated to provide a residue. The residue was purified via MPLC on silica eluting with a gradient of 0-25% ethyl acetate in hexanes. The major UV component was concentrated to afford N-(3-(benzyloxy)phenyl)-N-ethyl-3-(trifluoromethyl)benzenesulfonamide (97 mg, 89%) as a colorless oil. $^1$H-NMR (400 MHz, DMSO-$d_6$) δ 8.11 (d, 1H) 7.94 (d, 1H), 7.87 (t, 1H), 7.70 (s, 1H), 7.37 (m, 5H), 7.29 (t, 1H), 7.02 (m, 2H), 5.00 (s, 2H), 3.60 (q, 2H), 0.97 (t, 3H).

Example 2

Preparation of Additional N-((Alkoxy and Arylalkoxy)phenyl)-N-alkyl-3-(aryl and heteroaryl)sulfonamides Compounds in Table 3 were prepared based on the experimental procedures described in Example 1 and in the detailed description.

TABLE 3

| No. | Structure | Chemical Name | Observed m/z |
|---|---|---|---|
| 2A | 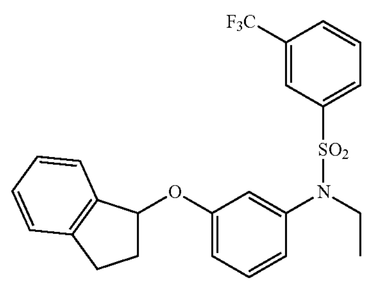 [SMILES: CCN(c1cccc(OC2CCc3ccccc32)c1)S(=O)(=O)c1cccc(C(F)(F)F)c1] | N-(3-((2,3-dihydro-1H-inden-1-yl)oxy)phenyl)-N-ethyl-3-(trifluoromethyl)benzenesulfonamide | 462 (M + H)$^+$ |
| 2B | 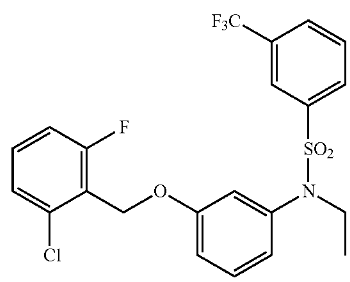 [SMILES: CCN(c1cccc(OCc2c(F)cccc2Cl)c1)S(=O)(=O)c1cccc(C(F)(F)F)c1] | N-(3-((2-chloro-6-fluorobenzyl)oxy)phenyl)-N-ethyl-3-(trifluoromethyl)benzenesulfonamide | 488 (M + H)$^+$ |
| 2C | 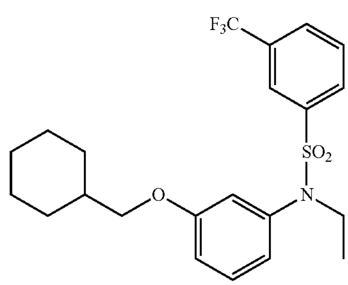 | N-(3-(cyclohexylmethoxy)phenyl)-N-ethyl-3-(trifluoromethyl)benzenesulfonamide | 488 (M + H)$^+$ |

TABLE 3-continued

| No. | Structure | Chemical Name | Observed m/z |
|---|---|---|---|
| 2D | 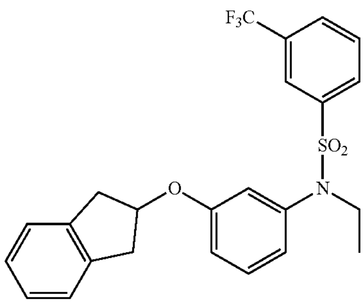 [SMILES: CCN(c1cccc(OC2Cc3ccccc3C2)c1)S(=O)(=O)c1cccc(C(F)(F)F)c1] | N-(3-((2,3-dihydro-1H-inden-2-yl)oxy)phenyl)-N-ethyl-3-(trifluoromethyl)benzenesulfonamide | 462 (M + H)+ |
| 2E | 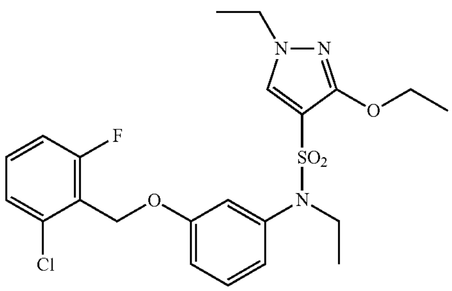 [SMILES: CCOc1nn(CC)cc1S(=O)(=O)N(CC)c1cccc(OCc2c(F)cccc2Cl)c1] | N-(3-((2-chloro-6-fluorobenzyl)oxy)phenyl)-3-ethoxy-N,1-diethyl-1H-pyrazole-4-sulfonamide | 482 (M + H)+ |
| 2F | 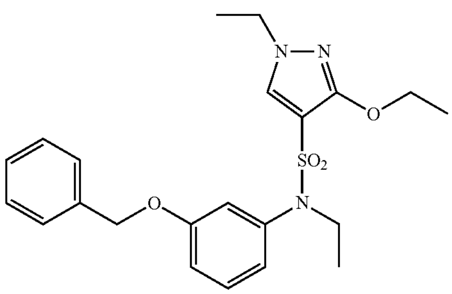 [SMILES: CCOc1nn(CC)cc1S(=O)(=O)N(CC)c1cccc(OCc2ccccc2)c1] | N-(3-(benzyloxy)phenyl)-3-ethoxy-N,1-diethyl-1H-pyrazole-4-sulfonamide | 430 (M + H)+ |
| 2G | 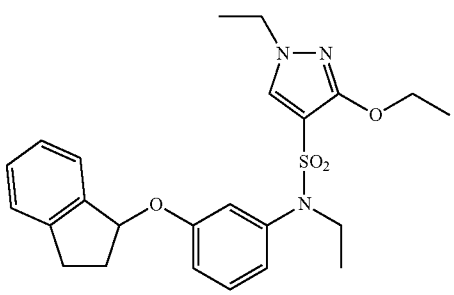 [SMILES: CCOc1nn(CC)cc1S(=O)(=O)N(CC)c1cccc(OC2CCc3ccccc32)c1] | N-(3-((2,3-dihydro-1H-inden-1-yl)oxy)phenyl)-3-ethoxy-N,1-diethyl-1H-pyrazole-4-sulfonamide | 456 (M + H)+ |
| 2H | 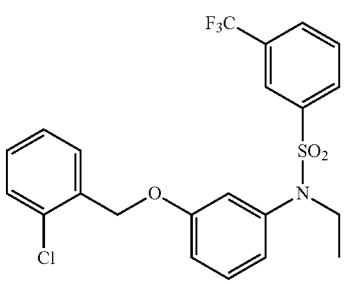 [SMILES: CCN(c1cccc(OCc2ccccc2Cl)c1)S(=O)(=O)c1cccc(C(F)(F)F)c1] | N-(3-((2-chlorobenzyl)oxy)phenyl)-N-ethyl-3-(trifluoromethyl)benzenesulfonamide | 470 (M + H)+ |

TABLE 3-continued

| No. | Structure | Chemical Name | Observed m/z |
|---|---|---|---|
| 2I | 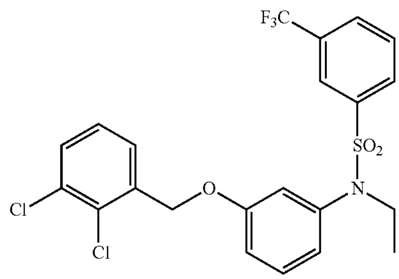 [SMILES: CCN(c1cccc(OCc2cccc(Cl)c2Cl)c1)S(=O)(=O)c1cccc(C(F)(F)F)c1] | N-(3-((2,3-dichlorobenzyl)oxy) phenyl)-N-ethyl-3-(trifluoromethyl) benzenesulfonamide | 504 (M + H)+ |
| 2J | 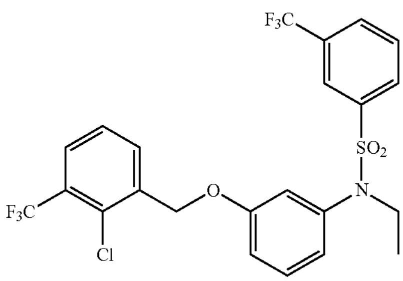 [SMILES: CCN(c1cccc(OCc2cccc(C(F)(F)F)c2Cl)c1)S(=O)(=O)c1cccc(C(F)(F)F)c1] | N-(3-((2-chloro-3-(trifluoromethyl)benzyl)oxy) phenyl)-N-ethyl-3-(trifluoromethyl) benzenesulfonamide | 538 (M + H)+ |
| 2K | 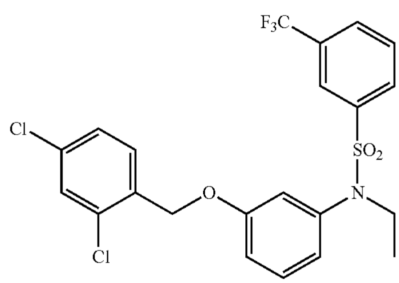 [SMILES: CCN(c1cccc(OCc2ccc(Cl)cc2Cl)c1)S(=O)(=O)c1cccc(C(F)(F)F)c1] | N-(3-((2,4-dichlorobenzyl)oxy) phenyl)-N-ethyl-3-(trifluoromethyl)benzenesulfonamide | 504 (M + H)+ |
| 2L | 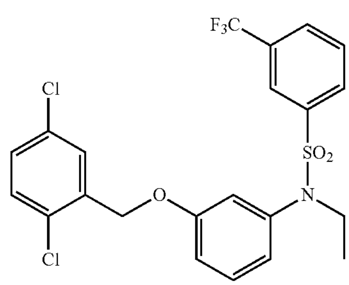 [SMILES: CCN(c1cccc(OCc2cc(Cl)ccc2Cl)c1)S(=O)(=O)c1cccc(C(F)(F)F)c1] | N-(3-((2,5-dichlorobenzyl)oxy) phenyl)-N-ethyl-3-(trifluoromethyl)benzenesulfonamide | 504 (M + H)+ |
| 2M | 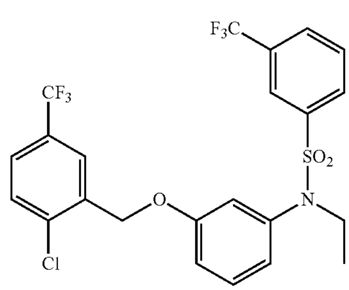 [SMILES: CCN(c1cccc(OCc2cc(C(F)(F)F)ccc2Cl)c1)S(=O)(=O)c1cccc(C(F)(F)F)c1] | N-(3-((2-chloro-5-(trifluoromethyl)benzyl)oxy) phenyl)-N-ethyl-3-(trifluoromethyl) benzenesulfonamide | 538 (M + H)+ |

TABLE 3-continued

| No. | Structure | Chemical Name | Observed m/z |
|---|---|---|---|
| 2N | 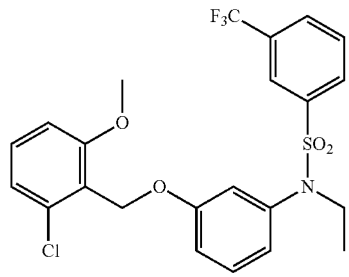 [SMILES: CCN(c1cccc(OCc2c(Cl)cccc2OC)c1)S(=O)(=O)c1cccc(C(F)(F)F)c1] | N-(3-((2-chloro-6-methoxybenzyl) oxy)phenyl)-N-ethyl-3-(trifluoromethyl) benzenesulfonamide | 500 (M + H)+ |
| 2O | 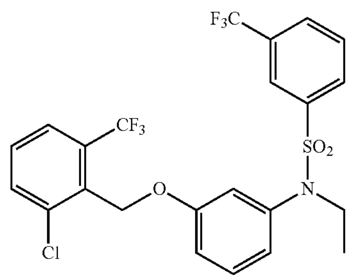 | N-ethyl-N-(3-((2-fluoro-6-(trifluoromethyl)benzyl)oxy) phenyl)-3-(trifluoromethyl) benzenesulfonamide | 532 (M + H)+ |
| 2P | 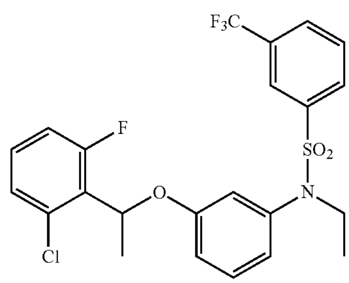 | N-(3-(1-(2-chloro-6-fluorophenyl) ethoxy)phenyl)-N-ethyl-3-(trifluoromethyl) benzenesulfonamide | 502 (M + H)+ |
| 2Q | 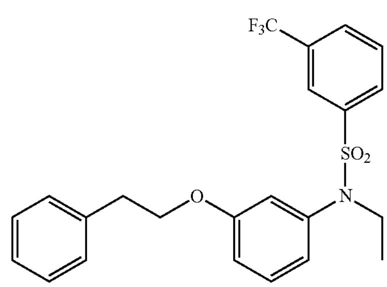 [SMILES: CCN(c1cccc(OCCc2ccccc2)c1)S(=O)(=O)c1cccc(C(F)(F)F)c1] | N-ethyl-N-(3-phenethoxyphenyl)-3-(trifluoromethyl) benzenesulfonamide | 450 (M + H)+ |
| 2R | 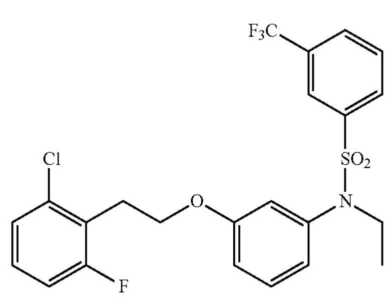 [SMILES: CCN(c1cccc(OCCc2c(F)cccc2Cl)c1)S(=O)(=O)c1cccc(C(F)(F)F)c1] | N-(3-(2-chloro-6-fluorophenethoxy)phenyl)-N-ethyl-3-(trifluoromethyl) benzenesulfonamide | 502 (M + H)+ |

TABLE 3-continued

| No. | Structure | Chemical Name | Observed m/z |
|---|---|---|---|
| 2S | 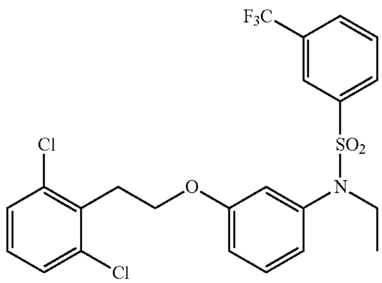 [SMILES: CCN(c1cccc(OCCc2c(Cl)cccc2Cl)c1)S(=O)(=O)c1cccc(C(F)(F)F)c1] | N-(3-(2,6-dichlorophenethoxy)phenyl)-N-ethyl-3-(trifluoromethyl)benzene-sulfonamide | 518 (M + H)+ |
| 2T | 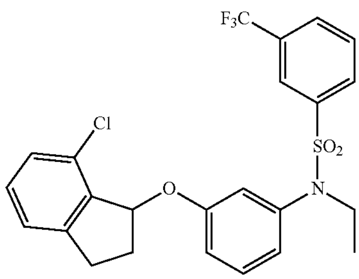 [SMILES: CCN(c1cccc(OC2CCc3cccc(Cl)c32)c1)S(=O)(=O)c1cccc(C(F)(F)F)c1] | N-(3-((7-chloro-2,3-dihydro-1H-inden-1-yl)oxy)phenyl)-N-ethyl-3-(trifluoromethyl)benzenesulfonamide | 496 (M + H)+ |
| 2U | 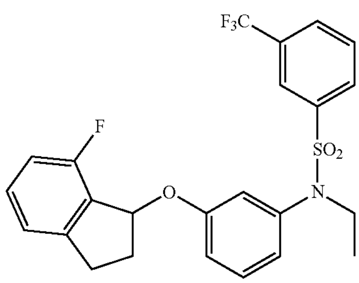 [SMILES: CCN(c1cccc(OC2CCc3cccc(F)c32)c1)S(=O)(=O)c1cccc(C(F)(F)F)c1] | N-ethyl-N-(3-((7-fluoro-2,3-dihydro-1H-inden-1-yl)oxy)phenyl)-3-(trifluoromethyl)benzenesulfonamide | 480 (M + H)+ |
| 2V | 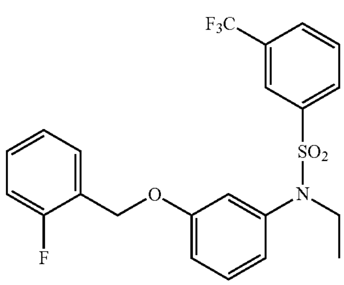 [SMILES: CCN(c1cccc(OCc2ccccc2F)c1)S(=O)(=O)c1cccc(C(F)(F)F)c1] | N-ethyl-N-(3-((2-fluorobenzyl)oxy)phenyl)-3-(trifluoromethyl)benzenesulfonamide | 454 (M + H)+ |
| 2W | 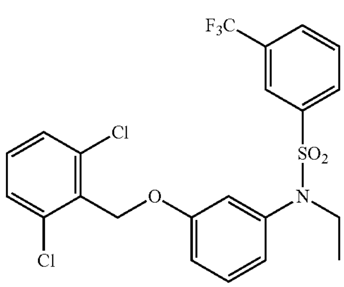 [SMILES: CCN(c1cccc(OCc2c(Cl)cccc2Cl)c1)S(=O)(=O)c1cccc(C(F)(F)F)c1] | N-(3-((2,6-dichlorobenzyl)oxy)phenyl)-N-ethyl-3-(trifluoromethyl)-benzenesulfonamide | 504 (M + H)+ |

Example 3

Synthesis of 1-(Benzyloxy)-3-(1-((4-chlorophenyl) sulfonyl)propyl)benzene

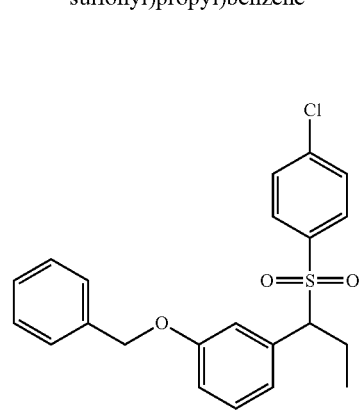

Part I—Synthesis of (1-(3-(Benzyloxy)phenyl)propyl)(4-chlorophenyl)sulfane

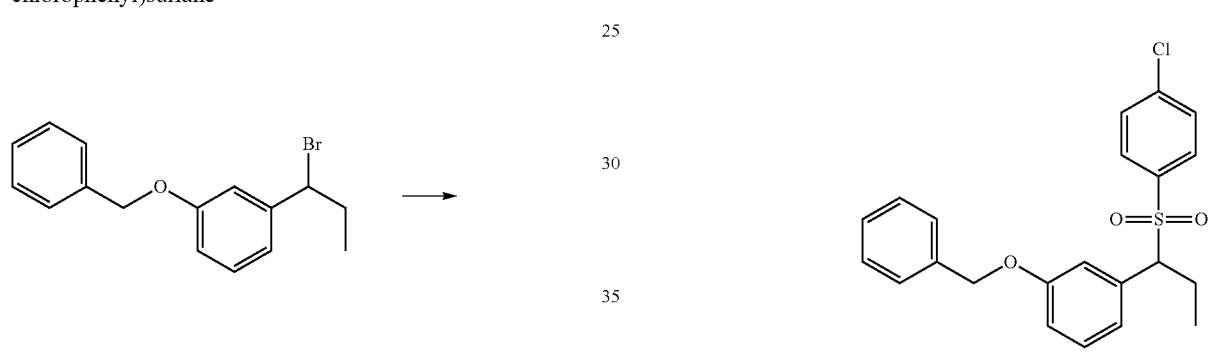

To a mixture of 4-chlorobenzene-1-thiol (570 mg, 3.94 mmol), acetone (20 mL), and potassium carbonate (1.63 g, 11.8 mmol) was added 1-(benzyloxy)-3-(1-bromopropyl) benzene (1.2 g, 3.93 mmol). The mixture was stirred for three hours at room temperature. Water (100 mL) was added to the reaction mixture, and the resulting aqueous mixture was then extracted three times with ethyl acetate. The organic layers from the extractions were combined and then washed with brine, dried ($Na_2SO_4$), and concentrated to provide a residue. The residue was purified via MPLC eluting with a gradient of petroleum ether and ethyl acetate to afford (1-(3-(benzyloxy)phenyl)propyl)(4-chlorophenyl) sulfane (1.2 g, 83%) as a light yellow oil.

Part II—Synthesis of 1-(Benzyloxy)-3-(1-((4-chlorophenyl) sulfonyl)propyl)benzene To a solution of (1-(3-(benzyloxy)phenyl)propyl)(4-chlorophenyl)sulfane (1.00 g, 2.71 mmol) in dichloromethane (20 mL) was added meta-chloroperbenzoic acid (1.17 g, 6.78 mmol) at 0° C. The mixture was stirred for two hours at room temperature, and then quenched by the addition of water (100 mL). The resulting solution was extracted three times with dichloromethane. The organic layers from the extraction were combined and then washed three times with saturated sodium bicarbonate, brine, dried ($Na_2SO_4$), and concentrated to provide a residue. The residue was purified via MPLC eluting with a gradient of petroleum ether and ethyl acetate to afford 1-(benzyloxy)-3-(1-((4-chlorophenyl) sulfonyl)propyl)benzene (1.0 g, 92%) as a light yellow oil. $^1$H-NMR (400 MHz, $CDCl_3$) δ 7.43 (m, 6H), 7.38 (m, 3H), 7.16 (t, 1H), 6.92 (m, 1H), 6.78 (s, 1H), 6.68 (d, 1H), 5.0 (m, 2H), 3.91 (m, 1H), 2.48 (m, 1H), 2.13 (m, 1H), 0.89 (t, 3H). (ES, m/z): $(M+NH_4)^+$ 418.

Example 4

Preparation of Additional 1-(Benzyloxy)-3- or 4-(1-((aryl or heteroaryl)sulfonyl)alkyl)benzenes Compounds in Table 4 were prepared based on experimental procedures described in Example 3 and in the detailed description.

TABLE 4

| No. | Structure | Chemical Name | Observed m/z |
|---|---|---|---|
| 4A | 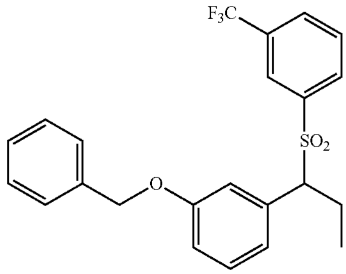 [SMILES: CCC(c1cccc(OCc2ccccc2)c1)S(=O)(=O)c1cccc(C(F)(F)F)c1] | 1-(benzyloxy)-3-(1-((3-(trifluoromethyl)phenyl)-sulfonyl)propyl)benzene | 435 (M + H)+ |
| 4B | 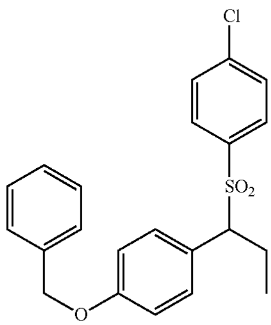 [SMILES: CCC(c1ccc(OCc2ccccc2)cc1)S(=O)(=O)c1ccc(Cl)cc1] | 1-(benzyloxy)-4-(1-((4-chlorophenyl)sulfonyl)propyl)benzene | 401 (M + H)+ |
| 4C | 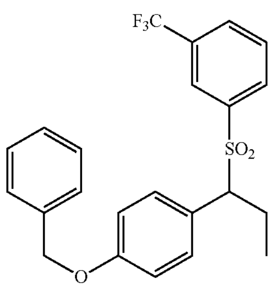 [SMILES: CCC(c1ccc(OCc2ccccc2)cc1)S(=O)(=O)c1cccc(C(F)(F)F)c1] | 1-((1-(4-(benzyloxy)phenyl)-propyl)sulfonyl)-3-(trifluoromethyl)benzene | 435 (M + H)+ |

Example 5

Synthesis of 1-Chloro-2-((3-(1-((4-chlorophenyl)sulfonyl)propyl)-phenoxy)methyl)-3-fluorobenzene

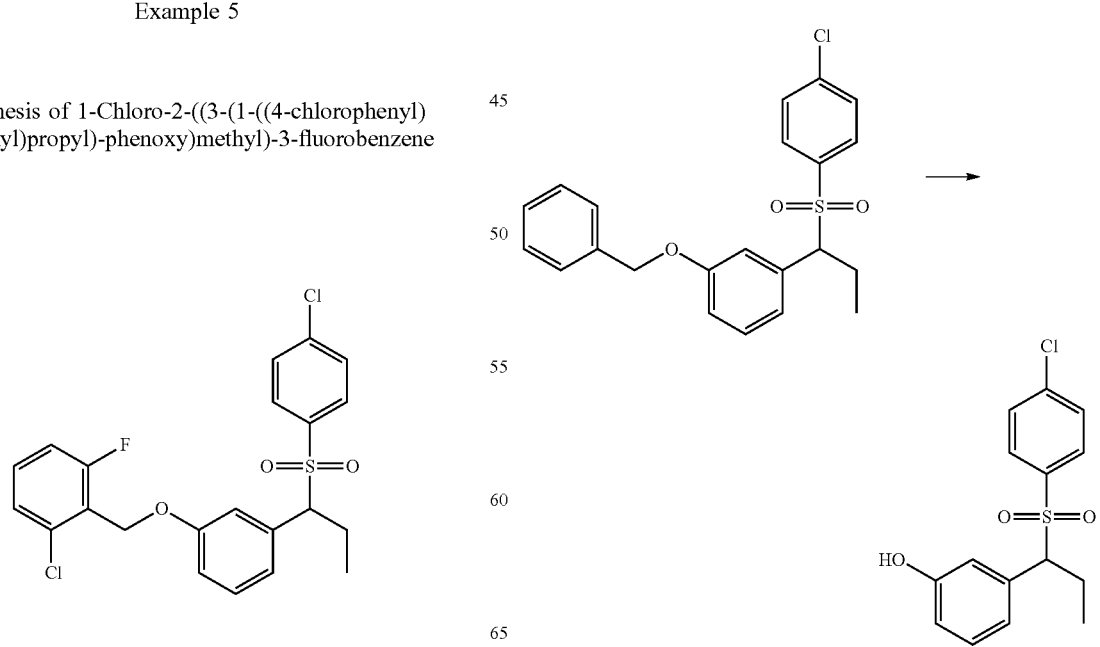

Part I—Synthesis of 3-(1-((4-Chlorophenyl)sulfonyl)propyl)phenol

To a solution 1-(benzyloxy)-3-(1-((4-chlorophenyl)sulfonyl)propyl)benzene (500 mg, 1.25 mmol) in tetrahydrofuran (10 mL) purged with nitrogen was added 10% palladium hydroxide (250 mg). The atmosphere above the reaction was replaced with an atmosphere of hydrogen, and the reaction mixture was stirred for a half hour. Then, the mixture was filtered through celite, and the filtrate was concentrated to provide a residue. The residue was purified via MPLC eluting with ethyl acetate and petroleum ether (1:2) to afford 3-(1-((4-chlorophenyl)sulfonyl)propyl)phenol (300 mg, 77%) as a colorless oil.

Part II—Synthesis of 1-Chloro-2-((3-(1-((4-chlorophenyl)sulfonyl)propyl)phenoxy)methyl)-3-fluorobenzene

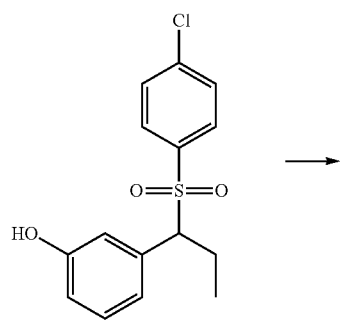

→

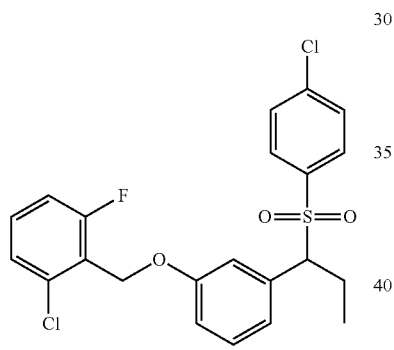

To a solution of 3-(1-((4-chlorophenyl)sulfonyl)propyl)phenol (150 mg, 0.48 mmol), tetrahydrofuran (5 mL), (2-chloro-6-fluorophenyl)methanol (77.5 mg, 0.48 mmol), and triphenyl phosphine (152 mg, 0.58 mmol) was added diisopropyl azodicarboxylate (0.115 mL) dropwise with stirring at 0° C. The resulting solution was stirred overnight at room temperature overnight and then concentrated to provide a residue. The residue was initially purified via MPLC eluting with ethyl acetate and petroleum ether (1:2). Concentration of the major UV component afforded a residue, which was further purified by reverse phase preparative HPLC eluting with a gradient of water (containing 0.05% trifluoroacetic acid) and acetonitrile to afford 1-chloro-2-((3-(1-((4-chlorophenyl)sulfonyl)propyl)phenoxy)methyl)-3-fluorobenzene (61.9 mg, 28%) as a colorless oil. $^1$H-NMR (400 MHz, CD$_3$OD) δ 7.54-7.31 (m, 6H), 7.20 (m, 2H), 6.96 (m, 1H), 6.82 (d, 1H), 6.77 (s, 1H), 5.05 (m, 2H), 4.25 (m, 1H), 2.42 (m, 1H), 2.17 (m, 1H), 0.90 (t, 3H). (ES, m/z): (M+NH$_4$)$^+$ 470.

Example 6

Preparation of Additional Substituted 1-(Benzyloxy)-Aryl Sulfones

Compounds in Table 5 were prepared based on experimental procedures described in Example 5 and the detailed description.

TABLE 5

| No. | Structure | Chemical Name | Observed m/z |
|-----|-----------|---------------|--------------|
| 6A  | 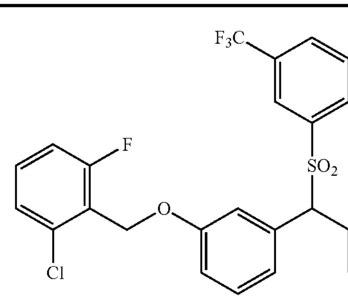          | 1-chloro-3-fluoro-2-((3-(1-((3-(trifluoromethyl)phenyl)-sulfonyl)propyl)phenoxy)methyl)benzene | 487 (M + H)$^+$ |

TABLE 5-continued

| No. | Structure | Chemical Name | Observed m/z |
|---|---|---|---|
| 6B | 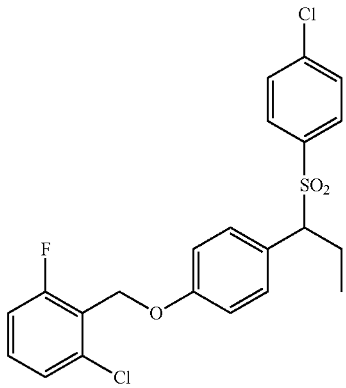 [SMILES: CCC(c1ccc(OCc2c(F)cccc2Cl)cc1)S(=O)(=O)c1ccc(Cl)cc1] | 1-chloro-2-((4-(1-((4-chlorophenyl)-sulfonyl)propyl)phenoxy)methyl)-3-fluorobenzene | 453 (M + H)+ |
| 6C | 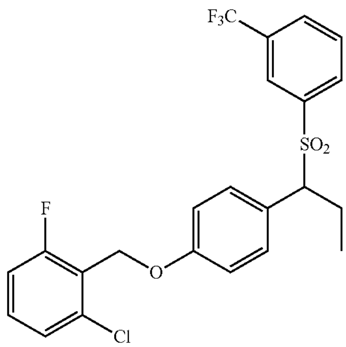 [SMILES: CCC(c1ccc(OCc2c(F)cccc2Cl)cc1)S(=O)(=O)c1cccc(C(F)(F)F)c1] | 1-chloro-3-fluoro-2-((4-(1-((3-(trifluoromethyl)phenyl)-sulfonyl)propyl)phenoxy)methyl)benzene | 487 (M + H)+ |

Example 7

Synthesis of 4-(4-((2-Chloro-6-fluorobenzyl)oxy)-phenyl)-4-((4-chlorophenyl)sulfonyl)-tetrahydro-2H-pyran

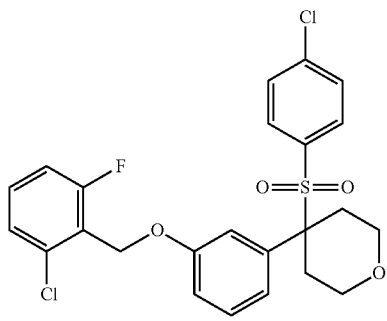 [SMILES: O=S(=O)(c1ccc(Cl)cc1)C1(c2cccc(OCc3c(F)cccc3Cl)c2)CCOCC1]

Part I—Synthesis of (3-((2-Chloro-6-fluorobenzyl)oxy)phenyl)methanol

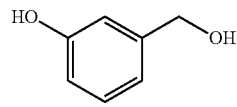

To a mixture of 3-(hydroxymethyl)phenol (1 g, 8.1 mmol), acetone (30 mL), and potassium carbonate (2.26 g, 16.3 mmol) was added 2-(bromomethyl)-1-chloro-3-fluorobenzene (1.98 g, 8.9 mmol). The resulting solution was stirred overnight at 60° C. with the reaction vessel placed in an oil bath. The resulting reaction solution was diluted with water, and extracted three times with dichloromethane. The organic layers from the extraction were combined and concentrated to provide a residue. The residue was purified via MPLC eluting with a gradient of petroleum ether and ethyl acetate to afford (3-((2-chloro-6-fluorophenyl)methoxy)phenyl) methanol (1.42 g, 66%) as a colorless oil.

Part II—Synthesis of 2-((3-(Bromomethyl)phenoxy)methyl)-1-chloro-3-fluorobenzene

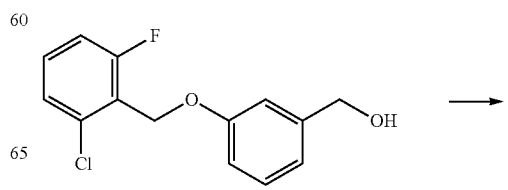

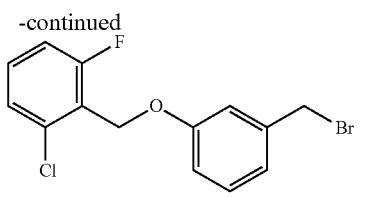

To a solution of (3-((2-chloro-6-fluorophenyl)methoxy)phenyl)methanol (1.22 g, 4.6 mmol) in dichloromethane (14 mL) was added phosphorous tribromide (0.2 mL, 2.3 mmol). The resulting mixture was stirred for thirty minutes at room temperature. Then, water was added to the mixture to quench the reaction, and the resulting mixture was extracted with dichloromethane three times. The organic extracts were combined and then concentrated to afford 2-((3-(bromomethyl)phenoxy)methyl)-1-chloro-3-fluorobenzene (1.03 g, 68%) as a yellow oil.

Part III—Synthesis of (3-((2-Chloro-6-fluorobenzyl)oxy)benzyl)(4-chlorophenyl)sulfane

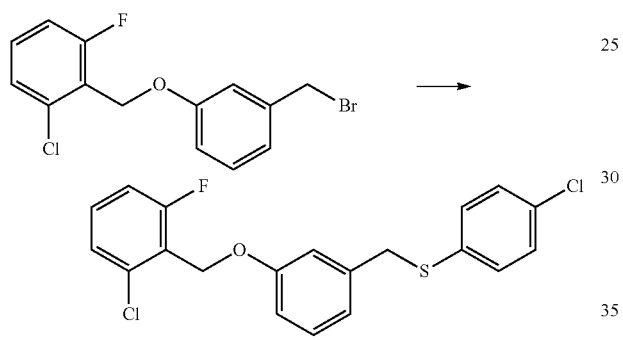

To a mixture of 4-chlorobenzene-1-thiol (453 mg, 3.13 mmol), acetone (20 mL), and potassium carbonate (744 mg, 5.38 mmol, 1.50 equiv) was added 2-((3-(bromomethyl)phenoxy)methyl)-1-chloro-3-fluorobenzene (1.03 g, 3.13 mmol). The mixture was stirred overnight at room temperature, filtered, and concentrated to provide a residue. The residue was purified via MPLC eluting with a gradient of petroleum ether and ethyl acetate to afford (3-((2-chloro-6-fluorobenzyl)oxy)benzyl)(4-chlorophenyl)sulfane (1.09 g, 89%) as a colorless oil.

Part IV—Synthesis of 1-Chloro-2-((3-(((4-chlorophenyl)sulfonyl)methyl)phenoxy)methyl)-3-fluorobenzene

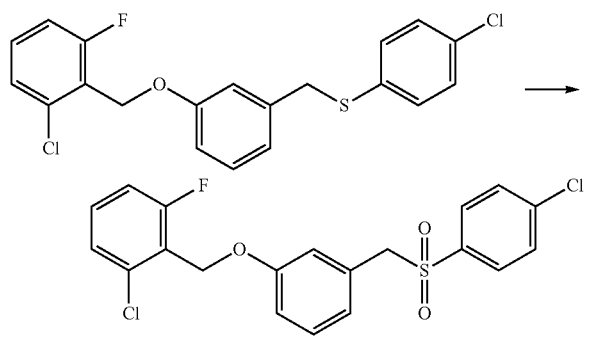

To a solution of (3-((2-chloro-6-fluorobenzyl)oxy)benzyl)(4-chlorophenyl)sulfane (1.09 g, 2.77 mmol) in dichloromethane (30 mL) was added meta-chloroperbenzoic acid (1.4 g, 8.3 mmol). The reaction mixture was stirred two hours at room temperature. Next, water was added, and the resulting mixture was extracted three times with dichloromethane. The organic layers from the extraction were combined and then concentrated to provide a residue. The residue was purified by MPLC eluting with a gradient of petroleum ether and ethyl acetate to afford 1-chloro-2-((3-(((4-chlorophenyl)sulfonyl)methyl)phenoxy)methyl)-3-fluorobenzene (1.35 g, 115%) as a white solid.

Part V—Synthesis of 4-(3-((2-chloro-6-fluorobenzyl)oxy)phenyl)-4-((4-chlorophenyl)sulfonyl)tetrahydro-2H-pyran

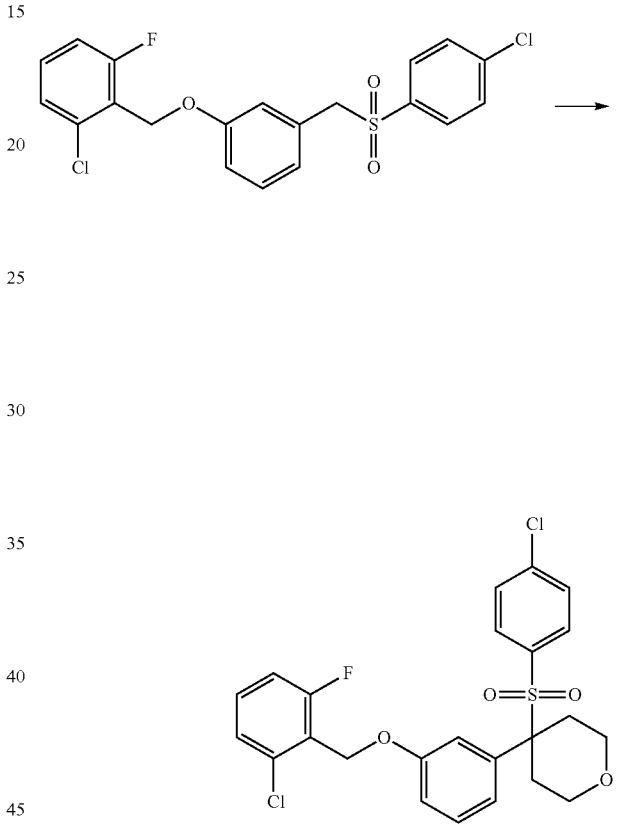

A mixture of 1-chloro-2-((3-(((4-chlorophenyl)sulfonyl)methyl)phenoxy)methyl)-3-fluorobenzene (203 mg, 0.48 mmol), N,N-dimethylformamide (1.8 mL), 1-bromo-2-(2-bromoethoxy)ethane (0.0662 mL, 0.53 mmol), and sodium hydride (42.1 mg, 1.75 mmol) was stirred for an hour at room temperature. Next, water was added water (25 mL), and the resulting mixture was extracted three times with dichloromethane. The organic layers from the extraction were combined and then concentrated to provide a residue. The residue was purified by reverse phase preparative HPLC eluting with a gradient water with 0.05% trifluoroacetic acid and acetonitrile to afford 4-(3-(2-chloro-6-fluorobenzyl)oxy)phenyl)-4-(4-chlorophenyl)sulfonyl)tetrahydro-2H-pyran (78 mg, 33%) as a white solid. $^1$H-NMR (400 MHz, CDCl$_3$) δ 7.32-7.29 (m, 5H), 7.21 (d, J=8.4 Hz, 2H), 7.08-7.00 (m, 2H), 6.91 (d, J=8.1 Hz, 1H), 6.70 (s, 1H), 5.10 (s, 1H), 3.96 (d, J=10.2 Hz, 2H), 3.33 (t, J=10.8 Hz, 2H), 2.62 (dt, J=13.8 Hz, 4.5 Hz, 2H), 2.36 (d, J=14.4 Hz, 2H). (ES, m/z): (M+NH$_4$)$^+$ 512.

Example 8

Preparation of Additional 4-(3-((2-Chloro-6-fluorobenzyl)oxy)-phenyl)-4-((3-(trifluoromethyl)phenyl)-sulfonyl)tetrahydro-2H-pyran

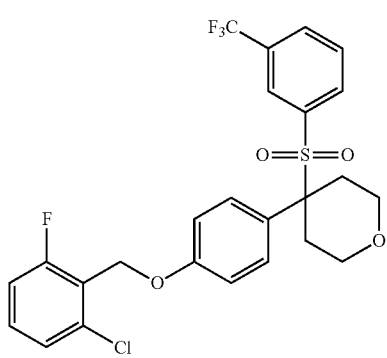 [SMILES: O=S(=O)(c1cccc(C(F)(F)F)c1)C1(c2ccc(OCc3c(F)cccc3Cl)cc2)CCOCC1]

The title compound was prepared based on experimental procedures described in Example 7 and the detailed description. (ES, m/z): (M+NH$_4$)$^+$ 546.

Example 9

Synthesis of N-(3-((2-Chlorobenzyl)amino)phenyl)-N-ethyl-3-(trifluoromethyl)benzenesulfonamide

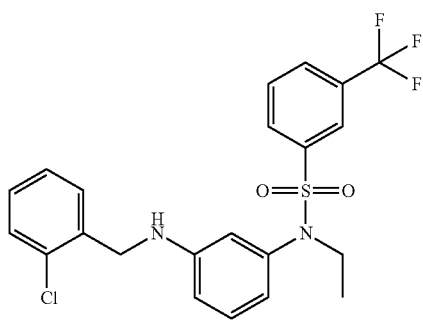 [SMILES: CCN(c1cccc(NCc2ccccc2Cl)c1)S(=O)(=O)c1cccc(C(F)(F)F)c1]

Part I—Synthesis of N-(3-Bromophenyl)-3-(trifluoromethyl)benzenesulfonamide

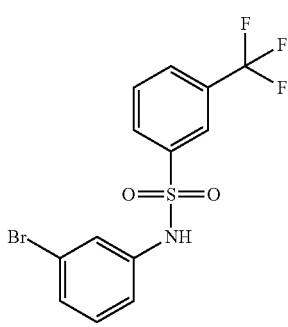 [SMILES: O=S(=O)(Nc1cccc(Br)c1)c1cccc(C(F)(F)F)c1]

To 3-bromoaniline (1.58 g, 9.19 mmol) in pyridine (20 mL) was added 3-(trifluoromethyl)benzenesulfonyl chloride (1.62 mL, 10.1 mmol) and heated to 50° C. overnight. Then, the reaction mixture was cooled, diluted with ethyl acetate, and then washed with 1 M hydrochloric acid (3×), brine, dried with anhydrous sodium sulfate, filtered and concentrated onto silica. The mixture was purified by column chromatography eluting with a gradient of ethyl acetate in hexanes. Pure fractions were combined and concentrated to yield title compound (3.57 g, quantitative yield).

Part II—Synthesis of N-(3-Bromophenyl)-N-ethyl-3-(trifluoromethyl)benzenesulfonamide

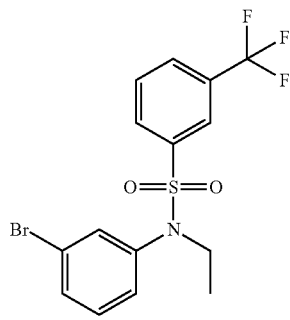 [SMILES: CCN(c1cccc(Br)c1)S(=O)(=O)c1cccc(C(F)(F)F)c1]

To N-(3-bromophenyl)-3-(trifluoromethyl)benzenesulfonamide (3.5 g, 9.2 mmol) in N,N-dimethylformamide (40 mL) was added potassium carbonate (1.9 g, 13.8 mmol) followed by ethyl bromide (1.03 mL, 13.8 mmol). The reaction was stirred at ambient temperature overnight. Then, the resulting suspension was partitioned between ethyl acetate and water, washed with brine, dried with sodium sulfate, filtered and concentrated to provide a mixture that was purified by column chromatography eluting with a gradient of ethyl acetate in hexanes. Pure fractions were combined and concentrated to yield title compound (1.82 g, 48%).

Part III—Synthesis of N-(3-((2-Chlorobenzyl)amino)phenyl)-N-ethyl-3-(trifluoromethyl)benzenesulfonamide

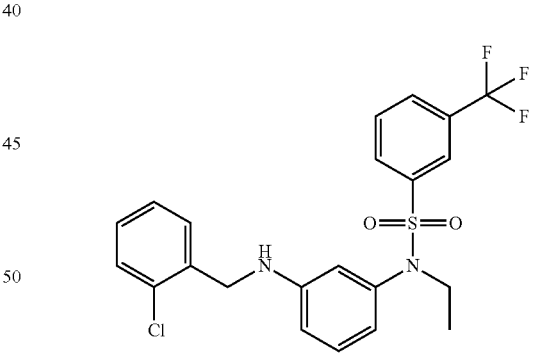

In a microwave tube was combined N-(3-bromophenyl)-N-ethyl-3-(trifluoromethyl)benzenesulfonamide (100 mg, 0.25 mmol), 2-chlorobenzylamine (59 µL, 0.49 mmol), potassium phosphate tribasic (156 mg, 0.74 mmol), 2-dicyclohexylphosphino-2',4',6'-triisopropylbiphenyl (6 mg, 0.01 mmol), and tris(benzylideneacetone)dipalladium (0) (5 mg, 0.01 mmol). To the solids was added toluene (2 mL) and water (0.5 mL), then the resulting mixture was heated to 130° C. in a microwave for 1 hour. Next, the reaction mixture was partitioned between ethyl acetate and brine, dried with anhydrous sodium sulfate, filtered and concentrated to provide a mixture that was purified by column chromatography eluting with a gradient of 0-40% ethyl acetate in hexanes. Pure fractions were combined and concentrated to yield title compound. (52 mg, 44%). ¹H-NMR (400 MHz, DMSO-d₆) δ 8.05 (d, 1H), 7.87 (d, 1H), 7.78 (t, 1H), 7.68 (s, 1H), 7.39 (m, 1H), 7.30-7.22 (m, 3H), 7.0 (t, 1H), 6.49 (m, 1H), 6.45 (t, 1H), 6.17 (m, 1H), 6.07 (s, 1H), 4.16 (d, 2H), 3.45 (q, 2H), 0.87 (t, 3H).

Example 10

Synthesis of N-(3-((2-Chlorobenzyl)(ethyl)amino)phenyl)-N-ethyl-3-(trifluoromethyl)benzenesulfonamide

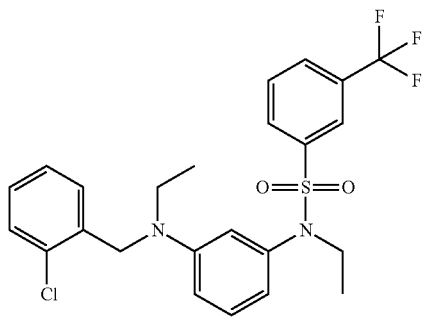 [SMILES: CCN(Cc1ccccc1Cl)c1cccc(N(CC)S(=O)(=O)c2cccc(C(F)(F)F)c2)c1]

To N-(3 #2-chlorobenzyl)amino)phenyl)-N-ethyl-3-(trifluoromethyl)benzenesulfonamide (41 mg, 0.087 mmol) in anhydrous N,N-dimethylformamide (0.5 mL) was added ethyl bromide (10 μL, 0.13 mmol) and sodium hydride (60% in mineral oil, 3 mg, 0.1 mmol). The reaction mixture was stirred at ambient temperature for 2 hours. Next, an additional amount of ethyl bromide (3 mg, 0.13 mmol) was added along with sodium hydride (60% in mineral oil, 3 mg, 0.1 mmol) and tetrabutylammonium iodide (3 mg). Then, the reaction mixture was stirred for 2 days. Next, methanol (0.5 mL) was added to the reaction mixture to quench the reaction. The resulting mixture was purified by preparatory HPLC. Pure fractions were combined and concentrated to yield title compound (13 mg, 30%). ¹H-NMR (400 MHz, DMSO-d₆) δ 8.05 (d, 1H), 7.89 (d, 1H), 7.79 (t, 1H), 7.65 (s, 1H), 7.42 (m, 1H), 7.22 (m, 2H), 7.20 (t, 1H), 6.97 (m, 1H), 6.54 (m, 1H), 6.28 (m, 1H), 5.93 (m, 1H), 4.36 (s, 2H), 3.45 (q, 2H), 3.3 (q, 2H), 1.01 (t, 3H), 0.85 (t, 3H).

Example 11

Synthesis of N-(3-(((2-Chlorobenzyl)amino)methyl)phenyl)-N-ethyl-3-(trifluoromethyl)benzenesulfonamide

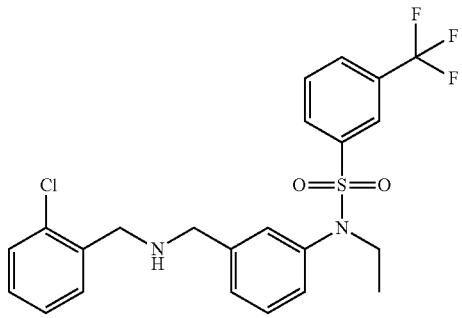 [SMILES: CCN(c1cccc(CNCc2ccccc2Cl)c1)S(=O)(=O)c1cccc(C(F)(F)F)c1]

Part I—Synthesis of Methyl 3-((3-(trifluoromethyl)phenyl)sulfonamido)benzoate

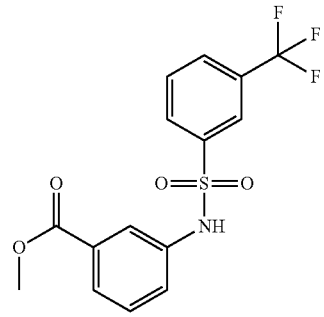 [SMILES: COC(=O)c1cccc(NS(=O)(=O)c2cccc(C(F)(F)F)c2)c1]

To methyl 3-aminobenzoate (1.5 g, 9.9 mmol) in pyridine (20 mL) was added 3-(trifluoromethyl)benzenesulfonyl chloride (1.75 mL, 10.9 mmol). The resulting mixture was heated to 50° C. overnight. Then, the reaction mixture was cooled, diluted with ethyl acetate, washed with 1 M hydrochloric acid (3×), brine, dried with anhydrous sodium sulfate, filtered and concentrated onto silica. The mixture was purified by column chromatography eluting with a gradient of ethyl acetate in hexanes. Fractions containing the title compound in pure form were combined and concentrated to yield title compound (3.22 g, 90%).

Part II—Synthesis of Methyl 3-((N-ethyl-3-(trifluoromethyl)phenyl)sulfonamido)benzoate

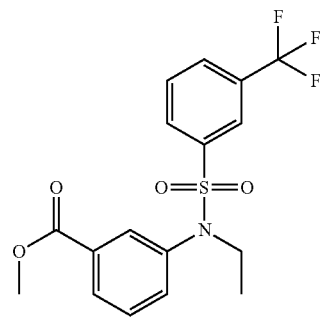 [SMILES: CCN(c1cccc(C(=O)OC)c1)S(=O)(=O)c1cccc(C(F)(F)F)c1]

To methyl 3-((3-(trifluoromethyl)phenyl)sulfonamido)benzoate (3.2 g, 8.9 mmol) in N,N-dimethylformamide (30 mL) was added potassium carbonate (2.5 g, 17.8 mmol) followed by ethyl bromide (1.3 mL, 17.8 mmol). The resulting mixture was stirred at ambient temperature overnight. Then, the reaction mixture was diluted with ethyl acetate, washed with water (3×), brine, dried with anhydrous sodium sulfate, filtered and concentrated to provide a mixture that was purified by column chromatography eluting with a gradient of 0-50% ethyl acetate in hexanes. Fractions containing the title compound in pure form were combined and concentrated to provide the title compound (3.35 g, 97%).

Part III—Synthesis of 3-((N-Ethyl-3-(trifluoromethyl)phenyl)sulfonamido)benzoic acid

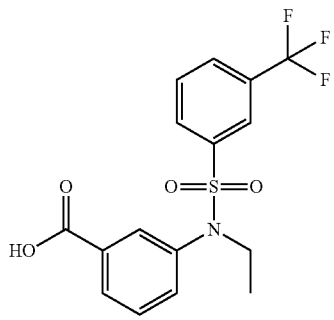 [SMILES: CCN(c1cccc(C(=O)O)c1)S(=O)(=O)c1cccc(C(F)(F)F)c1]

To a solution of methyl 3-((N-ethyl-3-(trifluoromethyl)phenyl)sulfonamido)benzoate (1.03 g, 2.7 mmol) in methanol (15 mL) was added 2M sodium hydroxide (2.7 mL, 5.4 mmol). The resulting mixture was stirred at ambient temperature over the weekend. Then, 1 M hydrochloric acid was added to the reaction mixture in order to acidify the reaction mixture. A solid precipitated. The reaction mixture was diluted further with water, slurried, then a white solid was isolated by filtration. The white solid was dried in a vacuum oven to provide the title compound (850 mg, 86%).

Part IV—Synthesis of 3-((N-Ethyl-3-(trifluoromethyl)phenyl)sulfonamido)benzoyl chloride

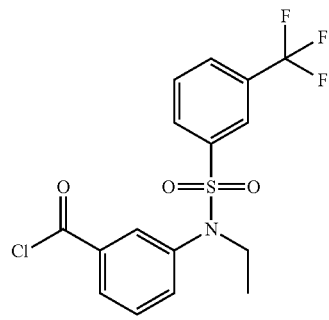 [SMILES: CCN(c1cccc(C(=O)Cl)c1)S(=O)(=O)c1cccc(C(F)(F)F)c1]

To 3-((N-ethyl-3-(trifluoromethyl)phenyl)sulfonamido) benzoic acid (0.4 g, 1.1 mmol) in dichloromethane (10 mL) was added oxalyl chloride (0.18 mL, 2.1 mmol) and 1 drop anhydrous N,N-dimethylformamide. The reaction mixture was stirred at ambient temperature overnight. Then, the reaction mixture was concentrated. Next, the reaction mixture was azeotroped with chloroform three times to provide the title compound (420 mg, 100%).

Part V—Synthesis of N-(2-Chlorobenzyl)-3-4N-ethyl-3-(trifluoromethyl)phenyl-)sulfonamido)benzamide

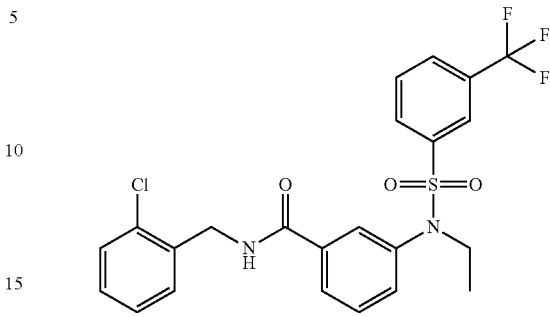

To a solution of 3-((N-ethyl-3-(trifluoromethyl)phenyl) sulfonamido)benzoyl chloride (50 mg, 0.13 mmol) in dichloromethane (0.5 mL) was added N,N-diisopropylethylamine (33 mg, 0.26 mmol) followed by 2-chlorobenzylamine (22 mg, 0.15 mmol). The reaction mixture was stirred at ambient temperature for 30 minutes. Then, the reaction mixture was subjected to column chromatography eluting with a gradient of 0-50% ethyl acetate in hexanes. Fractions containing the title compound in pure form were combined and concentrated to provide the title compound (50 mg, 79%). $^1$H-NMR (400 MHz, DMSO-$d_6$) δ 9.02 (t, 1H), 8.09 (d, 1H), 7.91-7.82 (m, 3H), 7.64 (s, 1H), 7.55 (s, 1H), 7.51-7.42 (m, 2H), 7.28 (m, 4H), 4.49 (d, 2H), 3.63 (q, 2H), 0.97 (t, 3H).

Part VI—Synthesis of N-(3-(((2-Chlorobenzyl)amino) methyl)phenyl)-N-ethyl-3-(trifluoromethyl)benzenesulfonamide

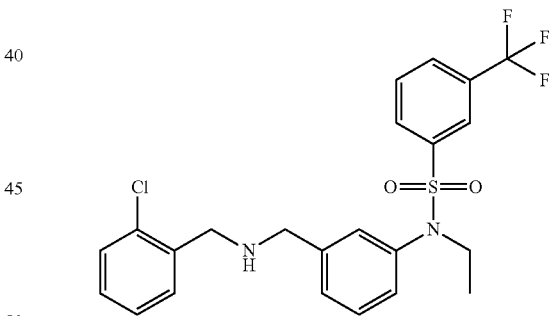

To N-(2-chlorobenzyl)-3-((N-ethyl-3-(trifluoromethyl) phenyl)sulfonamido)-benzamide (40 mg, 0.08 mmol) in a vial in anhydrous tetrahydrofuran (0.5 mL) was added borane-methyl sulfide complex (32 μL, 0.32 mmol). The resulting solution was then heated to 60° C. for 4 hours. Then, the reaction mixture was cooled. Next, the reaction was carefully quenched by adding methanol (1 mL) to the reaction mixture. The resulting mixture was heated to 60° C. for 20 minutes, then concentrated to provide a mixture that was purified by preparatory HPLC. Fractions containing the title compound in pure form were combined and concentrated to yield title compound (35 mg, 90%). $^1$H-NMR (400 MHz, DMSO-$d_6$) δ 9.3 (bs, 2H), 8.10 (d, 1H), 7.92 (d, 1H), 7.84 (t, 1H), 7.58-7.39 (m, 7H), 7.04 (m, 1H), 4.26 (bm, 2H), 4.20 (bm, 2H), 3.61 (q, 2H), 0.97 (t, 3H).

Example 12

Preparation of N-(3-(((2-Chlorophenyl)amino)methyl)-phenyl)-N-ethyl-3-(trifluoromethyl)-benzenesulfonamide

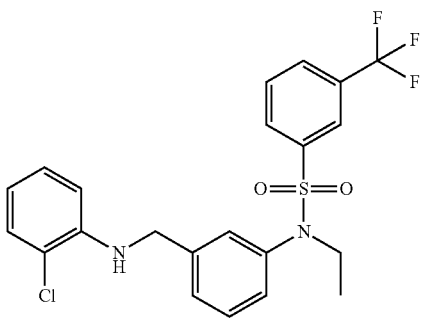

The title compound was prepared based on experimental procedures described in Example 11 and the detailed description. (ES, m/z): (M+H)+ 469.

Example 13

Synthesis of N-(3-(((2-Chlorophenyl)(ethyl)amino)methyl)phenyl)-N-ethyl-3-(trifluoromethyl)benzenesulfonamide

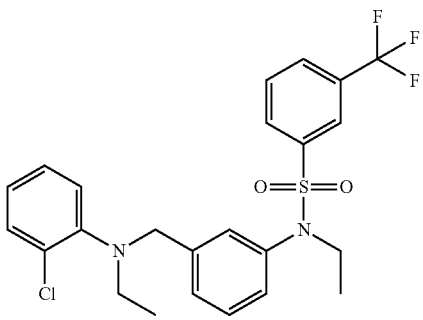 [SMILES: CCN(Cc1cccc(N(CC)S(=O)(=O)c2cccc(C(F)(F)F)c2)c1)c1ccccc1Cl]

To a solution N-(3-(((2-chlorophenyl)amino)methyl)phenyl)-N-ethyl-3-(trifluoromethyl)benzenesulfonamide (18 mg, 0.04 mmol) and ethyl bromide (6 μL, 0.08 mmol) in anhydrous N,N-dimethylformamide (0.5 mL) was added sodium hydride (60% in mineral oil, 6 mg, 0.15 mmol). The resulting mixture was stirred at ambient temperature overnight. Then, methanol (0.5 mL) was added to the reaction mixture to quench the reaction. The resulting mixture was purified by preparatory HPLC. Fractions containing the title compound in pure form were combined and concentrated to provide the title compound (7 mg, 33%). ESI (M+H)+ 497.02, 499.03.

Example 14

Synthesis of N-Ethyl-N-(3-(indolin-1-ylmethyl)phenyl)-3-(trifluoromethyl)benzenesulfonamide

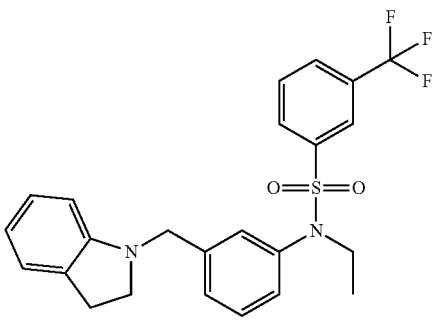 [SMILES: CCN(c1cccc(CN2CCc3ccccc32)c1)S(=O)(=O)c1cccc(C(F)(F)F)c1]

Part I—Synthesis of N-Ethyl-N-(3-(hydroxymethyl)phenyl)-3-(trifluoromethyl)benzenesulfonamide

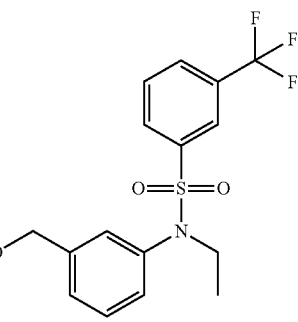

To 3-((N-ethyl-3-(trifluoromethyl)phenyl)sulfonamido)benzoic acid (0.2 g, 0.54 mmol) in anhydrous tetrahydrofuran (5 mL) under nitrogen was carefully added borane-methyl sulfide complex (0.21 mL, 2.1 mmol). The resulting mixture was heated to 65° C. for 4 hours. Then, reaction mixture was cooled to ambient temperature, the reaction was carefully quenched by adding methanol (10 mL) to the reaction mixture, then heating the resulting mixture to 65° C. for 30 minutes. Next, the reaction mixture was stirred at ambient temperature overnight. Then, the reaction mixture was concentrated, and the resulting concentrate was dissolved in ethyl acetate to provide a mixture that was washed with water, brine, dried with anhydrous sodium sulfate, filtered and concentrated to provide the title compound (190 mg, 99%).

Part II—Synthesis of N-(3-(Bromomethyl)phenyl)-N-ethyl-3-(trifluoromethyl)benzenesulfonamide

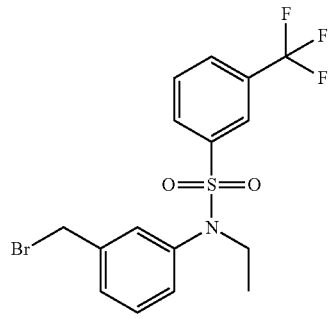 [SMILES: CCN(c1cccc(CBr)c1)S(=O)(=O)c1cccc(C(F)(F)F)c1]

To a solution of N-ethyl-N-(3-(hydroxymethyl)phenyl)-3-(trifluoromethyl)benzenesulfonamide (0.18 g, 0.5 mmol) in anhydrous tetrahydrofuran (4 mL) was added triphenylphosphine (0.14 g, 0.55 mmol) followed by carbon tetrabromide (0.18 g, 0.55 mmol) in one portion. The resulting mixture was stirred at ambient temperature for 2 hours. Next, liquids were decanted off and the resulting liquid was concentrated to provide a mixture that was purified by column chromatography eluting with a gradient of 0-50% ethyl acetate in hexanes. Fractions containing the title compound in pure form were combined and concentrated to provide the title compound (67 mg, 32%).

Part III—Synthesis of N-Ethyl-N-(3-(indolin-1-ylmethyl)phenyl)-3-(trifluoromethyl)benzenesulfonamide

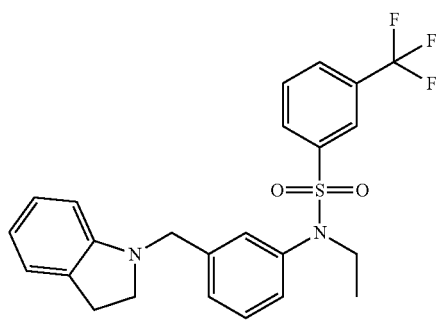 [SMILES: CCN(c1cccc(CN2CCc3ccccc32)c1)S(=O)(=O)c1cccc(C(F)(F)F)c1]

To a solution of N-(3-(bromomethyl)phenyl)-N-ethyl-3-(trifluoromethyl)benzenesulfonamide (65 mg, 0.15 mmol) in anhydrous N,N-dimethylformamide (1.5 mL) under nitrogen at ambient temperature was added indoline (28 mg, 0.23 mmol) followed by 60% sodium hydride (60% in mineral oil, 6 mg, 0.23 mmol). The reaction mixture was stirred at ambient temperature overnight. Then, the reaction was quenched by adding methanol (0.5 mL) to the reaction mixture. The resulting mixture was purified by preparatory HPLC. Fractions containing the title compound in pure form were combined and concentrated to provide the title compound (60 mg, 85%). $^1$H-NMR (400 MHz, DMSO-$d_6$) δ 8.05 (d, 1H), 7.85 (d, 1H), 7.77 (t, 1H), 7.67 (s, 1H), 7.31 (m, 2H), 7.02-6.91 (m, 4H), 6.56 (t, 1H), 6.47 (m, 1H), 4.17 (s, 2H), 3.58 (q, 2H), 3.09 (t, 2H), 2.82 (t, 2H), 0.95 (t, 3H).

Example 15

Synthesis of N-Ethyl-N-(3-((2-oxobenzo[d]oxazol-3(2H)-yl)methyl)phenyl)-3-(trifluoromethyl)benzenesulfonamide

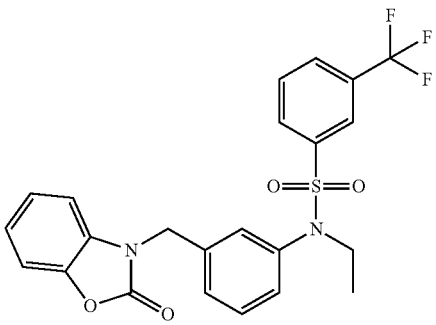 [SMILES: CCN(c1cccc(Cn2c(=O)oc3ccccc32)c1)S(=O)(=O)c1cccc(C(F)(F)F)c1]

To a solution of N-(3-(bromomethyl)phenyl)-N-ethyl-3-(trifluoromethyl)benzenesulfonamide (57 mg, 0.14 mmol) and o-phenylene carbamate (27 mg, 0.2 mmol) in anhydrous N,N-dimethylformamide (0.5 mL) was added sodium hydride (60% in mineral oil, 8 mg, 0.2 mmol). The resulting mixture was stirred at ambient temperature overnight. Then, the reaction was quenched by adding methanol (0.5 mL) to the reaction mixture. The resulting mixture was purified by preparatory HPLC. Fractions containing the title compound were combined and concentrated to provide the title compound (50 mg, 78%). $^1$H-NMR (400 MHz, DMSO-$d_6$) δ 8.00 (d, 1H), 7.75 (d, 1H), 7.69 (m, 1H), 7.64 (m, 1H), 7.33 (m, 3H), 7.13-7.06 (m, 4H), 6.99 (m, 1H), 4.96 (s, 2H), 3.58 (q, 2H), 0.92 (t, 3H).

Example 16

Synthesis of N-(3-((2-Chloro-6-fluorophenoxy)methyl)phenyl)-N-ethyl-3-(trifluoromethyl)benzenesulfonamide

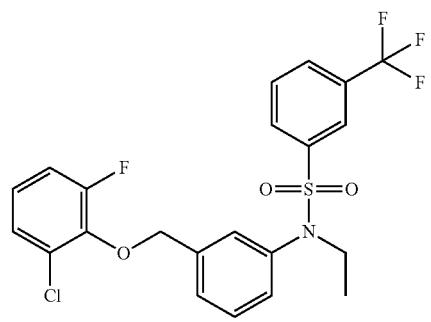 [SMILES: CCN(c1cccc(COc2c(F)cccc2Cl)c1)S(=O)(=O)c1cccc(C(F)(F)F)c1]

To a solution of N-(3-(bromomethyl)phenyl)-N-ethyl-3-(trifluoromethyl)benzenesulfonamide (54 mg, 0.13 mmol) and 2-chloro-6-fluorophenol (28 mg, 0.19 mmol) in anhydrous N,N-dimethylformamide (0.5 mL) was added cesium carbonate (63 mg, 0.19 mmol). The reaction mixture was stirred at ambient temperature for 4 hours. Next, the reaction mixture was diluted with ethyl acetate, and the resulting mixture was washed with water, washed with brine, dried with anhydrous sodium sulfate, filtered and concentrated to provide a mixture that was purified by column chromatography eluting with a gradient of 0-40% ethyl acetate in hexanes. Fractions containing the title compound in pure form were combined and concentrated to provide the title compound (46 mg, 74%). $^1$H-NMR (400 MHz, DMSO-$d_6$) δ 8.05 (d, 1H), 7.89 (d, 1H), 7.81 (m, 1H), 7.64 (s, 1H), 7.40 (m, 2H), 7.26 (m, 2H), 7.12 (m, 2H), 7.01 (d, 1H), 5.05 (s, 2H), 3.57 (q, 2H), 0.92 (t, 3H).

Example 17

Preparation of Additional N-Phenoxymethylphenyl-Benzenesulfonamides and N-Cycloalkoxymethylphenyl-Benzenesulfonamides Compounds in Table 6 were prepared based on experimental procedures described in Example 18 and the detailed description.

TABLE 6

| No. | Structure | Chemical Name | Observed m/z |
|---|---|---|---|
| 17A | 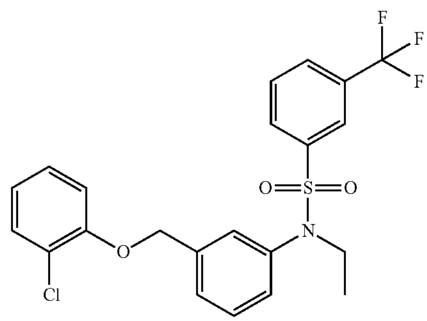 [SMILES: CCN(c1cccc(COc2ccccc2Cl)c1)S(=O)(=O)c1cccc(C(F)(F)F)c1] | N-(3-((2-chlorophenoxy)methyl)phenyl)-N-ethyl-3-(trifluoromethyl)benzene-sulfonamide | 470 (M + H)$^+$ |
| 17B | 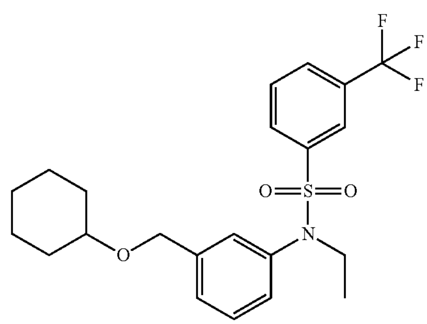 [SMILES: CCN(c1cccc(COC2CCCCC2)c1)S(=O)(=O)c1cccc(C(F)(F)F)c1] | N-(3-((cyclohexyloxy)methyl)phenyl)-N-ethyl-3-(trifluoromethyl)benzene-sulfonamide | 442 (M + H)$^+$ |
| 17C | 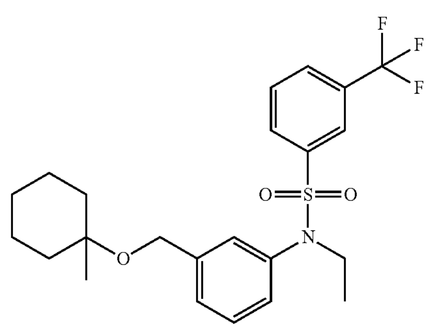 [SMILES: CCN(c1cccc(COC2(C)CCCCC2)c1)S(=O)(=O)c1cccc(C(F)(F)F)c1] | N-ethyl-N-(3-(((1-methyl-cyclohexyl)-oxy)methyl)phenyl)-3-(trifluoromethyl)-benzenesulfonamide | 456 (M + H)$^+$ |
| 17D | 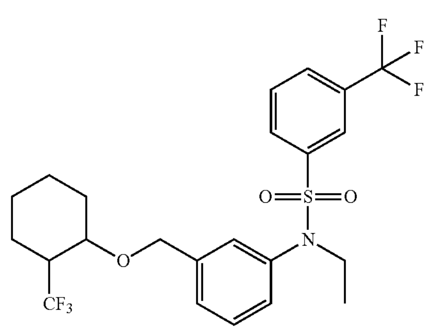 [SMILES: CCN(c1cccc(COC2CCCCC2C(F)(F)F)c1)S(=O)(=O)c1cccc(C(F)(F)F)c1] | N-ethyl-3-(trifluoromethyl)-N-(3-(((2-(trifluoromethyl)cyclohexyl)oxy)methyl)phenyl)benzenesulfonamide | 510 (M + H)$^+$ |

Example 18

Synthesis of N-(3-(1-(2-Chloro-6-fluorophenoxy)ethyl)phenyl)-N-ethyl-3-(trifluoromethyl)benzenesulfonamide

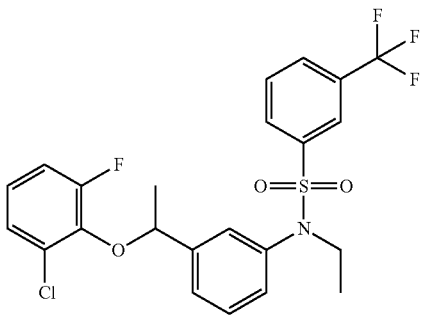 [SMILES: CCN(c1cccc(C(C)Oc2c(F)cccc2Cl)c1)S(=O)(=O)c1cccc(C(F)(F)F)c1]

Part I—Synthesis of 3-((N-Ethyl-3-(trifluoromethyl)phenyl)sulfonamido)-N-methoxy-N-methylbenzamide

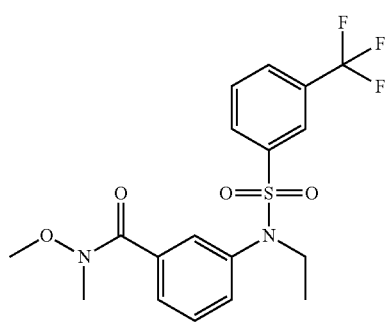 [SMILES: CCN(c1cccc(C(=O)N(C)OC)c1)S(=O)(=O)c1cccc(C(F)(F)F)c1]

To a solution of 3-((N-ethyl-3-(trifluoromethyl)phenyl)sulfonamido)benzoic acid (0.25 g, 0.67 mmol) in acetonitrile (5 mL) was added N-methoxy-N-methyl-1H-imidazole-1-carboxamide (0.21 g, 1.34 mmol). The resulting mixture was heated to reflux overnight. Next, the reaction mixture was cooled solution, then diluted with ethyl acetate, washed with 1 M hydrogen chloride, brine, dried with anhydrous sodium sulfate, filtered and concentrated to provide a mixture that was purified by column chromatography eluting with a gradient of ethyl acetate in hexanes. Fractions containing the title compound in pure form were combined and concentrated to provide the title compound (0.24 g, 86%).

Part II—Synthesis of N-(3-Acetylphenyl)-N-ethyl-3-(trifluoromethyl)benzenesulfonamide

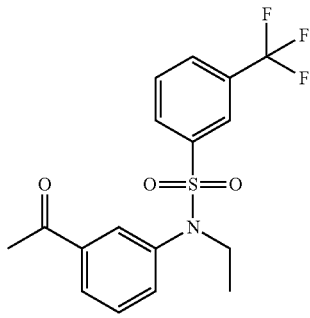 [SMILES: CCN(c1cccc(C(C)=O)c1)S(=O)(=O)c1cccc(C(F)(F)F)c1]

To a solution of 3-((N-ethyl-3-(trifluoromethyl)phenyl)sulfonamido)-N-methoxy-N-methylbenzamide (0.2400 g, 0.5764 mmol) in anhydrous tetrahydrofuran (4 mL) under nitrogen at 0° C. was added methyl magnesium bromide (3 M in diethyl ether, 0.57 mL, 1.7 mmol). Then, the cooling bath was removed, and the reaction mixture was stirred at ambient temperature for 2 hours. Next, the reaction was quenched by adding saturated ammonium chloride to the reaction mixture. The resulting mixture was partitioned between ethyl acetate and water. The organic layer was separated and then washed with brine, dried with anhydrous sodium sulfate, filtered, and concentrated to provide the title compound (0.23 g, quantitative yield).

Part III—Synthesis of N-Ethyl-N-(3-(1-hydroxyethyl)phenyl)-3-(trifluoromethyl)benzenesulfonamide

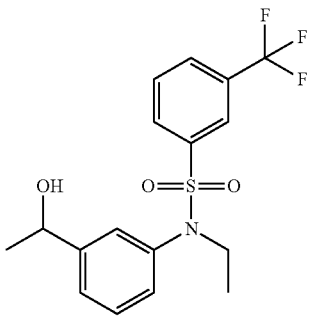 [SMILES: CCN(c1cccc(C(C)O)c1)S(=O)(=O)c1cccc(C(F)(F)F)c1]

To a solution of N-(3-acetylphenyl)-N-ethyl-3-(trifluoromethyl)benzenesulfonamide (0.23 g, 0.62 mmol) in ethanol (4 mL) at 0° C. was added sodium borohydride (0.07 g, 1.9 mmol). Then, the cooling bath was removed, and next the reaction mixture was stirred at ambient temperature for 4 hours. Next, the reaction was quenched by adding water to the reaction mixture. The resulting mixture was extracted with ethyl acetate, the organic layer was washed with water, washed with brine, dried with anhydrous sodium sulfate, filtered, and concentrated to provide the title compound (240 mg, quant. yield).

Part IV—Synthesis of N-(3-(1-(2-Chloro-6-fluorophenoxy)ethyl)phenyl)-N-ethyl-3-(trifluoromethyl)benzenesulfonamide

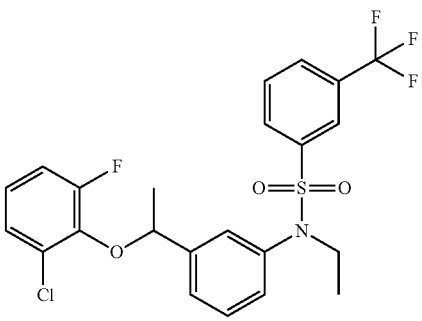 [SMILES: CCN(c1cccc(C(C)Oc2c(F)cccc2Cl)c1)S(=O)(=O)c1cccc(C(F)(F)F)c1]

To a solution of N-ethyl-N-(3-(1-hydroxyethyl)phenyl)-3-(trifluoromethyl)benzenesulfonamide (50 mg, 0.13 mmol), 2-chloro-6-fluorophenol (22 mg, 0.15 mmol), and triphenylphosphine (39 mg, 0.15 mmol) in anhydrous tetrahydrofuran (0.5 mL) at 0° C. was added diisopropyl azodicarboxylate (29 µL, 0.15 mmol). The reaction mixture was stirred at ambient temperature for 2 hours. Then, the reaction mixture was subjected to column chromatography purification eluting with a gradient of ethyl acetate in hexanes. Fractions containing the title compound in pure form were combined and concentrated to provide the title compound (42 mg, 62%). $^1$H-NMR (400 MHz, DMSO-d$_6$) δ 8.08 (d, 1H), 7.85 (m, 2H), 7.64 (s, 1H), 7.36 (m, 2H), 7.22 (m, 1H), 7.14 (m, 1H), 7.03 (m, 2H), 6.94 (s, 1H), 5.34 (q, 1H), 3.62 (m, 1H), 3.5 (m, 1H), 1.44 (d, 3H), 0.85 (t, 3H).

Example 19

Synthesis of N-(3-((2-Chloro-6-fluorobenzyl)oxy) phenyl)-N-(2,2,2-trifluoroethyl)-3-(trifluoromethyl) benzenesulfonamide

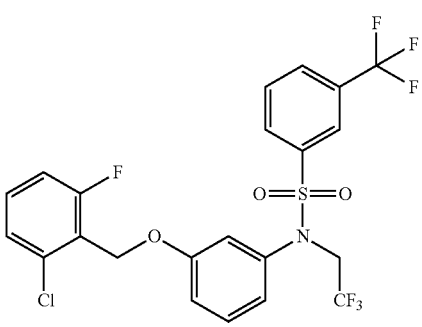 [SMILES: O=S(=O)(c1cccc(C(F)(F)F)c1)N(CC(F)(F)F)c1cccc(OCc2c(F)cccc2Cl)c1]

Part I—Synthesis of 3-Methoxy-N-(2,2,2-trifluoroethyl)aniline

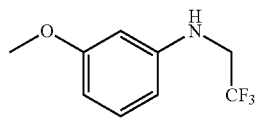

To a solution of 2,2,2-trifluoro-N-(3-methoxyphenyl)acetamide (10.4 g, 47.4 mmol) in THF (30 mL) was added a 1 M solution of borane in tetrahydrofuran (95 mL, 95 mmol). The resulting mixture was heated to reflux overnight. Next, the reaction vessel was cooled in an ice bath, and then the reaction was quenched by the dropwise addition of methanol (25 mL) to the reaction mixture. The resulting mixture was stirred at room temperature overnight. Then, the reaction mixture was concentrated to provide a residue that was purified using MPLC eluting with a gradient of 0-20% ethyl acetate in hexanes to afford 3-methoxy-N-(2, 2,2-trifluoroethyl)aniline (8.12 g, 83%) as a colorless oil.

Part II—Synthesis of 3-((2,2,2-Trifluoroethyl)amino)phenol

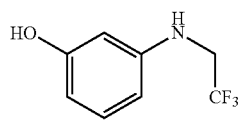

To a solution of 3-methoxy-N-(2,2,2-trifluoroethyl)aniline (7.55 g, 36.8 mmol) in acetic acid (25 mL) was added hydrobromic acid (21.8 g, 270 mmol), and the mixture was heated to reflux overnight. Next, the reaction mixture was cooled, then concentrated. The resulting concentrate was partitioned between chloroform and water. The mixture was neutralized carefully by adding saturated sodium bicarbonate. Then, the aqueous layer was reextracted with chloroform and the combined organic layers were dried (Na$_2$SO$_4$) and concentrated to provide a residue that was purified using MPLC eluting with a gradient of 0-60% ethyl acetate in hexanes to afford 3-((2,2,2-trifluoroethyl)amino)phenol (5.15 g, 73%) as a light orange oil.

Part III—Synthesis of 3-((2-Chloro-6-fluorobenzyl)oxy)-N-(2,2,2-trifluoroethyl)aniline

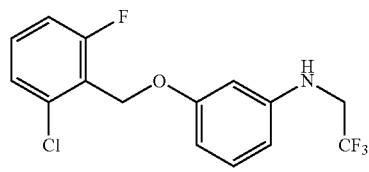 [SMILES: Fc1cccc(Cl)c1COc1cccc(NCC(F)(F)F)c1]

To a solution of 3-((2,2,2-trifluoroethyl)amino)phenol (403 mg, 2.11 mmol), (2-chloro-6-fluoro-phenyl)methanol (405 mg, 2.52 mmol) and triphenylphosphine (655 mg, 2.50 mmol) in THF (8 mL) was added diisopropyl azodicarboxylate (519 mg, 2.56 mmol). After 90 minutes, a few drops of methanol were added to the reaction mixture, and the mixture was concentrated to provide a residue. The residue was purified using MPLC eluting with a gradient of 0-25% ethyl acetate in hexanes to afford 3-((2-chloro-6-fluorobenzyl)oxy)-N-(2,2,2-trifluoroethyl)aniline (536 mg, 75%) as a colorless oil.

Part IV—Synthesis of N-(3-((2-Chloro-6-fluorobenzyl)oxy) phenyl)-N-(2,2,2-trifluoroethyl)-3-(trifluoromethyl)benzenesulfonamide

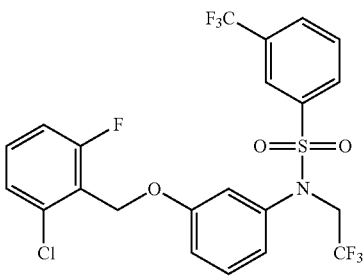 [SMILES: O=S(=O)(c1cccc(C(F)(F)F)c1)N(CC(F)(F)F)c1cccc(OCc2c(F)cccc2Cl)c1]

A solution of 3-((2-chloro-6-fluorobenzyl)oxy)-N-(2,2,2-trifluoroethyl)aniline (29.5 mg, 88.4 µmol) and 4-dimethylaminopyridine (55 mg, 450 µmol) in pyridine (0.4 mL) was heated at 90° C. for 8 hours. Then, the reaction mixture was cooled and concentrated. The concentrate was partitioned between ethyl acetate and 1 M sodium hydrogen sulfate. The organic layer was washed with saturated sodium bicarbonate, washed with brine, and then concentrated to provide a residue. The residue was purified using MPLC eluting with a gradient of 0-30% ethyl acetate in hexanes to afford N-(3-((2-chloro-6-fluorobenzyl)oxy)phenyl)-N-(2,2,2-trifluoroethyl)-3-(trifluoromethyl)benzenesulfonamide (33.5 mg, 63%) as a colorless oil. (ES, m/z): (M+Na)$^+$ 513. $^1$H-NMR (400 MHz, DMSO-d$_6$) δ 8.12 (d, 1H), 7.98 (d, 1H), 7.84 (m, 2H), 7.50 (m, 1H), 7.48 (d, 1H), 7.41-7.31 (m, 2H), 7.07 (d, 1H), 6.83 (d, 1H), 6.71 (s, 1H), 4.99 (s, 2H), 4.66 (q, 2H).

Example 20

Synthesis of N-(4-(Benzyloxy)phenyl)-N-ethyl-3-(trifluoromethyl)benzenesulfonamide

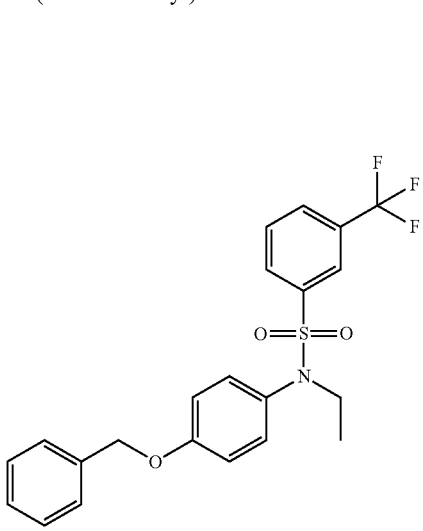

Part I—Synthesis of N-(4-(Benzyloxy)phenyl)-3-(trifluoromethyl)benzenesulfonamide

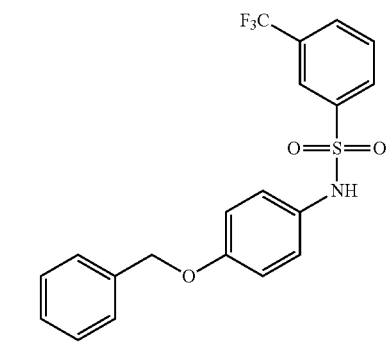 [SMILES: O=S(=O)(Nc1ccc(OCc2ccccc2)cc1)c1cccc(C(F)(F)F)c1]

To a solution of 4-benzyloxyaniline (515 mg, 2.58 mmol) in dichloromethane (5 mL) at 0° C. was added pyridine (412 mg, 5.20 mmol) followed by 3-(trifluoromethyl)benzene sulfonyl chloride (694 mg, 2.84 mmol). The reaction mixture was allowed to warm to room temperature, and then stirred for four hours. Next, methanol (100 μL) was added, and then the mixture was concentrated to provide a residue. The residue was purified via MPLC eluting with a gradient of 0-35% ethyl acetate in hexanes to afford N-(4-(benzyloxy)phenyl)-3-(trifluoromethyl)benzenesulfonamide (910 mg, 86%) as an off-white solid.

Part II—Synthesis of N-(4-(Benzyloxy)phenyl)-N-ethyl-3-(trifluoromethyl)benzenesulfonamide

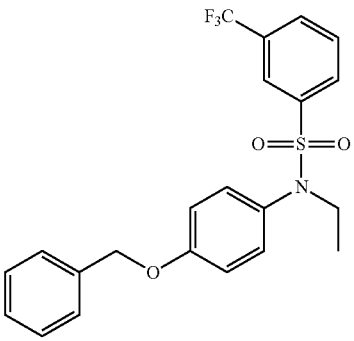 [SMILES: CCN(c1ccc(OCc2ccccc2)cc1)S(=O)(=O)c1cccc(C(F)(F)F)c1]

To a mixture of N-(4-(benzyloxy)phenyl)-3-(trifluoromethyl)benzenesulfonamide (498 mg, 1.22 mmol) and cesium carbonate (597 mg, 1.83 mmol) in acetonitrile (10 mL) was added iodoethane (390 mg, 2.50 mmol). The mixture was stirred at room temperature for 7 hours. Then, celite was added to the reaction mixture, the resulting mixture was diluted with ethyl acetate, and next the mixture was filtered. The filtrate was concentrated to provide a residue that was purified using MPLC eluting with a gradient of 0-25% ethyl acetate in hexanes to afford N-(4-(benzyloxy)phenyl)-N-ethyl-3-(trifluoromethyl)benzene-sulfonamide (425 mg, 79%) as a white solid. (ES, m/z): (M+Na)$^+$458. $^1$H-NMR (400 MHz, DMSO-d$_6$) δ 8.10 (m, 1H), 7.92-7.84 (m, 2H), 7.71 (s, 1H), 7.46-7.32 (m, 5H), 6.99-6.94 (m, 2H), 5.10 (s, 2H), 3.58 (q, 2H), 0.97 (t, 3H).

Example 21

Additional Compounds

The following additional compounds were prepared based on procedures above.

TABLE 7

| No. | Chemical Structure |
|---|---|
| 21A | 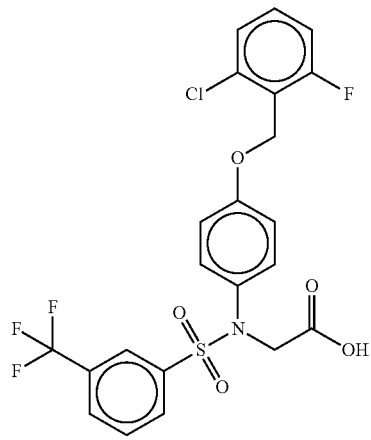 |

TABLE 7-continued

| No. | Chemical Structure |
|---|---|
| 21B | 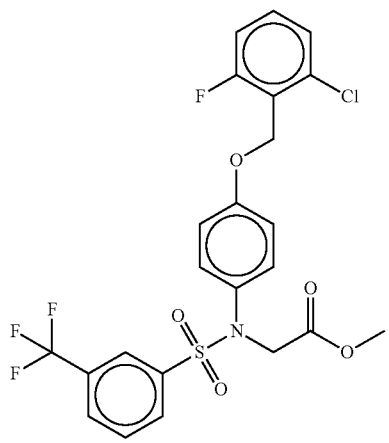 |
| 21C | 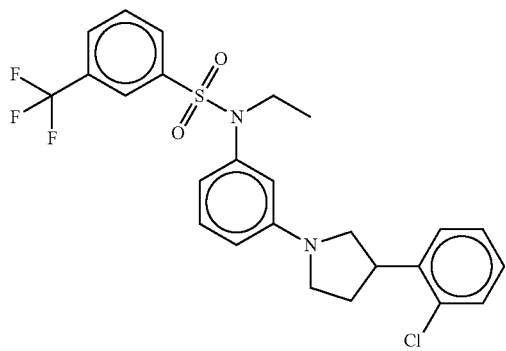 |
| 21D | 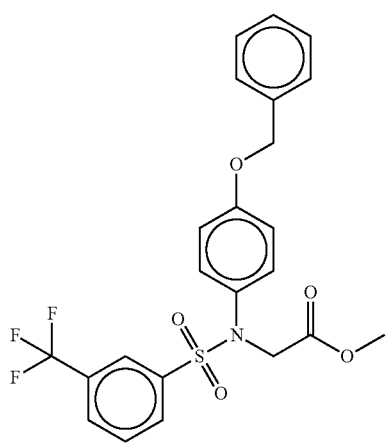 |

Example 22

Biological Assays for Agonist Activity Towards RORγ

Exemplary compounds from the above Examples were tested for ability to increase RORγ activity using (i) a RORγ-Ligand Binding Domain (LBD) TR-FRET Assay, and (ii) a Gal4-RORγ Luciferase Reporter Assay in HEK-293T Cells. Assay procedures and results are described below.

Part I—Procedures for RORγ-Ligand Binding Domain TR-FRET Assay

HIS-tagged RORγ-LBD protein was expressed in SF9 cells using a baculovirus expression system. The lysate was diluted in assay buffer (50 mM Tris pH 7.0, 50 mM KCl, 1 mM EDTA, 0.1 mM DTT, 0.01% BSA) to obtain RORγ-LBD final concentration of ~3 nM in a 384-well assay plate (need to titrate for each batch of protein).

A stock of biotinylated-LXXLL peptide from coactivator SRC1 (Biotin-CPSSHSSLTERHKILHRLLQEGSPS) was prepared in assay buffer and added to each well (200 nM final concentration). A solution of Europium tagged anti-HIS antibody (0.6 nM final concentration) and APC-conjugated streptavidin (30 nM final concentration) were also added to each well. RORγ antagonist ursolic acid was also included at a final concentration of 2 μM. Compounds were diluted in DMSO and further diluted in assay buffer with a final DMSO concentration at 1%.

The final assay mixture was incubated overnight at 4° C. or 2 hours at room temperature, and the fluorescence signal was measured on an Envision plate reader: (Excitation filter=340 nm; APC emission=665 nm; Europium emission=615 nm; dichroic mirror=D400/D630; delay time=100 μs, integration time=200 μs). 50% Effective concentration ($EC_{50}$) values for test compounds were calculated from the quotient of the fluorescence signal at 665 nm divided by the fluorescence signal at 615 nm. The quotient of the fluorescence signals in the absence of ursolic acid or test compound is set as 100. Max Response is defined as the upper plateau in the signal as determined by line-fit using a 4-parameter logistic model in PRISM (GraphPad).

Part II—Procedures for Gal4-RORγ Luciferase Reporter Assay in HEK-293T Cells

Transfection of HEK-293 Cells

In the following protocol, HEK-293 cells were transfected with a construct comprising the Gal4 DNA binding domain fused to the ligand binding domain of RORγ (Gal4-RORγ-LBD) in a pcDNA3.1neo plasmid, and also with a reporter construct comprising pGL4.31 Gal4-luciferase (Promega). Control cells were prepared similarly using empty pcDNA3.1neo and pGL4.31 vectors.

Trans-IT reagent (Mirus, 60 μL) at room temperature was added drop wise to OptiMEM (Invitrogen, 1.5 ml). This reagent mixture was mixed by inversion then incubated for 5 to 30 minutes at room temperature. It then was added to a solution of both expression vectors (5 μg each), mixed, and incubated at room temperature for about 20 minutes. HEK-293 cells were harvested from incubation flasks by removing the media, treating with TrypLE Express (Invitrogen), and incubating until the cells detached from the bottom of the flask (approximately 2-5 minutes). 10 Million cells were collected by centrifugation and re-suspended in 10 mL of Dulbecco's Modified Eagle Medium, High Glucose (DMEM, Invitrogen) containing 10% Fetal Bovine Serum and 100 IU each of penicillin and streptomycin. The re-suspended cells and the transfection mixture were added to a T75 flask, mixed and incubated overnight at 37° C. and 5% $CO_2$.

Assay for RORγ Activity

The cells were harvested as described above, counted, and centrifuged to obtain the desired number of cells, then re-suspended in complete growth media at $0.75 \times 10^6$ cells/mL. The RORγ antagonist, ursolic acid, was added to the cells at a final concentration of 2 μM. Cells were plated at 20 μL of cell suspension/well (10,000-15,000 cells/well) in white tissue culture treated 384 well plates. Test compounds were dissolved at 10 mM in DMSO then diluted into complete growth medium to 5× the final intended test concentration. These drug stock solutions, 5 μL/well were added to the tissue culture plate. The final DMSO concentration was 0.2%. The plates were briefly centrifuged then incubated overnight at 37° C. and 5% $CO_2$. To conduct the assay, the tissue culture plates were allowed to equilibrate to room temperature and One-Glo luciferase reagent (Promega, 25 μL/well) was added. The plates were briefly centrifuged then incubated at room temperature for 10 minutes. The luciferase intensity was read on an Envision plate reader (Perkin Elmer). RORγ activity was determined relative to controls and plotted as a function of test compound concentration using PRISM (GraphPad) to determine a 50% effective concentration ($EC_{50}$). The luciferase signal in the absence of ursolic acid or test compound is defined at 100. The Max Response is the upper plateau in the signal as determined by line-fit using a 4-parameter logistic model in PRISM (GraphPad).

Part III—Results

Experimental results are provided in Tables 8 and 9 below. The symbol "++++" indicates an $EC_{50}$ less than 0.5 μM. The symbol "+++" indicates an $EC_{50}$ in the range of 0.5 μM to 5 μM. The symbol "++" indicates an $EC_{50}$ in the range of greater than 5 μM to 10 μM. The symbol "+" indicates an $EC_{50}$ greater than 10 μM. The symbol "N/A" indicates that no data was available. The symbol "**" indicates a value greater than 200. The symbol "*" indicates a value in the range of greater than 150 to 200. The symbol "**" indicates a value in the range of greater than 90 to 150. The symbol "*" indicates a value in the range of 70 to 90.

TABLE 8

Assay Results for Sulfonamido Compounds.

| Compound Structure | TR-FRET Assay | | Gal4-RORγ Assay | |
|---|---|---|---|---|
| | $EC_{50}$ | Max Response | $EC_{50}$ | Max Response |
| (structure) | ++++ | *** | + | **** |
| (structure) | ++++ | *** | ++ | *** |
| (structure) | ++++ | *** | +++ | ** |

TABLE 8-continued

Assay Results for Sulfonamido Compounds.

| Compound Structure | TR-FRET Assay | | Gal4-RORγ Assay | |
|---|---|---|---|---|
| | EC$_{50}$ | Max Response | EC$_{50}$ | Max Response |
| (structure) | ++++ | *** | N/A | N/A |
| (structure) | +++ | ** | N/A | N/A |
| (structure) | ++++ | ** | N/A | N/A |
| (structure) | +++ | ** | N/A | N/A |

TABLE 8-continued

Assay Results for Sulfonamido Compounds.

| Compound Structure | TR-FRET Assay | | Gal4-RORγ Assay | |
|---|---|---|---|---|
| | $EC_{50}$ | Max Response | $EC_{50}$ | Max Response |
| (structure) | + | ** | N/A | N/A |
| (structure) | ++++ | ** | N/A | N/A |
| (structure) | +++ | ** | N/A | N/A |
| (structure) | ++++ | ** | N/A | N/A |

TABLE 8-continued

Assay Results for Sulfonamido Compounds.

| Compound Structure | TR-FRET Assay | | Gal4-RORγ Assay | |
|---|---|---|---|---|
| | EC$_{50}$ | Max Response | EC$_{50}$ | Max Response |
| (indazole-CH2-phenyl-N(Et)-SO2-phenyl-CF3) | + | ** | N/A | N/A |
| (CF3-phenyl-SO2-N(Et)-phenyl-CH2-N(Et)-phenyl-Cl) | +++ | ** | N/A | N/A |
| (benzoxazolone-CH2-phenyl-N(Et)-SO2-phenyl-CF3) | + | ** | N/A | N/A |
| (indoline-CH2-phenyl-N(Et)-SO2-phenyl-CF3) | +++ | ** | N/A | N/A |

TABLE 8-continued

Assay Results for Sulfonamido Compounds.

| Compound Structure | TR-FRET Assay | | Gal4-RORγ Assay | |
|---|---|---|---|---|
| | EC$_{50}$ | Max Response | EC$_{50}$ | Max Response |
| (structure) | + | ** | N/A | N/A |
| (structure) | + | ** | N/A | N/A |
| (structure) | + | ** | N/A | N/A |
| (structure) | +++ | **** | +++ | ** |
| (structure) | +++ | *** | + | ** |

TABLE 8-continued

Assay Results for Sulfonamido Compounds.

| Compound Structure | TR-FRET Assay | | Gal4-RORγ Assay | |
| --- | --- | --- | --- | --- |
| | EC$_{50}$ | Max Response | EC$_{50}$ | Max Response |
| (structure) | + | ** | N/A | N/A |
| (structure) | + | N/A | N/A | N/A |
| (structure) | ++++ | **** | +++ | ** |
| (structure) | ++++ | **** | + | N/A |

TABLE 8-continued

Assay Results for Sulfonamido Compounds.

| Compound Structure | TR-FRET Assay | | Gal4-RORγ Assay | |
|---|---|---|---|---|
| | EC$_{50}$ | Max Response | EC$_{50}$ | Max Response |
| (3-trifluoromethylphenyl-sulfonyl)(N-ethyl) anilinyl ether with 2-chloro-5-trifluoromethylbenzyl | + | *** | N/A | N/A |
| (3-trifluoromethylphenyl-sulfonyl)(N-ethyl) anilinyl ether with 2,5-dichlorobenzyl | ++++ | **** | ++ | *** |
| (3-trifluoromethylphenyl-sulfonyl)(N-ethyl) anilinyl ether with 2,4-dichlorobenzyl | + | ** | N/A | N/A |
| (3-trifluoromethylphenyl-sulfonyl)(N-ethyl) anilinyl ether with 2-chloro-3-trifluoromethylbenzyl | + | N/A | N/A | N/A |

TABLE 8-continued

Assay Results for Sulfonamido Compounds.

| Compound Structure | TR-FRET Assay | | Gal4-RORγ Assay | |
|---|---|---|---|---|
| | EC$_{50}$ | Max Response | EC$_{50}$ | Max Response |
| (structure) | + | N/A | N/A | N/A |
| (structure) | +++ | **** | +++ | ** |
| (structure) | +++ | **** | + | N/A |
| (structure) | + | N/A | N/A | N/A |
| (structure) | +++ | **** | +++ | ** |

TABLE 8-continued

Assay Results for Sulfonamido Compounds.

| Compound Structure | TR-FRET Assay | | Gal4-RORγ Assay | |
|---|---|---|---|---|
| | EC$_{50}$ | Max Response | EC$_{50}$ | Max Response |
| [structure: 3-(cyclohexylaminomethyl)phenyl N-ethyl 3-(trifluoromethyl)benzenesulfonamide] | + | N/A | N/A | N/A |
| [structure: 3-((2-chlorobenzyl)amino)phenyl N-ethyl 3-(trifluoromethyl)benzenesulfonamide] | ++++ | **** | +++ | ** |
| [structure: 3-(2,3-dihydro-1H-inden-2-yloxy)phenyl N-ethyl 3-(trifluoromethyl)benzenesulfonamide] | +++ | *** | N/A | N/A |
| [structure: 3-(cyclohexylmethoxy)phenyl N-ethyl 3-(trifluoromethyl)benzenesulfonamide] | ++++ | **** | N/A | N/A |

TABLE 8-continued

Assay Results for Sulfonamido Compounds.

| Compound Structure | TR-FRET Assay | | Gal4-RORγ Assay | |
|---|---|---|---|---|
| | EC$_{50}$ | Max Response | EC$_{50}$ | Max Response |
| *(structure: 2-fluoro-6-chlorobenzyloxy phenyl with N-ethyl-3-(trifluoromethyl)benzenesulfonamide)* | ++++ | **** | N/A | N/A |
| *(structure: indanyloxy phenyl with N-ethyl-3-(trifluoromethyl)benzenesulfonamide)* | ++++ | **** | N/A | N/A |
| *(structure: benzyloxy phenyl with N-ethyl-3-(trifluoromethyl)benzenesulfonamide)* | +++ | *** | N/A | N/A |

TABLE 9

Assay Results for Sulfone Compounds.

| Compound Structure | TR-FRET Assay | | Gal4-RORγ Assay | |
|---|---|---|---|---|
| | EC$_{50}$ | Max Response | EC$_{50}$ | Max Response |
| (structure 1) | +++ | ** | N/A | N/A |
| (structure 2) | ++++ | *** | ++++ | ** |
| (structure 3) | ++ | ** | +++ | * |
| (structure 4) | ++++ | *** | N/A | N/A |

TABLE 9-continued

Assay Results for Sulfone Compounds.

| Compound Structure | TR-FRET Assay | | Gal4-RORγ Assay | |
|---|---|---|---|---|
| | EC$_{50}$ | Max Response | EC$_{50}$ | Max Response |
| *(structure: 4-benzyloxyphenyl with CH(Et)-SO2-(4-chlorophenyl))* | +++ | *** | N/A | N/A |
| *(structure: 2-chloro-6-fluorobenzyloxyphenyl with CH(Et)-SO2-(4-chlorophenyl))* | ++++ | *** | +++ | * |
| *(structure: 3-benzyloxyphenyl with CH(Et)-SO2-(4-chlorophenyl))* | + | * | N/A | N/A |

TABLE 9-continued

Assay Results for Sulfone Compounds.

| Compound Structure | TR-FRET Assay | | Gal4-RORγ Assay | |
|---|---|---|---|---|
| | EC$_{50}$ | Max Response | EC$_{50}$ | Max Response |
| 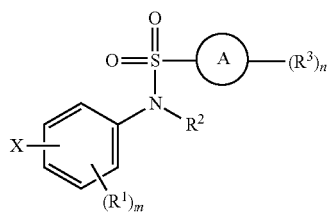 | ++++ | *** | N/A | N/A |

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:
1. A compound represented by Formula I:

(I)

or a pharmaceutically acceptable salt thereof; wherein:
A is phenylene, 5-6 membered heteroarylene, or $C_{3-6}$ heterocycloalkylene;
$R^1$ represents independently for each occurrence halogen, $C_{1-6}$ alkyl, $C_{1-6}$ haloalkyl, or $C_{3-6}$ cycloalkyl;
$R^2$ is $C_{1-6}$ alkyl optionally substituted with 1, 2, or 3 substituents independently selected from the group consisting of halogen, hydroxyl, and $C_{1-6}$ alkoxy;
$R^3$ is $C_{1-6}$ haloalkyl;
$R^4$ represents independently for each occurrence hydrogen, $C_{1-6}$ alkyl, or $C_{3-6}$ cycloalkyl;

X is one of the following:
(i) —O-aralkyl, —O-heteroaralkyl, —O-phenyl, —O-heteroaryl, —O-(partially unsaturated bicyclic carbocyclyl), —O—($C_{1-6}$ alkylene)—($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), or —N($R^4$)—($C_{1-6}$ alkylene)—($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, hydroxyl, and cyano;

(ii) —($C_{2-6}$ alkenylene)-phenyl, —($C_{2-6}$ alkenylene)-heteroaryl, —($C_{1-6}$ alkylene)-phenyl, —($C_{1-6}$ alkylene)-heteroaryl, —($C_{1-6}$ alkylene)-(partially unsaturated bicyclic heterocyclyl), —($C_{1-6}$ alkylene)-(partially unsaturated bicyclic oxo-heterocyclyl), -(5-6 membered heterocycloalkylene)-phenyl, or —($C_{3-6}$ cycloalkylene)-phenyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, hydroxyl, and cyano; or (iii) —($C_{1-6}$ alkylene)-$Z^1$ or —($C_{2-6}$ alkenylene)-$Z^1$, wherein $Z^1$ is —O-aralkyl, —O-heteroaralkyl, —O-phenyl, —O-heteroaryl, —O-(partially unsaturated bicyclic carbocyclyl), —O—($C_{1-6}$ alkylene)—($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), —N($R^4$)—($C_{1-6}$ alkylene)—($C_{3-6}$ cycloalkyl), or —N($R^4$)—($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, hydroxyl, and cyano;

m is 0, 1, or 2; and
n is 1, 2, or 3.

2. The compound of claim 1, wherein the compound is represented by Formula I-A:

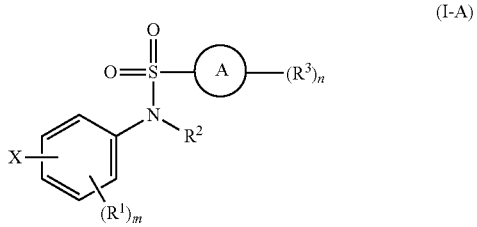

(I-A)

or a pharmaceutically acceptable salt thereof; wherein:

A is phenylene or a 5-6 membered heteroarylene;

$R^1$ represents independently for each occurrence halogen, $C_{1-6}$ alkyl, or $C_{3-6}$ cycloalkyl;

$R^2$ is $C_{1-6}$ alkyl optionally substituted with 1, 2, or 3 substituents independently selected from the group consisting of halogen, hydroxyl, and $C_{1-6}$ alkoxy;

$R^3$ is $C_{1-6}$ haloalkyl;

$R^4$ represents independently for each occurrence hydrogen, $C_{1-6}$ alkyl, or $C_{3-6}$ cycloalkyl;

X is one of the following:

(i) —O-aralkyl, —O-heteroaralkyl, —O-phenyl, —O-heteroaryl, —O-(partially unsaturated bicyclic carbocyclyl), —O—($C_{1-6}$ alkylene)—($C_{3-6}$ cycloalkyl), —N($R^4$)-aralkyl, —N($R^4$)-phenyl, —N($R^4$)-(partially unsaturated bicyclic carbocyclyl), or —N($R^4$)—($C_{1-6}$ alkylene)—($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy;

(ii) —($C_{2-6}$ alkenylene)-phenyl, —($C_{2-6}$ alkenylene)-heteroaryl, —($C_{1-6}$ alkylene)-phenyl, —($C_{1-6}$ alkylene)-heteroaryl, —($C_{1-6}$ alkylene)-(partially unsaturated bicyclic heterocyclyl), —($C_{1-6}$ alkylene)-(partially unsaturated bicyclic oxo-heterocyclyl), or -(5-6 membered heterocycloalkylene)-phenyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy; or (iii) —($C_{1-6}$ alkylene)-$Z^1$ or —($C_{2-6}$ alkenylene)-$Z^1$, wherein $Z^1$ is —O-aralkyl, —O-heteroaralkyl, —O-phenyl, —O-heteroaryl, —O-(partially unsaturated bicyclic carbocyclyl), —O—($C_{1-6}$ alkylene)—($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), or —N($R^4$)—($C_{1-6}$ alkylene)—(C3-6 cycloalkyl), each of which is optionally substituted with 1, 2, or 3 substituents independently selected from the group consisting of halogen, $C_1$-6 haloalkyl, $C_{1-6}$ alkyl, $C_{3-6}$ cycloalkyl, $C_{1-6}$ alkoxy, and $C_{1-6}$ haloalkoxy;

m is 0, 1, or 2; and n is 1, 2, or 3.

3. The compound of claim 2, wherein A is phenylene.

4. The compound of claim 2, wherein A is a 5-6 membered heteroarylene.

5. The compound of claim 3, wherein n is 1.

6. The compound of claim 5, wherein $R^3$ is trifluoromethyl.

7. The compound of claim 5, wherein $R^2$ is $C_{1-6}$ alkyl.

8. The compound of claim 5, wherein $R^2$ is ethyl or propyl.

9. The compound of claim 2, wherein Xis —O-aralkyl, —O-heteroaralkyl, —O-phenyl, —O-heteroaryl, —O-(partially unsaturated bicyclic carbocyclyl), —O—($C_{1-6}$ alkylene)—($C_{3-6}$ cycloalkyl), —N($R^4$)-aralkyl, —N($R^4$)-phenyl, —N($R^4$)-(partially unsaturated bicyclic carbocyclyl), or —N($R^4$)—($C_{1-6}$ alkylene)—($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy.

10. The compound of claim 3, wherein X is —O-aralkyl or —O-(partially unsaturated bicyclic carbocyclyl), each of which is optionally substituted with 1 or 2 substituents independently selected from the group consisting of halogen and $C_{1-6}$ haloalkyl.

11. The compound of claim 8, wherein X is —O-benzyl substituted with 1 or 2 substituents independently selected from the group consisting of chloro, bromo, and fluoro.

12. The compound of claim 8, wherein X is —O—($C_{1-6}$ alkylene)-phenyl or —N($R^4$)—($C_{1-6}$ alkylene)-phenyl, each of which is substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy, where at least one substituent is present at the ortho position on the phenyl group in variable X.

13. The compound of claim 2, wherein X is —($C_{1-6}$ alkylene)-heteroaryl, —($C_{1-6}$ alkylene)-(partially unsaturated bicyclic heterocyclyl), —($C_{1-6}$ alkylene)-(partially unsaturated bicyclic oxo-heterocyclyl), or -(5-6 membered heterocycloalkylene)-phenyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy.

14. The compound of claim 3, wherein X is —($C_{1-6}$ alkylene)-$Z^1$, wherein $Z^1$ is —O-aralkyl, —N($R^4$)-aralkyl, or —N($R^4$)-phenyl, each of which is optionally substituted with 1, 2, or 3 substituents independently selected from the group consisting of halogen, $C_{1-6}$ haloalkyl, and $C_{1-6}$ alkyl.

15. The compound of claim 3, wherein X is attached at the meta or para position of the sulfonamido-phenyl group.

16. The compound of claim 15, wherein m is 0.

17. A compound in Table 1-1 or 8-1 below, or a pharmaceutically acceptable salt thereof:

TABLE 1-1

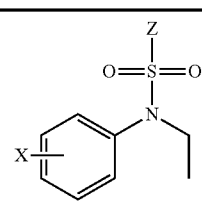

(I-C)

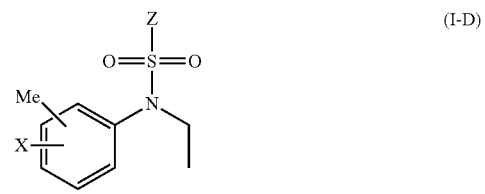

(I-D)

TABLE 1-1-continued
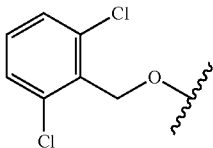
TABLE 8-1
Compound Structure
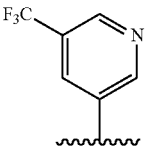

TABLE 8-1-continued
| Compound Structure |
|---|
| 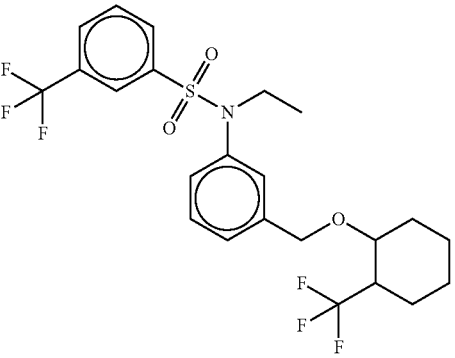 |
| 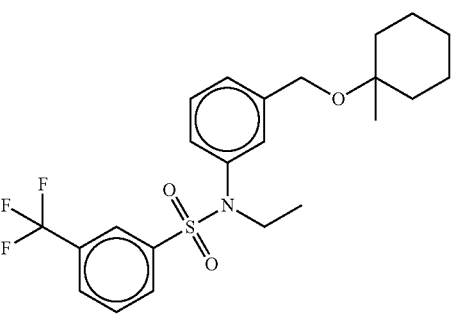 |
| 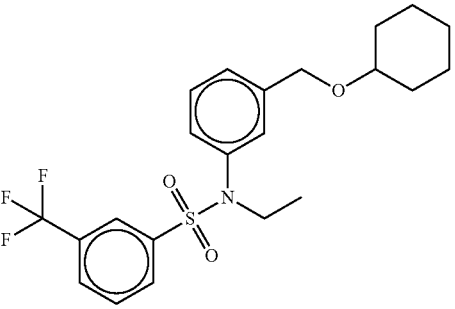 |
| 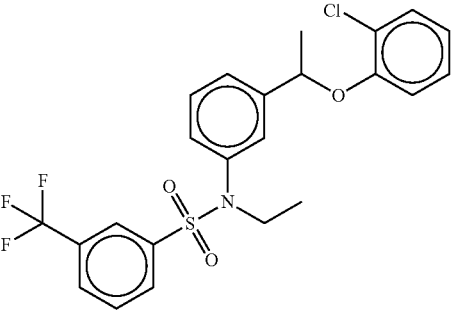 |
TABLE 8-1-continued
| Compound Structure |
|---|
| 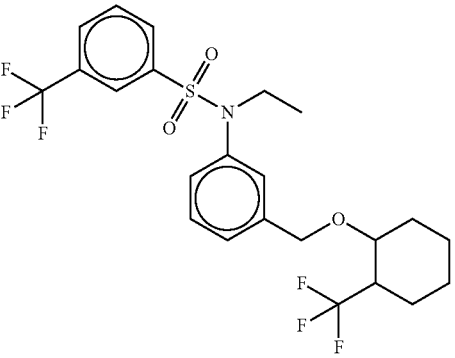 |
| 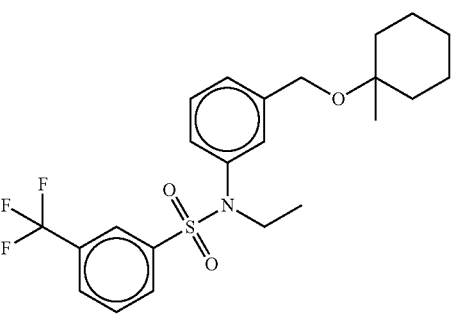 |
| 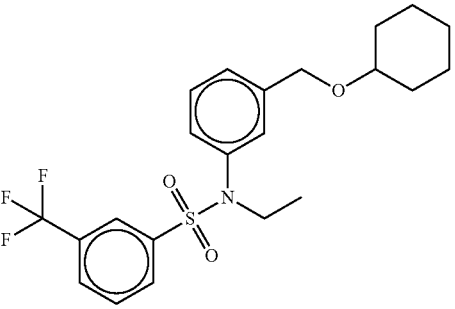 |
| 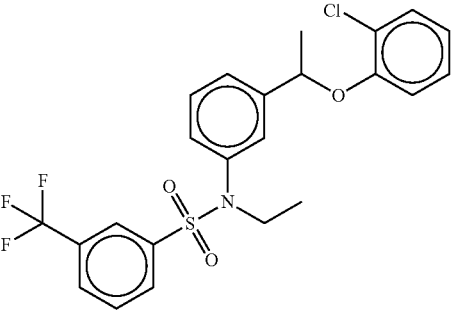 |
| 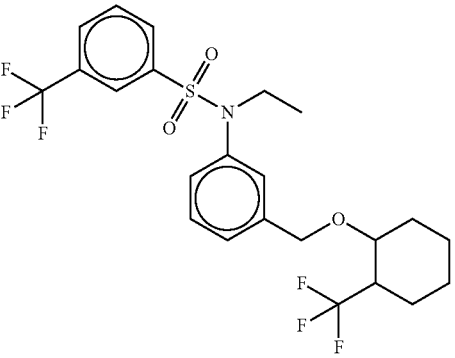 |

TABLE 8-1-continued
Compound Structure
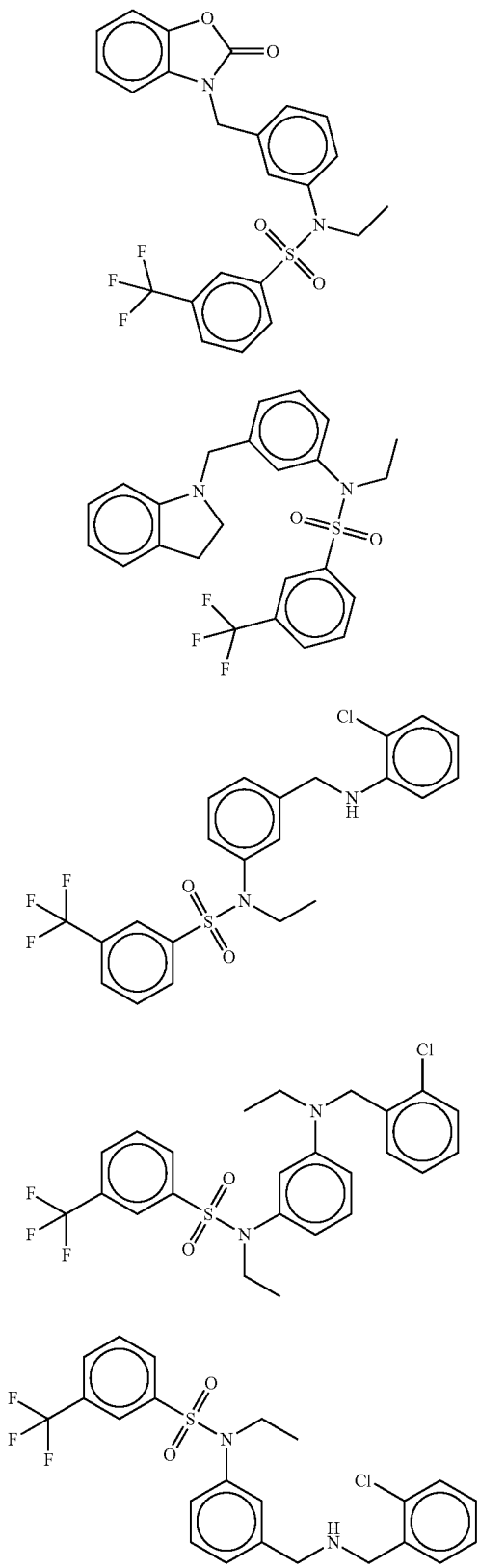
TABLE 8-1-continued
Compound Structure
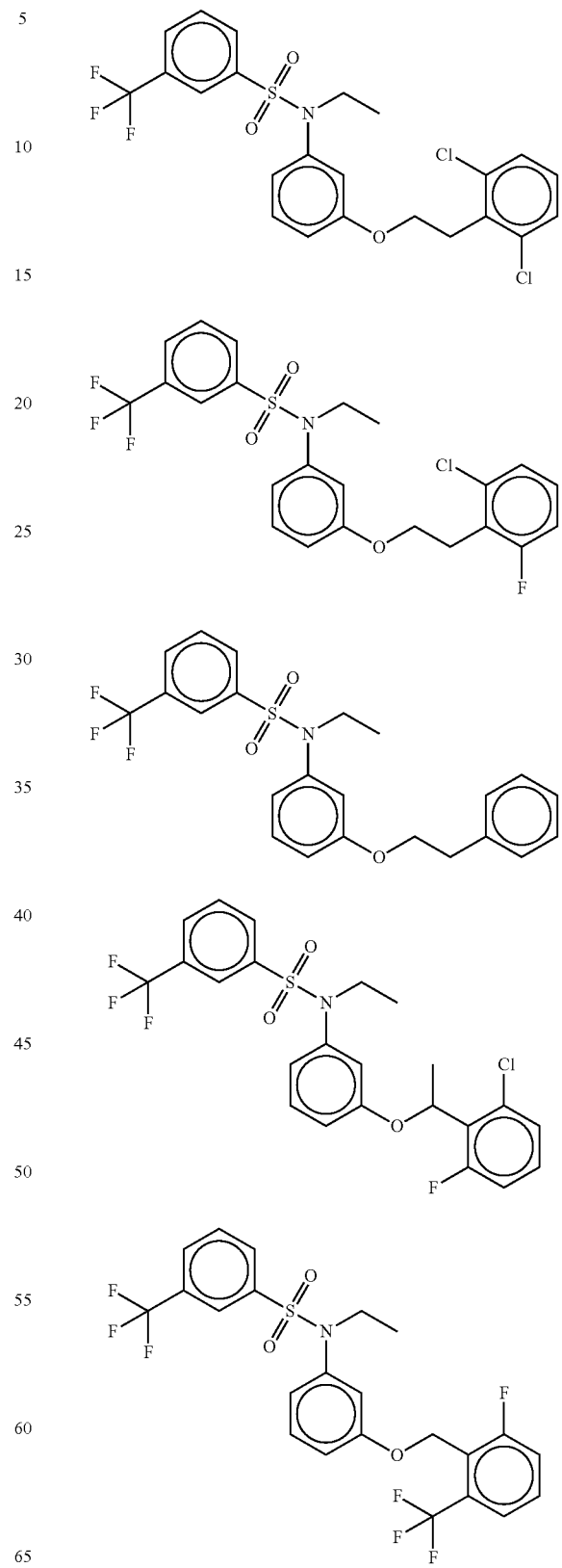

TABLE 8-1-continued

| Compound Structure |
|---|

TABLE 8-1-continued

Compound Structure

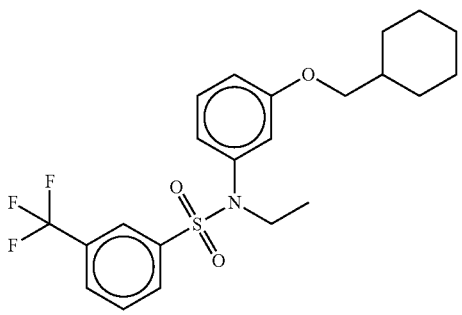

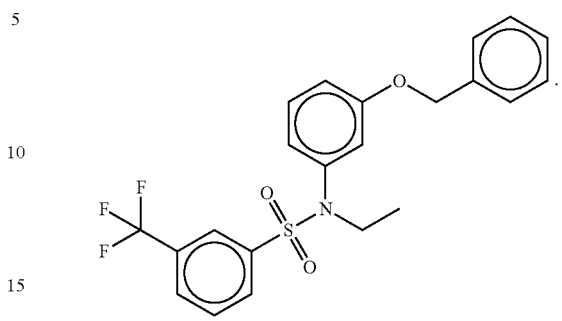

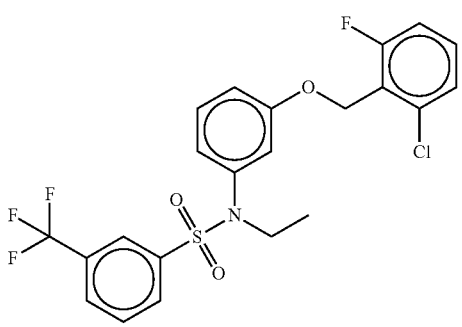

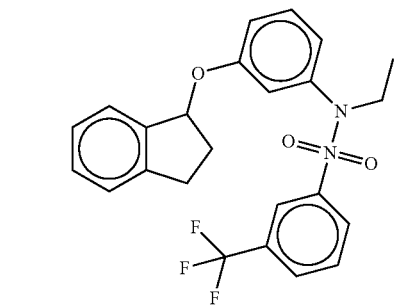

18. A pharmaceutical composition comprising a compound of claim 1 and a pharmaceutically acceptable carrier.

19. A method of treating a disorder selected from the group consisting of colon cancer, pancreatic cancer, breast cancer, ovarian cancer, prostate cancer, squamous cell carcinoma, basal cell carcinoma, adenocarcinoma, sweat gland carcinoma, sebaceous gland carcinoma, lung cancer, leukemia, bladder cancer, stomach cancer, cervical cancer, testicular cancer, skin cancer, rectal cancer, thyroid cancer, kidney cancer, uterus cancer, esophagus cancer, liver cancer, an acoustic neuroma, oligodendroglioma, meningioma, neuroblastoma, and retinoblastoma, comprising administering a therapeutically effective amount of a compound of claim 1 to a subject in need thereof to ameliorate a symptom of the disorder.

20. The method of claim 19, wherein the disorder is colon cancer, pancreatic cancer, breast cancer, ovarian cancer, prostate cancer, squamous cell carcinoma, basal cell carcinoma, adenocarcinoma, lung cancer, leukemia, bladder cancer, stomach cancer, cervical cancer, testicular cancer, skin cancer, rectal cancer, thyroid cancer, kidney cancer, uterus cancer, or esophagus cancer.

21. The method of claim 19, wherein the subject is a human.

22. A method of promoting the activity of RORγ, comprising exposing a RORγ to an effective amount of a compound of claim 1 to promote the activity of said RORγ.

23. A pharmaceutical composition comprising a compound of claim 2 and a pharmaceutically acceptable carrier.

24. A pharmaceutical composition comprising a compound of claim 10 and a pharmaceutically acceptable carrier.

* * * * *